US010208082B2

(12) United States Patent
Kasuya et al.

(10) Patent No.: US 10,208,082 B2
(45) Date of Patent: Feb. 19, 2019

(54) SUSTAINED-RELEASE PHARMACEUTICAL COMPOSITION FOR TREATMENT AND PREVENTION OF EYE DISEASE

(71) Applicant: Daiichi Sankyo Company, Limited, Chuo-ku, Tokyo (JP)

(72) Inventors: Yuji Kasuya, Sumida-ku (JP); Yasuhiro Nakagami, Kobe (JP); Emiko Hatano, Urayasu (JP); Tatsuya Inoue, Ota-ku (JP); Kazuhiro Yoshida, Setagaya-ku (JP); Satoshi Komoriya, Fujisawa (JP); Yoko Murakami, Bunkyo-ku (JP); Masaru Iwasaki, Edogawa-ku (JP); Atsunobu Sakamoto, Edogawa-ku (JP); Kayoko Masuda, Setagaya-ku (JP); Masako Minami, Taitou-ku (JP); Mayumi Iizuka, Edogawa-ku (JP); Yasunori Ono, Ichikawa (JP); Takashi Ohnuki, Yamato (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 15/510,208

(22) PCT Filed: Sep. 9, 2015

(86) PCT No.: PCT/JP2015/075535
§ 371 (c)(1),
(2) Date: Mar. 9, 2017

(87) PCT Pub. No.: WO2016/039359
PCT Pub. Date: Mar. 17, 2016

(65) Prior Publication Data
US 2017/0260228 A1 Sep. 14, 2017

(30) Foreign Application Priority Data
Sep. 10, 2014 (JP) .................. 2014-183854

(51) Int. Cl.
| | |
|---|---|
| A61P 27/02 | (2006.01) |
| A61K 31/58 | (2006.01) |
| C07J 71/00 | (2006.01) |
| C07J 63/00 | (2006.01) |
| A61K 9/00 | (2006.01) |
| A61K 9/16 | (2006.01) |
| A61K 9/20 | (2006.01) |

(52) U.S. Cl.
CPC ........... C07J 71/001 (2013.01); A61K 9/0048 (2013.01); A61K 9/1647 (2013.01); A61K 9/204 (2013.01); A61K 31/58 (2013.01); A61P 27/02 (2018.01); C07J 63/008 (2013.01)

(58) Field of Classification Search
CPC ........ C07J 71/001; C07J 63/008; A61P 27/02; A61K 9/0048; A61K 9/1647; A61K 9/204; A61K 31/58
See application file for complete search history.

(56) References Cited

U.S. PATENT DOCUMENTS

2015/0148384 A1 5/2015 Anderson et al.

FOREIGN PATENT DOCUMENTS

| WO | 99/65478 A1 | 12/1999 |
|---|---|---|
| WO | 2004/064723 A2 | 8/2004 |
| WO | 2009/023232 A1 | 2/2009 |
| WO | 2009/089545 A1 | 7/2009 |
| WO | 2009/129546 A1 | 10/2009 |
| WO | 2009/129548 A1 | 10/2009 |
| WO | 2009/146216 A2 | 12/2009 |
| WO | 2011/130302 A2 | 10/2011 |

(Continued)

OTHER PUBLICATIONS

Eppinger, M., et al., "Acetaldehyde Dehydrogenase," UniProt [online], Jun. 15, 2010, Accession No. D5DK18; reference location: "Genome Sequences of the Industrial Vitamin B12-Producers B. megaterium QM B1551 and DSM319 Reveal New Insights Into the Bacillus Genome Evolution and Pan-Genome Structure," submitted Feb. 2010 to the EMBL/GenBank/DDBJ databases; Jozwik, I.K, et al., "Structural Basis of Steroid Binding and Oxidation by the Cytochrome P450 CYP109E1 From Bacillus megaterium," FEBS Journal 283(22):4128-4148, Nov. 2016; 2 pages.
Eppinger, M., et al., "Cytochrome P450," UniProt [online], Jun. 15, 2010, Accession No. D5DP07; reference location: "Genome Sequences of the Industrial Vitamin B12-Producers B. megaterium QM B1551 and DSM319 Reveal New Insights Into the Bacillus Genome Evolution and Pan-Genome Structure," submitted Feb. 2010 to the EMBL/GenBank/DDBJ databases; 2 pages.
Extended European Search Report dated Mar. 16, 2018, issued in European Application No. 15 840 177.8, filed Sep. 9, 2015, 12 pages.

(Continued)

Primary Examiner — Yong S. Chong
(74) Attorney, Agent, or Firm — Christensen O'Connor Johnson Kindness PLLC

(57) ABSTRACT

The present invention relates to a terpenoid derivative that has the ability to activate the Keap1/Nrf2/ARE signaling pathway and is excellent in anti-inflammatory action and cytoprotective action, and a sustained-release pharmaceutical composition effective for the treatment and prevention of a posterior eye disease caused by oxidative stress, comprising the terpenoid derivative as an active ingredient. The present invention provides a local administration-type sustained-release pharmaceutical composition for the treatment or prevention of a posterior eye disease, comprising the terpenoid derivative of the present invention as an active ingredient, wherein the sustained-release pharmaceutical composition maintains a pharmacological action thereof for 1 week or longer by the sustained release of the terpenoid derivative under physiological conditions and has a base material administrable to the vitreous body and a form administrable to the vitreous body.

12 Claims, 9 Drawing Sheets

Specification includes a Sequence Listing.

(56) References Cited

FOREIGN PATENT DOCUMENTS

| | | |
|---|---|---|
| WO | 2012/125488 A1 | 9/2012 |
| WO | 2013/188818 A1 | 12/2013 |
| WO | 2014/148455 A1 | 9/2014 |

OTHER PUBLICATIONS

Gautam, R., and S.M. Jachak, "Recent Developments in Anti-Inflammatory Natural Products," Medicinal Research Reviews 29(5):767-820, Sep. 2009.

Honda, T., et al., "A Novel Dicyanotriterpenoid, 2-Cyano-3,12-dioxoolean-1,9(11)-dien-28-onitrile, Active at Picomolar Concentrations for Inhibition of Nitric Oxide Production," Bioorganic & Medicinal Chemistry Letters 12(1):1027-1030, Jan. 2002.

Katayama, S., "Anti-Oxidative Action by Soybean Saponin Which Activates Nrf2-ARE Pathway," Fragrance Journal (Japan) 41(2):57-63, Feb. 2013 [English translation].

Katayama, S., HCAPLUS Database, Chemical Abstract, Jan. 1, 2013, Accession No. 2013:372298; reference location: "Soyasaponins Mediate Antioxidative Stress Activity via the Nrf2-ARE Pathway," Fragrance Journal (Japan) 41(2):57-63, Feb. 2013; 5 pages.

Katayama, S., "Soyasaponins Mediate Antioxidative Stress Activity via the Nrf2-ARE Pathway," Fragrance Journal (Japan) 41(2):57-63, Feb. 2013 [with English abstract].

Khelaifia, S., et al., "Biotin Biosynthesis Cytochrome P450," UniProt [online], Jul. 9, 2014, Accession No. A0A024P841; reference location: "Draft Genome Sequence of Halobacillus karajensis HK-03," submitted May 2014 to the EMBL/GenBank/DDBJ databases;1 page.

Liu, L, et al., "Cytochrome P450," UniProt [online], Accession No. G2RKC9, Nov. 16, 2011; reference location: "Complete Genome Sequence of the Industrial Strain Bacillus megaterium WSH-002," Journal of Bacteriology 193(22):6389-6390, Nov. 2011; 2 pages.

Chua, P., et al., "Draft Genome Sequences of Two Cellulolytic *Paenibacillus* sp. Strains, MAEPY1 and MAEPY2, From Malaysian Landfill Leachate," Genome Announcements 2(1):e00065-14, Jan.-Feb. 2014, 2 pages.

Eppinger, M., et al., "Cytochrome P450 [Bacillus megaterium QM B1551]," Nucleic Acid Sequence Accession No. ADE70895.1, submitted to GenBank on Jan. 30, 2014, <https://www.ncbi.nlm.nih.gov/protein/ADE70895> [retrieved Jul. 24, 2017], 2 pages.

Jia, N., et al., "Genome Sequence of Bacillus endophyticus and Analysis of Its Companion Mechanism in the Ketogulonigenium vulgare—Bacillus Strain Consortium," PLoS One 19(8):e0135104, Aug. 2015, 17 pages.

Liu, L., et al., "Complete Genome Sequence of the Industrial Strain Bacillus megaterium WSH-002," Journal of Bacteriology 193(22):6389-6390, Nov. 2011.

Liu, L., et al., "Cytochrome P450 [Bacillus megaterium WSH-002]," Nucleic Acid Sequence Accession No. AEN88225.1, submitted to GenBank on Jan. 31, 2014, <https://www.ncbi.nlm.nih.gov/protein/AEN88225> [retrieved Jul. 24, 2017], 2 pages.

International Preliminary Report on Patentability dated Mar. 14, 2017, issued in corresponding International Application No. PCT/JP2015/075535, filed Sep. 9, 2015, 15 pages.

International Search Report dated Nov. 24, 2015, issued in corresponding International Application No. PCT/JP2015/075535, filed Sep. 9, 2015, 8 pages.

Aleksunes, L.M., et al., "Transcriptional Regulation of Renal Cytoprotective Genes by Nrf2 and Its Potential Use as a Therapeutic Target to Mitigate Cisplatin-Induced Nephrotoxicity," Journal of Pharmacology and Experimental Therapeutics 335(1):2-12, Oct. 2010.

Boutten, A., et al., "NRF2 Targeting: A Promising Therapeutic Strategy in Chronic Obstructive Pulmonary Disease," Trends in Molecular Medicine 17(7):363-371, Jul. 2011.

Brennan, L.A., et al. "Oxidative Stress Defense and Repair Systems of the Ocular Lens," Frontiers in Bioscience E4:141-155, Jan. 2012.

Chowdhry, S., et al., "Loss of Nrf2 Markedly Exacerbates Nonalcoholic Steatohepatitis," Free Radical Biology and Medicine 48(2):357-371, Jan. 2010.

Honda, T., et al., "Design and Synthesis of 2-cyano-3,12-dioxoolean-1,9-dien-28-oic Acid, a Novel and Highly Active Inhibitor of Nitric Oxide Production in Mouse Macrophages," Bioorganic & Medicinal Chemistry Letters 8(19):2711-2714, Oct. 1998.

Hye-Youn, C., and S.R. Kleeberger, "Nrf2 Protects Against Airway Disorders," Toxicology and Applied Pharmacology 244(1):43-56, Apr. 2010.

Rojas-Rivera, J., et al., "Antioxidants in Kidney Diseases: The Impact of Bardoxolone Methyl," International Journal of Nephrology 2012:321714, Apr. 2012,11 pages.

Saha, P.K., et al., "The Triterpenoid 2-Cyano-3,12-dioxooleana-1,9-dien-28-oic-acid Methyl Ester Has Potent Anti-Diabetic Effects in Diet-Induced Diabetic Mice and Lepr(db/db) Mice," Journal of Biological Chemistry 285(52):40581-40592, Dec. 2010.

Sussan, T.E., et al., "Targeting Nrf2 With the Triterpenoid CDDO-Imidazolide Attenuates Cigarette Smoke-Induced Emphysema and Cardiac Dysfunction in Mice," Proceedings of the National Academy of Sciences of the USA (PNAS) 106(1):250-255, Jan. 2009.

Thrimawithana, T.R., et al., "Drug Delivery to the Posterior Segment of the Eye," Drug Discovery Today 16(5/6):270-277, Mar. 2011.

Vomhof-Dekrey, E.E., and M.J. Picklo, Sr., "The Nrf2-Antioxidant Response Element Pathway: A Target for Regulating Energy Metabolism," Journal of Nutritional Biochemistry 23(10):1201-1206, Oct. 2012.

Wei, Y., et al., "Nrf2 Has a Protective Role Against Neuronal and Capillary Degeneration in Retinal Ischemia—Reperfusion Injury," Free Radical Biology and Medicine 51(1):216-224, Jul. 2011.

Yadav, U.C.S., et al., "Emerging Role of Antioxidants in the Protection of Uveitis Complications," Current Medicinal Chemistry 18(6):931-942,2011.

Yi, D., "Condition Control by Oxidative Stress Response System," Biochemistry 81(6):447-455, 2009.

Zhang Y., et al., "Advanced Materials and Processing for Drug Delivery: The Past and the Future," Advanced Drug Delivery Reviews 65(1)104-120, Jan. 2013.

Second Office Action dated Oct. 16, 2018, in corresponding Chinese Application No. 201580046568X, 15 pages.

[Figure 1]
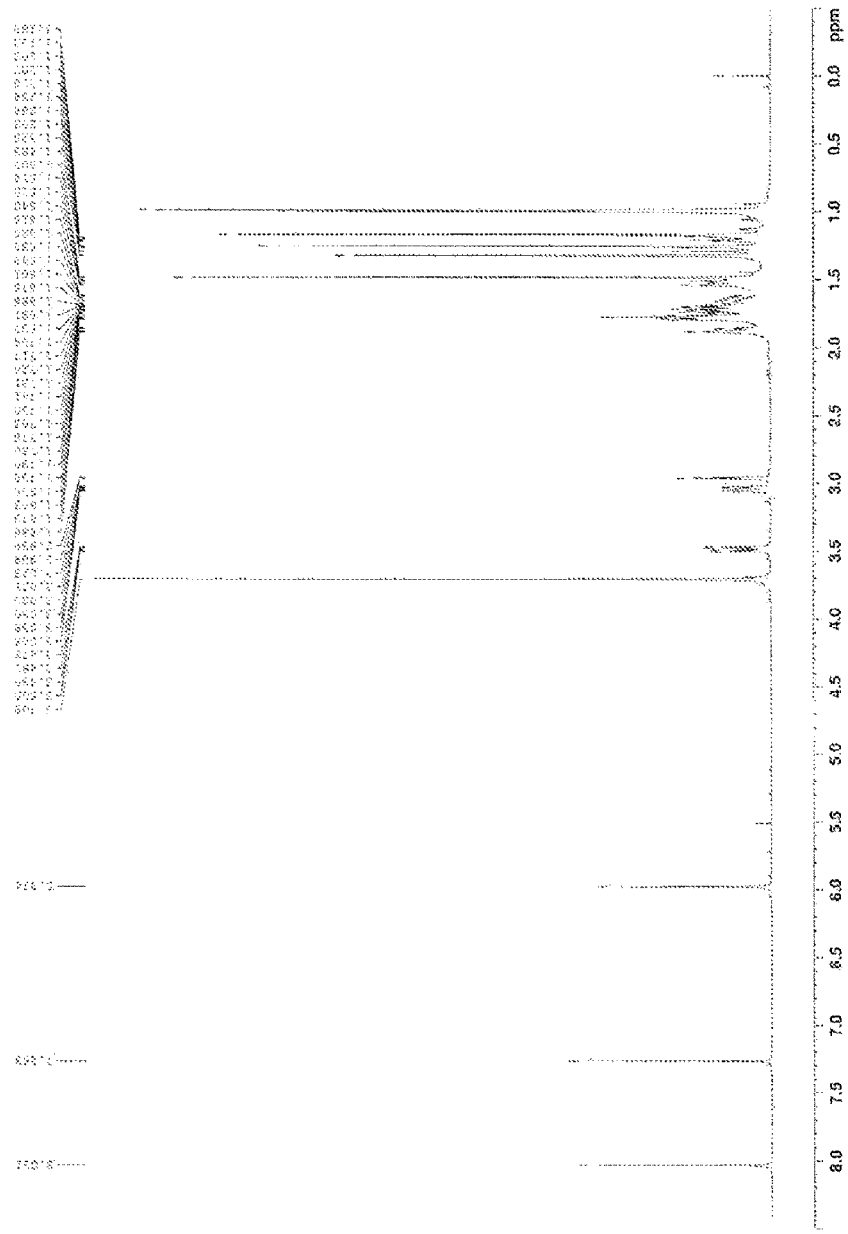

[Figure 2]
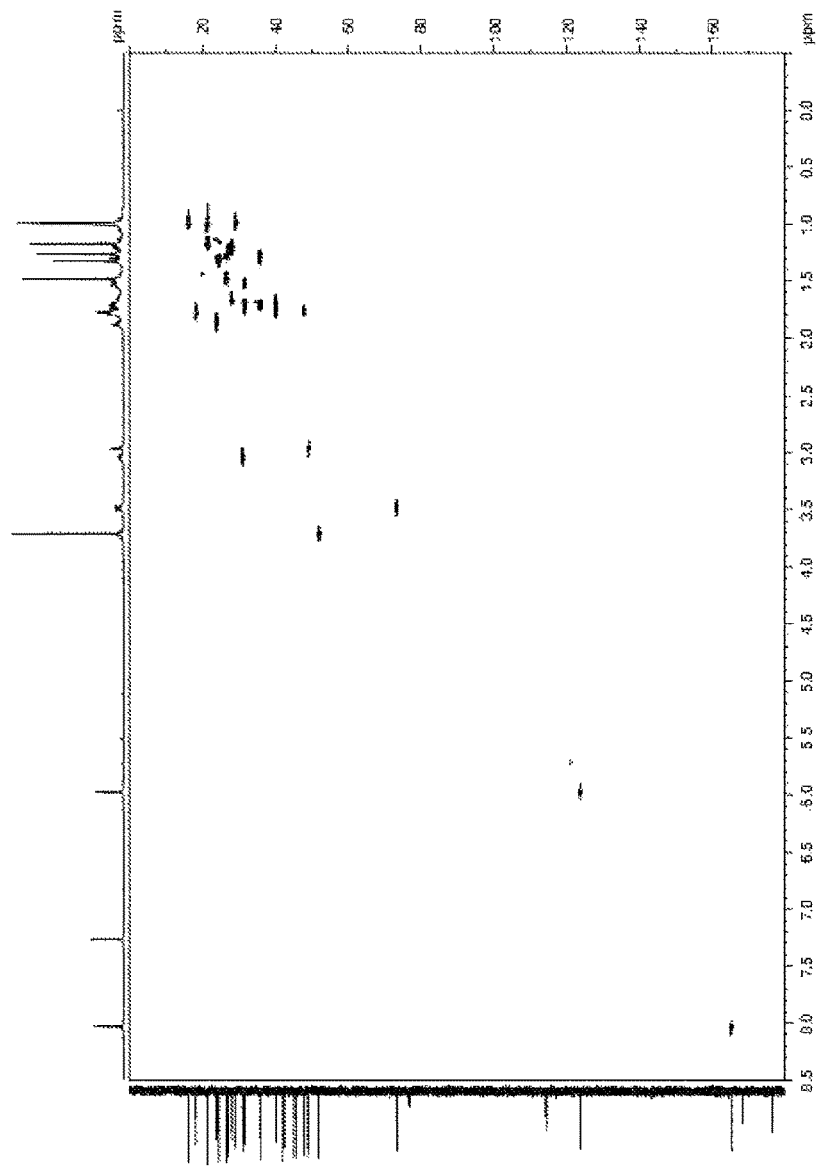

[Figure 3]
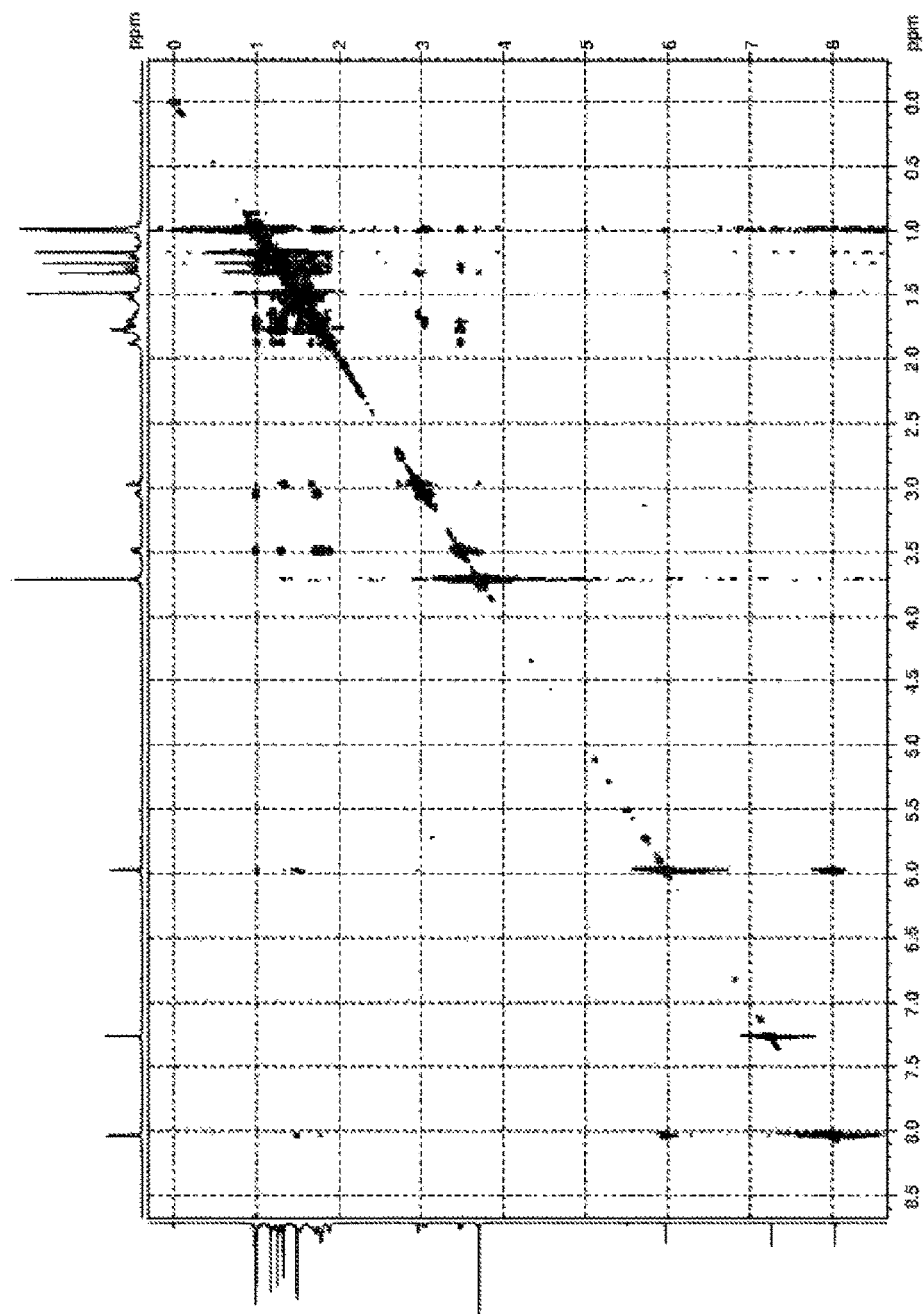

[Figure 4]
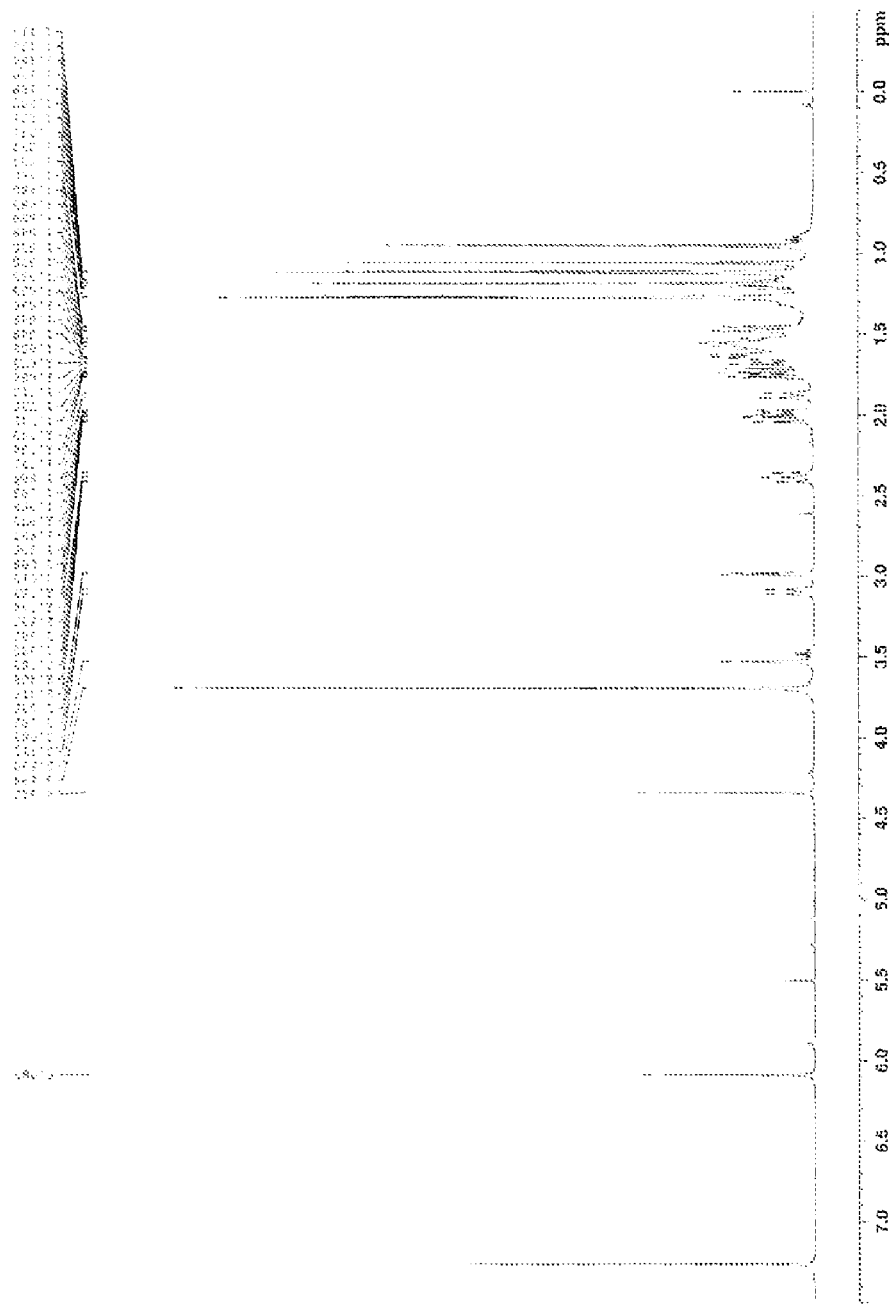

[Figure 5]
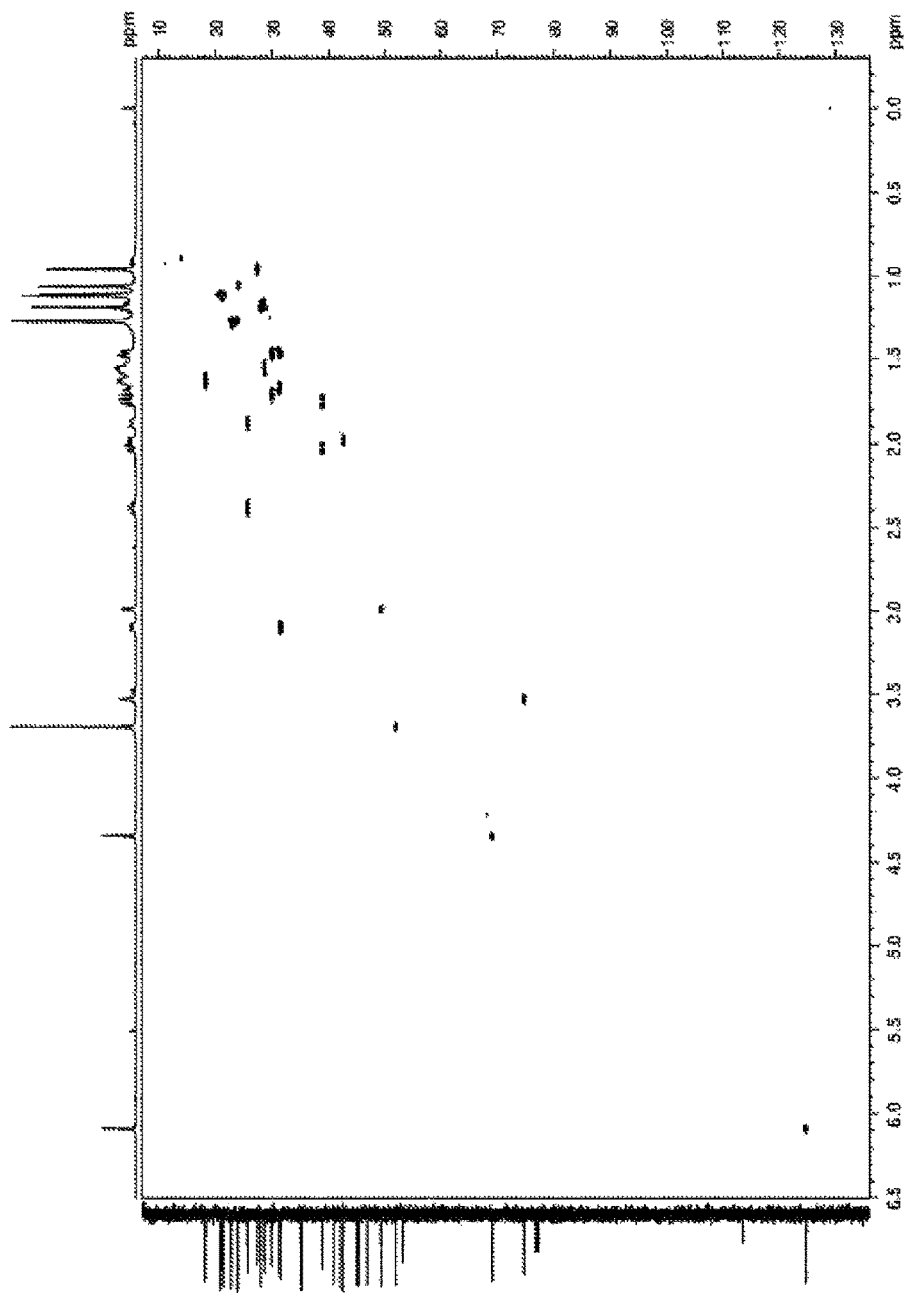

[Figure 6]
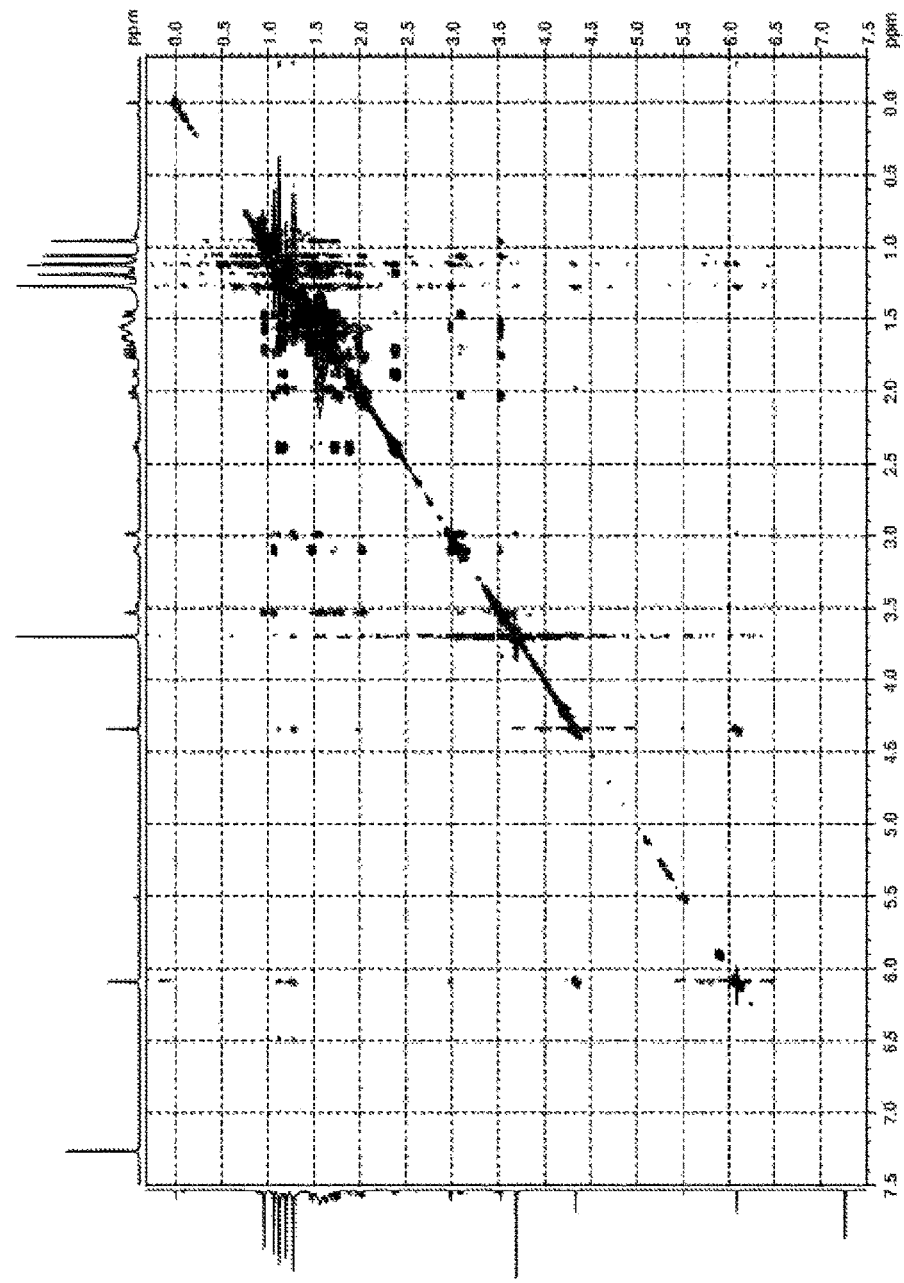

[Figure 7]

SEQ ID NO: 1: Partial nucleotide sequence of SANK 70214 16S rDNA

GCGTGCCTAATACATGCAAGTCGAGCGGACGTTTTTGAAGCTTCCTTTAAAAACGTTAGCGGCGGACGGGTGAGTAACAC
GTGGGCAACCTACCTTATCGACTGGGATAACTCCGGGAAACCGGGGCTAATACCGGATAACATCTAGCACCTCCTGGTGC
CGGATTGAAAGAGGGCTTCTTGCTCTCACGATGAGATGGGCCCGCGGCGCATTAGCTAGTTGGAGAGGTAATGGCTCCCC
AAGGCGACGATGCGTAGCCGACCTGAGAGGGTGATCGGCCACACTGGGACTGAGACACGGCCCAGACTCCTACGGGAGGC
AGCAGTAGGGAATCTTCCGCAATGGACGAAAGTCTGACGGAGCAACGCCGCGTGAGTGATGAAGGGTTTCGGCTCGTAAA
GCTCTGTTATGAGGGAAGAACACGTACCGTTCGAATAGGGCGGTACCTTGACGGTACCTCATCAGAAAGCCACGGCTAAC
TACGTGCCAGCAGCCGCGGTAATACGTAGGTGGCAAGCGTTGTCCGGAATTATTGGGCGTAAAGCGCGCGCAGGCGGCCT
TTTAAGTCTGATGTGAAATCTTGCGGCTCAACCGCAAGCGGCCATTGGAAACTGGGAGGCTTGAGTACAGAAGAGGAGAG
TGGAATTCCACGTGTAGCGGTGAAATGCGTAGATATGTGGAGGAACACCAGTGGCGAAGGCGACTCTCTGGTCTGTAACT
GACGCTGAGGCGCGAAAGCGTGGGGAGCAAACAGGATTAGATACCCTGGTAGTCCACGCCGTAAACGATGAGTGCTAGGT
GTTAGGGGTTTCGATGCCCGTAGTGCCGAAGTTAACACATTAAGCACTCCGCCTGGGGAGTACGGCCGCAAGGCTGAAAC
TCAAAGGAATTGACGGGGGCCCGCACAAGCAGTGGAGCATGTGGTTTAATTCGAAGCAACGCGAAGAACCTTACCAGGTC
TTGACATCCTTTGACCACTCTGGAGACAGAGCTTCCCCTTCGGGGGCAAAGTGACAGGTGGTGCATGGTTGTCGTCAGCT
CGTGTCGTGAGATGTTGGGTTAAGTCCCGCAACGAGCGCAACCCTTGACCTTAGTTGCCAGCATTTAGTTGGGCACTCTA
AGGTGACTGCCGGTGACAAACCGGAGGAAGGTGGGGATGACGTCAAATCATCATGCCCCTTATGACCTGGGCTACACACG
TGCTACAATGGATGGTACAAAGGGTTGCGAAGCCGCGAGGTGAAGCCAATCCCATAAAGCCATTCTCAGTTCGGATTGTA
GGCTGCAACTCGCCTGCATGAAGCTGGAATTGCTAGTAATCGCGGATCAGCATGCCGCGGTGAATACGTTCCCGGGCCTT
GTACACACCGCCCGTCACACCACGAGAGTTTGTAACACCCGAAGTCGGTGAGGTAACCTTTTGGAGCCAGCCGCCGAAGG
TGGGACAGATGATTGGGGTGAAGTCGTAACAAGGTA

[Figure 8]

SEQ ID NO: 2: Partial nucleotide sequence of SANK 70314 16S rDNA

GATGAACGCTGGCGGCGTGCCTAATACATGCAAGTCGAGCGAACTGATTAGAAGCTTGCTTCTATGACGTTAGCGGCGGA
CGGGTGAGTAACACGTGGGCAACCTGCCTGTAAGACTGGGATAACTTCGGGAAACCGAAGCTAATACCGGATAGGATCTT
CTCCTTCATGGAGATGATTGAAAGATGGTTTCGGCTATCACTTACAGATGGGCCCGCGGTGCATTAGCTAGTTGGTGAG
GTAACGGCTCACCAAGGCAACGATGCATAGCCGACCTGAGAGGGTGATCGGCCACACTGGGACTGAGACACGGCCCAGAC
TCCTACGGGAGGCAGCAGTAGGGAATCTTCCGCAATGGACGAAAGTCTGACGGAGCAACGCCGCGTGAGTGATGAAGGCT
TTCGGGTCGTAAAACTCTGTTGTTAGGGAAGAACAAGTACAAGAGTAACTGCTTGTACCTTGACGGTACCTAACCAGAAA
GCCACGGCTAACTACGTGCCAGCAGCCGCGGTAATACGTAGGTGGCAAGCGTTATCCGGAATTATTGGGCGTAAAGCGCG
CGCAGGCGGTTTCTTAAGTCTGATGTGAAAGCCCACGGCTCAACCGTGGAGGGTCATTGGAAACTGGGGAACTTGAGTGC
AGAAGAGAAAAGCGGAATTCCACGTGTAGCGGTGAAATGCGTAGAGATGTGGAGGAACACCAGTGGCGAAGGCGGCTTTT
TGGTCTGTAACTGACGCTGAGGCGCGAAAGCGTGGGGAGCAAACAGGATTAGATACCCTGGTAGTCCACGCCGTAAACGA
TGAGTGCTAAGTGTTAGAGGGTTTCCGCCCTTTAGTGCTGCAGCTAACGCATTAAGCACTCCGCCTGGGGAGTACGGTCG
CAAGACTGAAACTCAAAGGAATTGACGGGGGCCCGCACAAGCGGTGGAGCATGTGGTTTAATTCGAAGCAACGCGAAGAA
CCTTACCAGGTCTTGACATCCTCTGACAACTCTAGAGATAGAGCGTTCCCCTTCGGGGGACAGAGTGACAGGTGGTGCAT
GGTTGTCGTCAGCTCGTGTCGTGAGATGTTGGGTTAAGTCCCGCAACGAGCGCAACCCTTGATCTTAGTTGCCAGCATTT
AGTTGGGCACTCTAAGGTGACTGCCGGTGACAAACCGGAGGAAGGTGGGGATGACGTCAAATCATCATGCCCCTTATGAC
CTGGGCTACACACGTGCTACAATGGATGGTACAAAGGGCTGCAAGACCGCGAGGTCAAGCCAATCCCATAAAACCATTCT
CAGTTCGGATTGTAGGCTGCAACTCGCCTACATGAAGCTGGAATCGCTAGTAATCGCGGATCAGCATGCCGCGGTGAATA
CGTTCCCGGGCCTTGTACACACC

[Figure 9]

SEQ ID NO: 3: DNA sequence of protein of SANK 70214 having hydroxylation activity ATGAGTCATGCTGCGAACGTAAAAGAGAAAGTGTTAGGCTTTTTAAGTGGAAAAAGTGGAGAAAACCCGTTTCATTTATT
TGCTGAACTCCGAGATTTGGGATCGGTCGTCTCAATCCCTAACCCAATGGGTGATCCAAACAAAAATGCTTGGATGATCA
CTAAGATGGATACAGCAACAAAGGTTCTAAAGGATTCAAAACGGTTCACGGTTGATCCGGCATCGATTGAAAAGGAAAGT
GGATTTAGAGCGGAAATGGTTTCAGATCCAGATGATTCTCCCGATACCTTTTTTACAGGTAAGTCTATGGTTTTTATTGA
CGGTATTGATCATAAGCGATTGCGAATGCTCGTATCGAAAGCATTCACTCCGAAATATATGGAAGGGTTACGTCCTCGTA
TACAGGAAATAGCAGACGGTTTACTTGATCAAGTTGAATCAAAAGGTGAGATGGATCTTGTAAAAGATTACGCCTATCCT
CTACCGATTATTGTGATATCAGAAATGTTAGGAGTACCTAAAGAAGATCATGAAAATCTACAAATATGGTCATCGGCTAT
AGCTAAAGGCTTAGGCTGGGGGAAACAAGATCCAGCCGTGCAGCAGCATCTAAAAGATTTTGGAGATTACACAAAGAAGC
TTGTAGAAAAGAAAAGAGCTCATTTAGAGGATGATCTCATCAGCCAGCTGATCCAAATTGAAGAAGAGGGAGAACGTCTA
AGTGAAGAAGAGCTGATCTCGATGATTACACTTCTTATCTTTGCAGGGCATGAAACAACGTCTAACCTGATCGCTACAGG
TAGTATGATGTTATTTGACCACCCGGAGCAATTAAATAAATTAAAATCAAACCTAGATCTGGTACCAACTGCTGTTGAAG
AACTTCTGCGTTTTAACGGTCCTTCTACAACTGTAGGCCCACGTTTCGCAAAGGAAGATGTGAATATAGATGGACAAGAG
ATCAAAAAAGGAGATATGCTCCTTATCCTTGTTAAGTCAGCGAACCGAGATGAAGAAGTGTTCTCTGATTCCGAAGAATT
GGATGTCAGTCGTTCAATTCACCGACATTTAGCCTTTGGTTTTGGTATGCATATGTGCCTTGGAGCTCCTTTAGCTCGAG
TGGAAGGAGACGTCGCTTTTACAACGCTCTTAAAAAGGCTACCGAACATAGAGCTTAGTATTCCGCCTGAGGAAGTAAAG
TGGCAATTCACGCTCTCAACGCAAGGCCTTTCATCATTGCCCGTTTCATTCTAA

[Figure 10]

SEQ ID NO: 4: DNA sequence of protein of SANK 70314 having hydroxylation activity ATGAAACCGAAAGAGAAAACGGAATCGTCCGTCAAGTGAATACGATTCAAACAAAAGAAGAGCGCTTTAATCCTTTTTC
ATGGTATGAAGAGATGAGAAACAGCGCGCCTGTGCGATGGGATGAAGAAAGGCAGGTATGGGATGTTTTTCACTATGATG
GGGTCAAAGAAGTGCTGGAACAAAAAAATATTTTTTCTTCTGATCGAAGACCTCCACAAAACCAAAGACAAACTGCTCTA
GGAACGAGCCTAATTAATATTGATCCGCCTAAGCATGCTGAAATGAGAGCGCTTGTTAATAAAGCTTTTACGCCTAAAGC
AATGAAAGCATGGGAGCCTAAAAATTGCGCGCATTACCGCTGAATTATTACAAGAAGTTGAGCATCTTGAAGATATTGATA
TAGTCGAGCATCTTTCCTATCCGCTTCCGGTTATGGTAATTGCCGATATTTTAGGCGTCCCGATAGAAGATCAGCGTCAG
TTTAAAGATTGGTCGGATATTATCGTAGCGGGTCCATCGAATAATGAACGTGAAACGCTCGAAAAATTGCAGCAAGAGAA
AATGAAAGCAAACGATGAGTTAGAAACTTACTTTTATCGAATCATTGAAGAAAAGCGCACGCAGCCAGGAGATGATATTA
TTTCCGTGCTTCTTCAAGCAAAAGAAGAAGGGAAGCAGCTAACGGATGAAGAAATCGTCGGGTTTTCCATTTTGCTGCTG
ATTGCAGGCAACGAAACAACCACGAACTTAATTTCAAATACGATTTATTGTTTAATGGAAGATAAAGCTTCTTTTGAACG
ACTCAAACGAGAAAAAGAACTTTTACCTTCTGCGATTGAAGAAGTTCTTCGCTATCGTTCACCCGTTCAGGCTCTTCACC
GAATCGTAAAAAAAGATGTGGTTCTTGCAGGGAAGAAATTAAAAGCGGGCGAACACGTCGTTCCATGGATGGGATCCGCG
CACCGAGATGCGCAGTATTTTGAAGACCCGGATGTATTTCAAATCGATCGAAAGCCAAATATCCATATGGCATTTGGAAG
AGGGATTCATTTTTGCTTAGGAGCACCGCTTGCTCGAATAGAAGCAAAAGTTATGCTGGCTGAACTGATTGACCGCTATC
CGCATATGGACTGGAGCCCGGCATTTGAGTTAAAGCCGATTGAAAGCACGTTTGTGTACGGGTTAGAAGAATTATTGATT
CGTAAACATGTATAA

[Figure 11]

SEQ ID NO: 5: Amino acid sequence of protein of SANK 70214 having hydroxylation activity MSHAANVKEKVLGFLSGKSGENPFHLFAELRDLGSVVSIPNPMGDPNKNAWMITKMDTATKVLKDSKRPTVDPASIEKES
GFRAEMVSDPDDSPDTFFTGKSMVFIDGIDHKRLRMLVSKAFTPKYMEGLRPRIQEIADGLLDQVESKGEMDLVKDYAYP
LPIIVISEMLGVPKEDHENLQIWSSAIAKGLGWGKQDPAVQQHLKDFGDYTKKLVEKKRAHLEDDLISQLIQIEEEGERL
SEEELISMITLLIFAGHETTSNLIATGSMMLFDHPEQLNKLKSNLDLVPTAVEELLRFNGPSTTVGPRFAKEDVNIDGQE
IKKGDMLLILVKSANRDEEVFSDSEELDVSRSIHRHLAFGFGMHMCLGAPLARVEGDVAFTTLLKRLPNIELSIPPEEVK
WQFTLSTQGLSSLPVSF

[Figure 12]

SEQ ID NO: 6: Amino acid sequence of protein of SANK 70314 having hydroxylation activity MKTERENGIVRQVNTIQTKEERFNPFSWYEEMRNSAPVRWDEERQVWDVFHYDGVKEVLEQKNIFSSDRRPPQNQRQTAL
GTSLINIDPPKHAEMRALVNKAFTPKAMKAWEPKIARITAELLQEVEHLEDIDIVEHLSYPLPVMVIADILGVPIEDQRQ
FKDWSDIIVAGPSNNERETLEKLQQEKMKANDELETYFYRIIEEKRTQPGDDIISVLLQAKEEGKQLTDEEIVGFSILLL
IAGNETTTNLISNTIYCLMEDKASFERLKREKELLPSAIEEVLRYRSPVQALHRIVKKDVVLAGKKLKAGEHVVPWMGSA
HRDAQYFEDPDVFQIDRKPNIHMAFGRGIHFCLGAPLARIEAKVMLAELIDRYPHMDWSPAFELKPIESTFVYGLEELLI
RKHV

[Figure 13]

Phylogenetic analysis diagram of SANK 70214 and SANK 70314

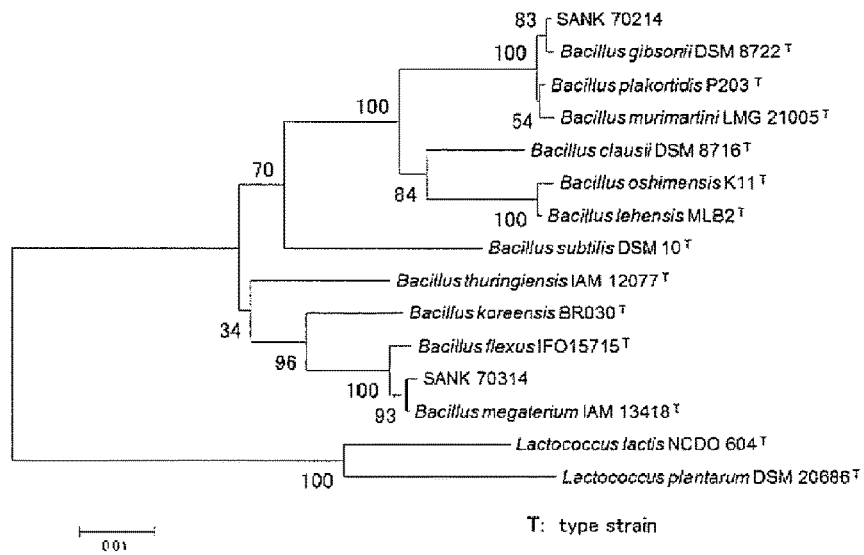

SUSTAINED-RELEASE PHARMACEUTICAL COMPOSITION FOR TREATMENT AND PREVENTION OF EYE DISEASE

TECHNICAL FIELD

The present invention relates to a pharmaceutical composition comprising, as an active ingredient, a terpenoid derivative that has the ability to activate the Keap1/Nrf2/ARE signaling pathway and is excellent in anti-inflammatory action and cytoprotective action, wherein the pharmaceutical composition exhibits a remarkable effect on the treatment and prevention of an eye disease caused by oxidative stress.

BACKGROUND ART

Upon detection of active oxygen species, etc., generated in the course of energy metabolism, host defense systems such as antioxidative enzyme groups, detoxification metabolism enzyme groups or the like are initiated. The Keap1/Nrf2/ARE signaling pathway controls the initiation of this host defense system.

It is known that the activation of the Keap1/Nrf2/ARE signaling pathway induces its target gene of NAD(P)H: quinone oxidoreductase-1 (NQO1), heme oxygenase-1 (HO-1), γ-glutamate cysteine ligase catalytic subunit (GCLC), or the like (Non-patent Literature 1). NQO1 is a phase 2 enzyme of xenobiotic metabolism and is important for detoxification. HO-1 and GCLC are known as typical antioxidative enzymes. When these enzymes are increased in amount or activated, the cells become resistant to poison, oxidative stress, inflammation, etc. Compounds that activate this signaling pathway are therefore considered to serve as therapeutic drugs for various diseases (Non-patent Literatures 2 to 5). Specific examples of the targeted diseases are as given below.

Nrf2-deficient mice have been reported to exhibit vulnerability in the retinal ischemia/reperfusion system (Non-patent Literature 6). This suggests the applicability to the compounds to eye diseases such as allergic conjunctival disease, viral conjunctivitis, pterygium, corneal infection, corneal endothelial disorder, cataract, uveitis, Behcet's disease, diabetic retinopathy, retinal detachment, retinal vein occlusion, central serous chorioretinopathy, age-related macular degeneration, diabetic macular edema, macular disease, retinitis pigmentosa, glaucoma, and cataract (Non-patent Literatures 7 and 8).

Nrf2-deficient mice have been reported to exhibit vulnerability to cisplatin-induced nephrotoxicity (Non-patent Literature 9). This suggests the applicability of the compounds to renal diseases such as acute nephritis, chronic nephritis, acute renal failure, chronic renal failure, nephrotic syndrome, IgA nephropathy, diabetic nephropathy, gouty kidney, nephrosclerosis, hydronephrosis, tubulointerstitial nephritis, and urinary tract infection (Non-patent Literature 10).

Nrf2-deficient mice have been reported to exhibit vulnerability to cigarette smoke exposure (Non-Patent Literature 11). This suggests the applicability of the compounds to respiratory diseases such as bronchitis, pneumonia, pleuritis, chronic obstructive pulmonary disease, diffuse panbronchiolitis, pulmonary emphysema, and asthma (Non-patent Literatures 12 and 13).

Nrf2-deficient mice have been reported to be likely to develop non-alcoholic steatohepatitis when fed with methionine/choline-deficient diet (Non-patent Literature 14). This suggests the applicability of the compounds to hepatic diseases such as alcoholic fatty liver, non-alcoholic steatohepatitis, hepatic fibrosis, and liver cirrhosis (Non-patent Literatures 2 and 15).

Also, Nrf2 activators have been reported to exhibit hypoglycemic action in mice (Non-patent Literature 16). This suggests the applicability of the compounds to diabetes mellitus and its complications (diabetic retinopathy, diabetic nephropathy, and diabetic neuropathy) or the like.

As substances that activate the Keap1/Nrf2/ARE signaling pathway, sulforaphane contained in broccoli sprouts, curcumin contained in turmeric for curry, or the like have been reported to activate Nrf2 and promote the detoxification of carcinogens (Non-patent Literature 17). Also, a 5-membered ring triterpenoid comprising methyl 2-cyano-3,12-dioxooleana-1,9(11)-dien-28-acid (Non-patent Literature 18 and Patent Literatures 1 to 10) discovered by Honda et al. has been reported to activate the Keap1/Nrf2/ARE signaling pathway. These compounds have been reported to bring about the production of several anti-inflammatory proteins and antioxidative proteins (e.g., NQO1, HO-1, and GCLC) (Patent Literature 9).

Meanwhile, pharmaceutical compositions in various forms such as nanoparticles, microspheres, and rods using various base materials have been designed for the purpose of maximizing the pharmacological effect of the compound having antioxidative action as described above on posterior eye diseases while reducing the burden of administration on patients. Also, studies have been made on the exploitation of various DDS techniques such as iontophoresis and microneedles (Non-Patent Literature 19). This indicates that there is an exceedingly high need for special administration methods for achieving drug delivery to affected areas, drug retention and sustention, and drug effectiveness in the field of eye diseases. Possible materials are metals, non-degradable plastics, and biodegradable plastics, and possible forms are various forms such as microspheres and rods. Polylactic acid or poly(lactic-co-glycolic acid) is a base material having excellent biocompatibility and biodegradability (Non-Patent Literature 20). Since there exist some pharmaceutical products having this base material as a component, practical use of this base material has been evidently established. The microsphere or rod form is a shape suitable for intravitreal administration as an implant.

Although active ingredients (drugs) and various DDS techniques for the prevention or treatment of posterior eye diseases have been designed as described above, drugs having properties compatible with DDS techniques have been found in very rare cases. As for combinations of drugs and DDS techniques, only a few articles have been launched as pharmaceutical products, and in the field of eye diseases there exists only an implant injection of dexamethasone. This difficulty is caused by various factors, however, in many cases, it is presumably attributed to such an insufficient dose that it is not easy to enable one dose to include the drug in a sufficient amount necessary for the period required for sustention.

Accordingly, there has been a demand for the development of a compound having excellent preventive and therapeutic effects on a posterior eye disease, and a pharmaceutical composition for a posterior eye disease, containing the compound as an active ingredient and being capable of exerting its preventive and therapeutic effects at long dosing intervals acceptable in medical practice.

CITATION LIST

Patent Literature

Patent Literature 1: WO99/65478
Patent Literature 2: WO2012/125488
Patent Literature 3: WO2011/130302
Patent Literature 4: WO2009/146216
Patent Literature 5: WO2009/129546
Patent Literature 6: WO2009/129548
Patent Literature 7: WO2009/023232
Patent Literature 8: WO2004/064723
Patent Literature 9: WO2009/089545
Patent Literature 10: WO2013/188818

Non-Patent Literature

Non-Patent Literature 1: Int. J. Biochem. Cell. Biol. 2012; 44: 1315-1320
Non-Patent Literature 2: Clin. Pharmacol. Ther. 2012; 92: 340-348
Non-Patent Literature 3: Adv. Pharmacol. 2012; 63: 43-79
Non-Patent Literature 4: Med. Res. Rev. 2012; 32: 687-726
Non-Patent Literature 5: Mol. Aspects. Med. 2011; 32: 234-246
Non-Patent Literature 6: Free Radic Biol. Med. 2011; 51: 216-224
Non-Patent Literature 7: Front Biosci. (Elite Ed.) 2012; 4: 141-115
Non-Patent Literature 8: Curr. Med. Chem. 2011; 18: 931-942
Non-Patent Literature 9: J. Pharmacol. Exp. Ther. 2010; 335: 2-12
Non-Patent Literature 10: Int. J. Nephrol. 2012; 321714
Non-Patent Literature 11: Proc. Natl. Acad. Sci. USA 2009; 106: 250-255
Non-Patent Literature 12: Trends Mol. Med. 2011; 17: 363-371
Non-Patent Literature 13: Toxicol. Appl. Pharmacol. 2010; 244: 43-56
Non-Patent Literature 14: Free Radic Biol. Med. 2010; 48: 357-371
Non-Patent Literature 15: J. Nutr. Biochem. 2012; 23: 1201-1206
Non-Patent Literature 16: J. Biol. Chem. 2010; 285: 40581-40592
Non-Patent Literature 17: The Journal of The Japanese Biochemical Society, 2009; 81: 447-9
Non Patent Literature 18: Bioorg. Med. Chem. Lett., 1998; 8: 2711-2714
Non-Patent Literature 19: Drug Discovery Today 2011; 16: 1-8
Non-Patent Literature 20: Advanced Drug Delivery Reviews 2013; 65: 104-120

SUMMARY OF INVENTION

Technical Problem

The present inventors have conducted diligent studies on compounds that activate the Keap1/Nrf2/ARE signaling pathway and are useful for the prevention and treatment of a posterior eye disease, and pharmaceutical compositions comprising the compounds as an active ingredient, and consequently completed the present invention by finding that specific terpenoid derivatives have an excellent anti-inflammatory action and cytoprotective action and finding that a specific pharmaceutical composition containing the compound as an active ingredient is capable of exerting its preventive and therapeutic effects at long dosing intervals acceptable in medical practice.

Solution to Problem

Specifically, the present invention provides
(1) a terpenoid derivative represented by the following formula (I):

[Formula 1]

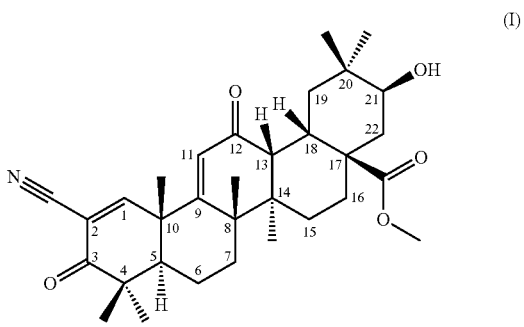

(2) a terpenoid derivative having the following physicochemical properties:
1) appearance: a colorless powdery substance
2) molecular formula: $C_{32}H_{43}NO_5$
3) molecular weight: 521 (measured by ESI mass spectrometry)
4) the accurate mass, $[M+H]^+$, measured by high-resolution LC-ESI mass spectrometry is as given below:
found: 522.32062
calculated: 522.32140
5) $^1$H-nuclear magnetic resonance spectra: the $^1$H-nuclear magnetic resonance spectra (500 MHz) measured in deuterated chloroform referenced to 0.00 ppm using TMS are as given below:
σ: 0.98 (3H, s), 0.99 (3H, s), 1.00 (3H, s), 1.17 (3H, s), 1.18-1.22 (1H, m), 1.25 (3H, s), 1.28-1.30 (1H, m), 1.33 (3H, s), 1.49 (3H, s), 1.51-1.55 (1H, m), 1.62-1.66 (1H, m), 1.68-1.71 (1H, m), 1.69-1.72 (1H, m), 1.70-1.80 (2H, m), 1.77-1.79 (1H, m), 1.76-1.82 (2H, m), 1.85-1.89 (2H, m), 2.96 (1H, d, J=5.0 Hz), 3.04 (1H, ddd, J=4.0 Hz, 4.0 Hz, 14.0 Hz), 3.49 (1H, dd, J=5.0 Hz, 11.5 Hz), 3.71 (3H, s), 5.97 (1H, s), 8.03 (1H, s) ppm.
6) $^{13}$C-nuclear magnetic resonance spectra: the $^{13}$C-nuclear magnetic resonance spectra (125 MHz) measured in deuterated chloroform referenced to 0.00 ppm using TMS are as given below:
σ: 16.4 (q), 18.2 (t), 21.4 (q), 21.5 (q), 23.9 (t), 24.6 (q), 26.6 (q), 27.0 (q), 28.1 (t), 29.1 (q), 31.1 (d), 31.6 (t), 35.8 (t), 35.9 (s), 40.1 (t), 42.0 (s), 42.5 (s), 45.0 (s), 45.7 (s), 47.7 (d), 48.9 (s), 49.0 (d), 52.1 (q), 73.7 (d), 114.3 (s), 114.6 (s), 124.0 (d), 165.5 (d), 168.5 (s), 176.6 (s), 196.5 (s), 198.7 (s) ppm.
7) high-performance liquid chromatography:
column: Unison UK-C18
(4.6 mm in diameter×75 mm in length; manufactured by Imtakt Corp.)
solvent: A: 10 mM aqueous ammonium formate solution containing 0.01% formic acid B: acetonitrile containing 0.01% formic acid
A/B=equilibration with 5/5 followed by linear gradient for 7 minutes up to A/B=1/9
flow rate: 1.0 ml/min
temperature: 40° C.
detection: ultraviolet absorption λ=230 nm
retention time: 4.3 minutes, (3) a terpenoid derivative represented by the following formula (II):

[Formula 2]

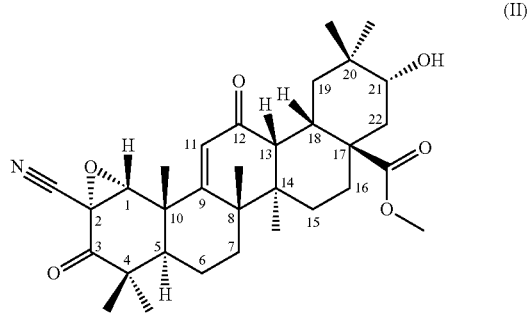

(4) a terpenoid derivative having the following physico-chemical properties:
1) appearance: a colorless powdery substance
2) molecular formula: $C_{32}H_{43}NO_6$
3) molecular weight: 537 (measured by ESI mass spectrometry)
4) the accurate mass, $[M+H]^+$, measured by high-resolution LC-ESI mass spectrometry is as given below:
found: 538.31496
calculated: 538.31631
5) $^1$H-nuclear magnetic resonance spectra: the $^1$H-nuclear magnetic resonance spectra (500 MHz) measured in deuterated chloroform referenced to 0.00 ppm using TMS are as given below:
σ: 0.96 (3H, s), 1.06 (3H, s), 1.11 (3H, s), 1.12 (3H, s), 1.19 (3H, s), 1.27 (3H, s), 1.28 (3H, s), 1.46 (1H, d, J=13.0 Hz), 1.47 (1H, d, J=13.0 Hz), 1.52-1.59 (2H, m), 1.61-1.65 (2H, m), 1.66-1.69 (1H, m), 1.68-1.75 (1H, m), 1.75 (1H, dd, J=3.5 Hz, 14.5 Hz), 1.88 (1H, brd, J=14.5 Hz), 1.98 (1H, dd, J=5.5 Hz, 9.5 Hz), 2.03 (1H, dd, J=3.5 Hz, 14.5 Hz), 2.38 (1H, ddd, J=3.5 Hz, 14.0 Hz, 14.0 Hz), 2.99 (1H, d, J=4.5 Hz), 3.10 (1H, brd, J=13.5 Hz), 3.53 (1H, brs), 3.69 (3H, s), 4.34 (1H, s), 6.09 (1H, s) ppm.
6) $^{13}$C-nuclear magnetic resonance spectra: the $^{13}$C-nuclear magnetic resonance spectra (125 MHz) measured in deuterated chloroform referenced to 0.00 ppm using TMS are as given below:
σ: 18.3 (t), 21.0 (q), 21.3 (q), 22.8 (q), 23.9 (q), 24.0 (q), 25.7 (t), 27.4 (q), 28.0 (q), 28.7 (t), 30.0 (t), 31.4 (t), 31.5 (d), 35.2 (s), 38.9 (t), 40.9 (s), 42.1 (s), 42.6 (d), 45.1 (s), 45.5 (s), 47.0 (s), 49.5 (d), 52.0 (q), 53.2 (s), 69.1 (d), 74.8 (d), 113.6 (s), 124.8 (d), 168.8 (s), 177.6 (s), 198.8 (s), 202.4 (s) ppm.
7) high-performance liquid chromatography:
column: Unison UK-C18
(4.6 mm in diameter×75 mm in length; manufactured by Imtakt Corp.)
solvent: A: 10 mM aqueous ammonium formate solution containing 0.01% formic acid
B: acetonitrile containing 0.01% formic acid
A/B=equilibration with 5/5 followed by linear gradient for 7 minutes up to A/B=1/9
flow rate: 1.0 ml/min
temperature: 40° C.
detection: ultraviolet absorption λ=230 nm
retention time: 5.4 minutes, (5) a method for producing a compound according to (1) or (2), comprising using a compound represented by the following formula (1):

[Formula 3]

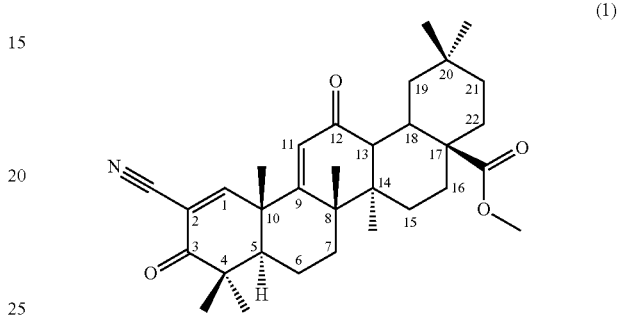

as a substrate, culturing together with this compound in a medium a strain for biotransformation of the genus *Chaetomium* capable of transforming the compound to the compound according to (1) or (2), and collecting the compound according to (1) or (2) from the culture, (6) the method for producing a compound according to (5), wherein the strain for biotransformation is *Chaetomium globosum* SANK 10312 (Deposition No. NITE BP-1486) belonging to the genus *Chaetomium*, (7) the method for producing a compound according to (5), wherein the strain for biotransformation is *Chaetomium* sp. SANK 11867 (Deposition No. NITE BP-01916) belonging to the genus *Chaetomium*, (8) a method for producing a terpenoid derivative represented by the following formula (III):

[Formula 4]

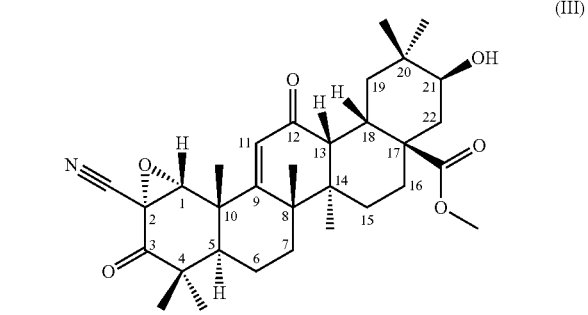

comprising using a compound represented by the formula (1) as a substrate, culturing together with this compound in a medium *Chaetomium* sp. SANK 11867 (Deposition No. NITE BP-01916) belonging to the genus *Chaetomium* capable of transforming the compound to the terpenoid derivative represented by the formula (III), and collecting the terpenoid derivative represented by the formula (III) from the culture, (9) a method for producing a compound according to (3) or (4) or a terpenoid derivative represented by the formula (III), comprising producing a compound represented by the following formula (2):

[Formula 5]

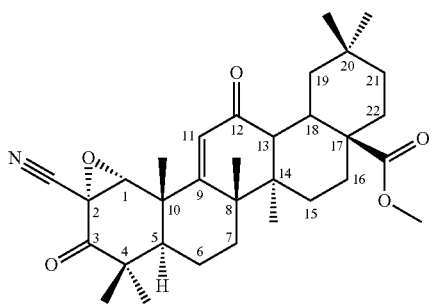

(2)

from a compound of the formula (1) through an epoxidation reaction using an organic peroxide,
subsequently using the compound represented by the formula (2) as a substrate, culturing together with this compound in a medium a strain for biotransformation capable of transforming the compound to the compound according to (3) or (4) or the terpenoid derivative represented by the formula (III), and collecting the compound according to (3) or (4) or the terpenoid derivative represented by the formula (III) from the culture,

(10) the method according to (9), wherein the strain for biotransformation is *Bacillus* sp. SANK 70214 (Deposition No. NITE BP-01914) belonging to the genus *Bacillus*,

(11) the method according to (9), wherein the strain for biotransformation is *Bacillus megaterium* SANK 70314 (Deposition No. NITE BP-01915) belonging to the genus *Bacillus*,

(12) the method according to (9), wherein the strain for biotransformation is a transformant obtained by transformation of a host with a gene encoding the following protein (a), (b), (c), (d), or (e):
(a) a protein having the amino acid sequence of SEQ ID NO: 5 (FIG. 11),
(b) a protein having the amino acid sequence of SEQ ID NO: 6 (FIG. 12),
(c) a protein having an amino acid sequence derived from the amino acid sequence of the protein (a) or (b) by the deletion, substitution, insertion, or addition of one or several amino acids,
(d) a protein having an amino acid sequence having 90% or higher sequence identity to the amino acid sequence of the protein (a) or (b), and
(e) a protein encoded by DNA hybridizing under stringent conditions to DNA consisting of a nucleotide sequence encoding the protein (a) or (b),

(13) the method according to (12), wherein the host is *Escherichia coli* or a bacterium,

(14) the method according to (13), wherein the bacterium is *Bacillus subtilis*,

(15) a nucleotide sequence having any of the following nucleotide sequences (f) to (j) and encoding a protein having hydroxylase activity against a substrate compound represented by the formula (2):
(f) the nucleotide sequence described in SEQ ID NO: 3 (FIG. 9),
(g) the nucleotide sequence described in SEQ ID NO: 4 (FIG. 10),
(h) the nucleotide sequence of DNA hybridizing under stringent conditions to DNA comprising a complementary sequence of any nucleotide sequence defined in the nucleotide sequence (f) or (g),
(i) a nucleotide sequence having 90% or higher identity to any nucleotide sequence defined in the nucleotide sequence (f) or (g), and
(j) a nucleotide sequence which does not hybridize under stringent conditions to DNA comprising a complementary sequence of any nucleotide sequence defined in the nucleotide sequence (f) or (g) due to the degeneracy of the genetic code, but encodes the same amino acid sequence as the nucleotide sequence defined in any of (f) to (h),

(16) a protein having any of the following amino acid sequences (k) to (n) and having hydroxylase activity against a substrate compound represented by the formula (2):
(k) the amino acid sequence described in SEQ ID NO: 5 (FIG. 11),
(l) the amino acid sequence described in SEQ ID NO: 6 (FIG. 12),
(m) an amino acid sequence derived from any amino acid sequence defined in the amino acid sequence (k) or (l) by the deletion, substitution, and/or addition of one or several amino acids, and
(n) an amino acid sequence having 90% or higher identity to any amino acid sequence defined in the amino acid sequence (k) or (l),

(17) an autonomously replicating or integratively replicating recombinant plasmid carrying a nucleotide sequence according to (15),

(18) a transformant obtained by the transformation of a host with a recombinant plasmid according to (17),

(19) a transformant *Bacillus subtilis* SANK 70214T obtained by the transformation of *Bacillus subtilis* with a recombinant plasmid according to (17),

(20) a transformant *Bacillus subtilis* SANK 70314T obtained by the transformation of *Bacillus subtilis* with a recombinant plasmid according to (17),

(21) *Bacillus* sp. SANK 70214 (Deposition No. NITE BP-01914) belonging to the genus *Bacillus*,

(22) *Bacillus megaterium* SANK 70314 (Deposition No. NITE BP-01915) belonging to the genus *Bacillus*,

(23) a pharmaceutical drug for treatment or prevention of
an eye disease (the eye disease is allergic conjunctival disease, viral conjunctivitis, pterygium, corneal infection, dry eye, corneal disorder (which is corneal epithelial disorder and/or corneal endothelial disorder), uveitis, Behcet's disease, diabetic retinopathy, retinal detachment, retinal vein occlusion, central serous chorioretinopathy, age-related macular degeneration, diabetic macular edema, macular disease, retinitis pigmentosa, glaucoma, or cataract),
a renal disease (the renal disease is acute nephritis, chronic nephritis, acute renal failure, chronic renal failure, nephrotic syndrome, IgA nephropathy, diabetic nephropathy, gouty kidney, nephrosclerosis, hydronephrosis, tubulointerstitial nephritis, decreased renal function after coronary-artery bypass surgery, or urinary tract infection),
a respiratory disease (the respiratory disease is bronchitis, pneumonia, pleuritis, chronic obstructive pulmonary disease, acute lung injury (ALI), diffuse panbronchiolitis, pulmonary emphysema, or asthma),
a hepatic disease (the hepatic disease is alcoholic fatty liver, non-alcoholic steatohepatitis, hepatic fibrosis, liver cirrhosis, or hepatic dysfunction associated with liver transplantation), a brain disease (the brain disease is Alzheimer's disease, Parkinson's disease, Huntington's disease, amyotrophic lateral sclerosis (ALS), cerebral infarction, or multiple sclerosis), or a heart disease (the heart disease is myocardial infarction), comprising a terpenoid derivative according to any one of (1) to (4) as an active ingredient,

(24) a sustained-release pharmaceutical composition for the treatment or prevention of an eye disease, comprising a terpenoid derivative according to any one of (1) to (4) or a terpenoid derivative represented by the formula (III) as an active ingredient, wherein the sustained-release pharmaceutical composition maintains a pharmacological action thereof for 1 week or longer by the sustained release of the terpenoid derivative under physiological conditions and has a base material administrable to the vitreous body and a form administrable to the vitreous body,

(25) a sustained-release pharmaceutical composition for the treatment or prevention of an eye disease, comprising a terpenoid derivative represented by the formula (III) as an active ingredient, wherein the sustained-release pharmaceutical composition maintains a pharmacological action thereof for 1 week or longer by the sustained release of the terpenoid derivative under physiological conditions and has a base material administrable to the vitreous body and a form administrable to the vitreous body,

(26) the sustained-release pharmaceutical composition for the treatment or prevention of an eye disease according to (24) or (25), wherein the base material is a biodegradable polymer,

(27) the sustained-release pharmaceutical composition for the treatment or prevention of an eye disease according to (24) or (25), wherein the base material is polylactic acid or poly(lactic-co-glycolic acid),

(28) the sustained-release pharmaceutical composition for the treatment or prevention of an eye disease according to any one of (24) to (27), wherein the form is microspheres,

(29) the sustained-release pharmaceutical composition for the treatment or prevention of an eye disease according to any one of (24) to (27), wherein the form is a rod,

(30) the sustained-release pharmaceutical composition for the treatment or prevention of an eye disease according to any one of (24) to (29), wherein the content of the active ingredient is 5% by weight to 80% by weight,

(31) the sustained-release pharmaceutical composition for the treatment or prevention of an eye disease according to any one of (24) to (29), wherein the content of the active ingredient is 20% by weight to 60% by weight,

(32) the sustained-release pharmaceutical composition for the treatment or prevention of an eye disease according to (24) or (25), wherein the content of the active ingredient is 20% by weight to 60% by weight, the sustained-release pharmaceutical composition maintains a pharmacological action thereof for 1 week or longer by the sustained release of the active ingredient under physiological conditions, the base material is polylactic acid or poly(lactic-co-glycolic) acid, and the shape is a microsphere or a rod,

(33) the sustained-release pharmaceutical composition for the treatment or prevention of an eye disease according to any one of (24) to (32), wherein the eye disease is age-related macular degeneration, and (34) the sustained-release pharmaceutical composition for the treatment or prevention of an eye disease according to any one of (24) to (32), wherein the eye disease is diabetic macular edema and/or retinal vein occlusion.

The terpenoid derivatives (I), (II), and (III) of the present invention (hereinafter, these compounds are also collectively referred to as the terpenoid derivative of the present invention) may form a solvate. Also, the terpenoid derivative of the present invention, when left in air, may have adsorbed water or form a hydrate by absorbing moisture. Such a solvate or hydrate is also included in the present invention.

Advantageous Effects of Invention

The terpenoid derivative of the present invention is excellent in anti-inflammatory action and cytoprotective action and is useful as a therapeutic drug for an eye disease, a renal disease, a respiratory disease, a hepatic disease, and diabetes mellitus and its complications, particularly, an eye disease.

The sustained-release pharmaceutical composition of the present invention comprising the terpenoid derivative of the present invention as an active ingredient can maintain a pharmacological action thereof for 1 week or longer by one dose. The sustained-release pharmaceutical composition of the present invention is capable of exerting its effects at long dosing intervals acceptable in medical practice aimed at preventing and treating of a posterior eye disease and is therefore useful as a sustained-release pharmaceutical composition for the treatment or prevention of an eye disease.

The production method of the present invention using the strain for biotransformation of the present invention can synthesize the terpenoid derivative of the present invention from a substrate with a high rate of biotransformation.

BRIEF DESCRIPTION OF DRAWINGS

FIG. 1 shows the $^1$H-NMR spectra of terpenoid derivative (I).

FIG. 2 shows the $^1$H-$^{13}$C HSQC spectra of terpenoid derivative (I).

FIG. 3 shows the $^1$H-$^1$H NOESY spectra of terpenoid derivative (I).

FIG. 4 shows the $^1$H-NMR spectra of terpenoid derivative (II).

FIG. 5 shows the $^1$H-$^{13}$C HSQC spectra of terpenoid derivative (II).

FIG. 6 shows the $^1$H-$^1$H NOESY spectra of terpenoid derivative (II).

FIG. 7 shows the partial nucleotide sequence of SANK 70214 16S rDNA (SEQ ID NO: 1).

FIG. 8 shows the partial nucleotide sequence of SANK 70314 16S rDNA (SEQ ID NO: 2).

FIG. 9 shows the DNA sequence of a protein of SANK 70214 (SEQ ID NO: 3) having hydroxylation activity.

FIG. 10 shows the DNA sequence of a protein of SANK 70314 (SEQ ID NO: 4) having hydroxylation activity.

FIG. 11 shows the amino acid sequence of the protein of SANK 70214 (SEQ ID NO: 5) having hydroxylation activity.

FIG. 12 shows the amino acid sequence of the protein of SANK 70314 (SEQ ID NO: 6) having hydroxylation activity.

FIG. 13 shows the phylogenetic tree of SANK 70214 and SANK 70314.

DESCRIPTION OF EMBODIMENTS

The terpenoid derivative of the present invention can be isolated and purified according to a routine method from cultures of a microbe having the ability to transform a specific substrate compound to the terpenoid derivative of the present invention [in the present invention, referred to as a strain for biotransformation].

1. Substrate Compound (1) A compound represented by the following formula (1) can be used as a substrate for the production of the terpenoid derivative represented by the formula (I) (hereinafter, referred to as terpenoid derivative (I)) and the terpenoid derivative represented by the formula (III) (hereinafter, referred to as terpenoid derivative (III)) of the present invention.

[Formula 6]

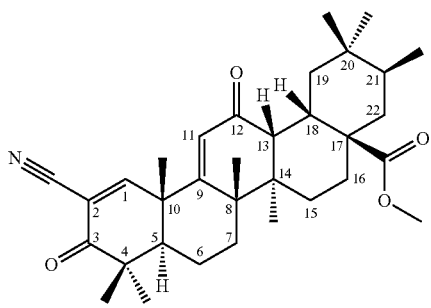

(1)

The compound is described as compound No. 17 in Synthesis Scheme 2 in Bioorganic & Medicinal Chemistry Letters 8 (1998) 2711-2714 and is also referred to as methyl 2-cyano-3,12-dioxooleana-1,9-dien-28-oate (CDDO-Me). Hereinafter, the substrate compound is also referred to as CDDO-Me.

CDDO-Me can be produced according to a synthesis method described in Bioorganic & Medicinal Chemistry Letters 7 (1997) 1623-1628 and Bioorganic & Medicinal Chemistry Letters 8 (1998) 2711-2714.

(2) A compound represented by the following formula (2) can be used as a substrate for the production of the terpenoid derivative represented by the formula (II) (hereinafter, referred to as terpenoid derivative (II)) and the terpenoid derivative represented by the formula (III) of the present invention.

[Formula 7]

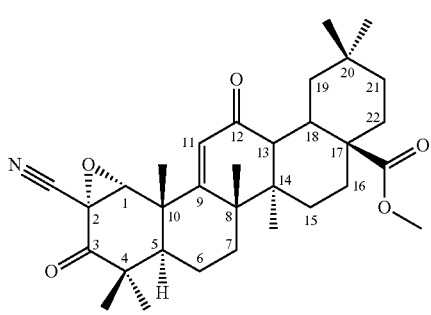

(2)

The compound represented by the formula (2) can be produced from CDDO-Me through an epoxidation reaction using an organic peroxide. Examples of the organic peroxide can include, but are not particularly limited to, performic acid, peracetic acid, perbenzoic acid, and 3-chloroperbenzoic acid. 3-Chloroperbenzoic acid is preferred.

2. Strain for Biotransformation Used for Production of Terpenoid Derivative of Present Invention from Substrate Compound (1) <SANK 10312>

The strain for biotransformation used for the production of terpenoid derivative (I) or terpenoid derivative (III) of the present invention from the substrate compound (1) is not particularly limited and is preferably a fungus. Examples thereof include a fungus belonging to the genus *Chaetomium*.

The fungus belonging to the genus *Chaetomium* is preferably *Chaetomium globosum*, more preferably *Chaetomium globosum* SANK 10312 (Deposition No. NITE BP-1486) (hereinafter, this strain is referred to as "SANK 10312").

SANK 10312 was separated from fresh water of Kyoto prefecture in November 2000.

In order to identify the fungal strains SANK 10312, the following 4 types of media were used, and their compositions were as follows:

<PDA Medium (Potato Dextrose Agar Medium)>

| | |
|---|---|
| Nissui potato dextrose agar medium (manufactured by Nissui Pharmaceutical Co., Ltd.) | 39 g |
| Distilled water | 1000 ml |

<OA medium (oatmeal agar medium)>

| | |
|---|---|
| Oatmeal extract* | 1000 ml |
| Agar | 20 g |

*To 30 g of oatmeal, distilled water was added, and the mixture was decocted for insomuch as 2 hours and filtered through cloth, followed by fill-up to 1000 ml to prepare the oatmeal extract.

<MEA medium (malt extract agar medium)>

| | |
|---|---|
| Bacto Malt Extract (manufactured by Becton, Dickinson and Company) | 30 g |
| Bacto Soytone (manufactured by Becton, Dickinson and Company) | 3 g |
| Agar | 15 g |
| Distilled water | 1000 ml |

<CMA medium (corn meal agar medium)>

| | |
|---|---|
| Corn meal agar "Nissui" (manufactured by Nissui Pharmaceutical Co., Ltd.) | 17 g |
| Distilled water | 1000 ml |

In the description below, the color is indicated according to Kornerup, A. & Wanscher, J. H. 1978. Methuen handbook of colour (3rd. edition). Erye Methuen, London.

The mycological properties of SANK 10312 are as given below.

SANK 10312 was inoculated to 4 types of media (PDA medium, OA medium, CMA medium, and MEA medium), and its mycological properties were observed.

The growth temperature of SANK 10312 in the PDA medium was 9 to 33° C., and this strain grew well, particularly, at 18 to 31° C.

The mycological properties of SANK 10312 are as follows:

The colonies in the OA medium are 80 mm or larger in diameter by culture at 28° C. for 10 days. The colonies are thin and composed of white and short cottony hyphae, and are grayish-yellow with grayish brown to yellowish brown concentrically at a site slightly distant from the center. The central portion of the colony densely forms small granular ascomata on the surface and is dark green. The reverse side is pale yellow to brownish orange with an olive brown color at the central portion and a dark brown color concentrically at a site slightly distant from the center.

The colonies in the MEA medium are 80 mm or larger in diameter by culture at 28° C. for 10 days. The colonies are thin and composed of white and short cottony hyphae, and are brownish orange. Neither conidia nor ascomata are formed. The reverse side is similar thereto.

The colonies in the CMA medium are 60 mm in diameter by culture at 28° C. for 10 days. The colonies are very thin and merely have sparse hyphae on the surface of the agar. The surface color of the colony is almost colorless and clear, and the reverse side is similar thereto.

The growth temperature of SANK 10312 in the PDA medium is 9 to 33° C., and this strain grows well, particularly, at 18 to 31° C.

The microscopic structure of SANK 10312 in the OA medium at day 10 at 28° C. is as follows:

The ascomata are dark brown to black, have subspherical to oval shape of 175 to 240 µm in width and 275 to 400 µm in height, and have a peridium composed of textura intricata and an ostiole at the apex. The lateral hairs are straight or slightly wavy, pale olive, and 3.5 µm or smaller in diameter, and are integrated with terminal hairs in the upper region of the ascomata. A large number of terminal hairs are dense and wavy or loosely coiled toward the tip and have rough surface as a whole, have septa, and a round tip. The terminal hairs are 3 to 4 µm in basal width and olive and become thinner and lighter toward the tip. The asci are club-shaped and octosporous. The ascospores are lemon-shaped and are light brown when immature and pale green to dark olive brown and 6.0 to 9.0×8.0 to 11.0 µm when mature. No conidia are observed.

The mycological features as mentioned above are well consistent with the description about *Chaetomium globosum* Kunze in Compendium of Soil Fungi (K. H. Domsch, W. Gams and T.-H. Anderson (2007)). Thus, this fungal strain was identified as *Chaetomium globosum* and designated as *Chaetomium globosum* SANK 10312.

SANK 10312 was internationally deposited under Deposition No. NITE BP-1486 with NITE Patent Microorganisms Depositary (NPMD), Biological Resource Center, National Institute of Technology and Evaluation (address: 2-5-8 Kazusakamatari, Kisarazu-shi, Chiba, Japan) on Dec. 18, 2012.

As is well known, fungi are susceptible to mutation in the natural world or by artificial operation (e.g., ultraviolet irradiation, radiation, or chemical agent treatment). Presumably, SANK 10312 of the present invention is also susceptible to such mutation. In the present invention, SANK 10312 encompasses all of their variants.

These variants also encompass those obtained by a genetic method, for example, recombination, transduction, or transformation.

Specifically, SANK 10312 as the strain for biotransformation used for the production of the terpenoid derivative of the present invention, their variants, and fungal strains that are not clearly distinguished therefrom are all included in SANK 10312.

(2)<SANK 11867>

The strain for biotransformation used for the production of terpenoid derivative (I) or terpenoid derivative (III) of the present invention from substrate compound (1) is not particularly limited and is preferably a fungus. Examples thereof can include a fungus belonging to the genus *Chaetomium*.

The fungus belonging to the genus *Chaetomium* is preferably *Chaetomium* sp., more preferably *Chaetomium* sp. SANK 11867 (Deposition No. NITE BP-01916) (this strain is referred to as "SANK 11867").

SANK 11867 separated from soil in Japan is a stock strain of our company.

In order to identify the fungal strain SANK 11867, 4 types of media (PDA medium, OA medium, MEA medium, and CMA medium) used for the identification of the fungal strain SANK 10312 were used.

In the description below, the color is indicated according to "Methuen handbook of colour".

The mycological properties of SANK 11867 are as given below.

SANK 11867 was inoculated to 4 types of media (PDA medium, OA medium, CMA medium, and MEA medium), and its mycological properties were observed.

The growth temperature of SANK 11867 in the PDA medium was 5 to 33° C., and this strain grew well, particularly, at 13 to 31° C.

The mycological properties of SANK 11867 are as follows:

The colonies in the OA medium at day 10 at 20° C. are 80 mm or larger in diameter. The colonies are thin and composed of white and short cottony hyphae, and are grayish-yellow. The central portion of the colony densely forms small granular ascomata on the surface and is dark green. The reverse side has the same color as that of the surface.

The colonies in the MEA medium at day 10 at 20° C. are 80 mm or larger in diameter. The colonies are thin and composed of white and short cottony hyphae, and are brownish orange. Neither conidia nor ascomata are formed. The reverse side is similar thereto.

The colonies in the CMA medium at day 10 at 20° C. are 52 to 55 mm in diameter. The colonies are very thin and merely have sparse hyphae on the surface of the agar. The surface color of the colony is almost colorless and clear, and the reverse side is similar thereto.

The microscopic structure of SANK 11867 in the OA medium at day 10 at 20° C. is as follows:

The ascomata are dark brown to black, have subspherical to oval shape of 145 to 350 µm in width and 225 to 625 µm in height, and have a peridium composed of textura *intricata* and an ostiole at the apex. The lateral hairs are straight or slightly wavy, pale olive and are integrated with terminal hairs in the upper region of the ascomata. A large number of terminal hairs are dense and wavy or loosely coiled toward the tip and have rough surface as a whole, have septa, and a round tip. The terminal hairs are 2.5 to 6.5 µm in basal width and olive and become thinner and lighter toward the tip. The asci are club-shaped and octosporous. The ascospores are lemon-shaped and are light brown when immature and pale green to dark olive brown and 8.5 to 10.5×7.0 to 8.5 µm when mature. No conidia are observed.

The mycological features as mentioned above are well consistent with the description about the genus *Chaetomium* in Compendium of Soil Fungi (K. H. Domsch, W. Gams and T.-H. Anderson (2007)). Thus, this fungal strain was identified as *Chaetomium* sp. and designated as *Chaetomium* sp. SANK 11867.

SANK 11867 was internationally deposited under Deposition No. NITE BP-01916 with NITE Patent Microorganisms Depositary (NPMD), Biological Resource Center, National Institute of Technology and Evaluation (address: 2-5-8 Kazusakamatari, Kisarazu-shi, Chiba, Japan) on Aug. 7, 2014.

As is well known, microbes are susceptible to mutation in the natural world or by artificial operation (e.g., ultraviolet irradiation, radiation, or chemical agent treatment). Presumably, SANK 11867 of the present invention is also susceptible to such mutation. In the present invention, SANK 11867 encompasses all of its variants.

These variants also encompass those obtained by a genetic method, for example, recombination, transduction, or transformation.

Specifically, SANK 11867 as the strain for biotransformation used for the production of the terpenoid derivative of the present invention, its variants, and fungal strains that are not clearly distinguished therefrom are all included in SANK 11867.

(3)<SANK 70214>

The strain for biotransformation used for the production of terpenoid derivative (II) or terpenoid derivative (III) of the present invention from substrate compound (2) is not particularly limited and is preferably a bacterium having hydroxylase activity. Examples thereof can include a bacterium belonging to the genus *Bacillus*.

The bacterium belonging to the genus *Bacillus* is preferably *Bacillus* sp., more preferably *Bacillus* sp. SANK 70214 (Deposition No. NITE BP-01914) (hereinafter, referred to as SANK 70214).

The partial nucleotide sequence of SANK 70214 16S rDNA is shown in SEQ ID NO: 1 (FIG. 7).

SANK 70214 was separated from a fresh water sample collected in Hokkaido in September 1997.

In order to identify the bacterial strain SANK 70214, the composition of a medium used in bacterial culture was as follows:

<TSB (Pearlcore Trypto-Soy Broth) Agar Medium>

| | |
|---|---|
| Pearlcore Trypto-Soy Broth (Eiken Chemical Co., Ltd.) | 30 g |
| Agar | 15 g |
| Distilled water | 1000 ml |

(The pH was adjusted to 8.0 before autoclaving).

SANK 70214 will be described below.

[1] Morphological Properties

The bacterium observed after culture at 28° C. for 24 hours in the TSB medium (pH 8.0) is a rod-shaped bacterium having cells of 1 μm in width and 4 to 5 μm in length and shows no motion.

[2] Cultural Properties

The color of the colonies after culture at 28° C. for 24 hours in the TSB medium (pH 8.0) is a semitransparent creamy white color and shines dully. The colonies have a round shape that bulges in a convex lens-like shape toward the center and have smooth surface and entire margins.

[3] Biological Properties (1) Catalase: +
(2) Growth temperature: 14 to 39° C.
(3) Gram staining: positive
(4) Utilization of Carbon source (API 50 CH was used)
  Erythritol: −
  D-Arabinose: −
  L-Arabinose: −
  D-Ribose: +
  L-Xylose: +
  Methyl-β-D-xylopyranoside: −
  D-Galactose−
  D-Mannose: +
  L-Rhamnose: +
  Dulcitol: −
  Inositol: −
  D-Sorbitol: −
  Methyl-α-D-mannopyranoside: −
  Methyl-α-D-glucopyranoside: −
  N-Acetyl glucosamine: −
  Amygdalin: +
  Salicin: +
  D-Lactose: −
  D-Melibiose: −
  D-Melezitose: −
  D-Raffinose: −
  Starch: −
  Glycogen: −
  Xylitol: −
  Gentiobiose: +
  D-Turanose: −
  D-Lyxose: −
  D-Tagatose: −
  D-Arabitol: −
  Gluconic acid: −
  2-Keto-gluconic acid: −
(5) Growth pH
  pH 6: +
  pH 7: +
  pH 8: +
  pH 9: +
  pH 10: +
(6) Growth in NaCl-containing medium
  0%: +
  2%: +
  4%: +
  6%: +
  8%: +
  10%: −

[4] Genetic Properties (1) G+C content: 40.8%
(2) 16S rDNA analysis: As a result of comparing the determined nucleotide sequence (1478 bp: SEQ ID NO: 1 of the Sequence Listing) with data on various type strains of bacteria registered in Ribosomal Database Project (RDP) (Release 11, (updated on Mar. 7, 2014)), the homology was highest to *B. gibsonii* DSM 8722 with a homology value of 99.5%. Phylogenetic analysis was further conducted by the neighbor-joining method of Saitou and Nei (Saitou N., and M. Nei, Molecular Biology and Evolution, 4, p. 406-425 (1987)) to obtain the results shown in FIG. 13.

SANK 70214 having these mycological properties was identified with reference to Bergey's Manual of Systematic Bacteriology, Vol. 3 (issued in 2009). From the results of analyzing the nucleotide sequence of 16S rDNA, SANK 70214 showed a close genealogical relationship with *B. gibsonii* DSM 8722. The morphological properties, cultural properties, biological properties, and genetic properties of SANK 70214 are well consistent with those of the genus *Bacillus*. Thus, SANK 70214 was identified as a strain belonging to the genus *Bacillus*. SANK 70214 differed from *B. gibsonii*, which showed the closest genealogical relationship therewith, in the utilization of carbon sources of L-arabinose, D-lactose, D-melibiose, D-melezitose, D-raffinose, and D-turanose. Also, SANK 70214 was clearly distinguished from known bacterial species of the genus *Bacillus* in terms of the nucleotide sequence of 16S rDNA. Thus, SANK 70214 was designated as *Bacillus* sp. SANK 70214.

SANK 70214 was internationally deposited under Deposition No. NITE BP-01914 with NITE Patent Microorganisms Depositary (NPMD), Biological Resource Center, National Institute of Technology and Evaluation (address: 2-5-8 Kazusakamatari, Kisarazu-shi, Chiba, Japan) on Aug. 7, 2014.

As is well known, microbes are susceptible to mutation in the natural world or by artificial operation (e.g., ultraviolet irradiation, radiation, or chemical agent treatment). Presumably, SANK 70214 of the present invention is also susceptible to such mutation. In the present invention, SANK 70214 encompasses all of its variants.

These variants also encompass those obtained by a genetic method, for example, recombination, transduction, or transformation.

Specifically, SANK 70214 as the strain for biotransformation used for the production of the terpenoid derivative of the present invention, its variants, and bacterial strains that are not clearly distinguished therefrom are all included in SANK 70214.

(4)<SANK 70314>

Another example of the bacterium belonging to the genus *Bacillus* as the strain for biotransformation used for the production of terpenoid derivative (II) or terpenoid derivative (III) of the present invention from substrate compound (2) can preferably include *Bacillus megaterium* SANK 70314 (Deposition No. NITE BP-01915) (hereinafter, referred to as SANK 70314).

The partial nucleotide sequence of SANK 70314 16S rDNA is shown in SEQ ID NO: 2 (FIG. 8).

SANK 70314 was separated from a soil sample collected in Okinawa prefecture in September 2013.

In order to identify the bacterial strain SANK 70314, the composition of a medium used in bacterial culture was as follows:

<NA (Pearlcore Nutrient Agar) Medium>

| Pearlcore Nutrient Agar (Eiken Chemical Co., Ltd.) | 35 g |
|---|---|
| Distilled water | 1000 ml |

SANK 70314 will be described below.
[1] Morphological Properties

The bacterium observed after culture at 28° C. for 24 hours in the nutrient agar (manufactured by Eiken Chemical CO., Ltd.) is a rod-shaped bacterium having cells of 1 µm in width and 4 to 5 µm in length and shows no motion.
[2] Cultural Properties The color of the colonies after culture at 28° C. for 24 hours in the nutrient agar is an opaque creamy white color and shines dully. The colonies have a round shape that bulges in a convex lens-like shape toward the center and have smooth surface and entire margins.
[3] Biological Properties
(1) Catalase: +
(2) Growth temperature: 13 to 46° C.
(3) Gram staining: positive
(4) Utilization of Carbon source (API 50 CH was used)
Glycerol: +
Erythritol: −
D-Arabinose: −
D-Ribose: +
L-Xylose: −
D-Adonitol: −
Methyl-β-D-xylopyranoside: −
D-Galactose: +
D-Fructose: +
L-Sorbose: −
L-Rhamnose: −
Dulcitol: −
Inositol: −
D-Sorbitol: −
Methyl-α-D-mannopyranoside: −
N-Acetyl glucosamine: +
Amygdalin: +
Arbutin: +
D-Cellobiose: +
D-Maltose: +
D-Lactose: −
D-Melibiose: +
D-Sucrose: +
D-Trehalose: +
Inulin: −
D-Melezitose: +
D-Raffinose: +
Xylitol: −
Gentiobiose: +
D-Turanose: +
D-Lyxose: −
D-Tagatose: −
D-Fucose: −
L-Fucose: −
D-Arabitol: −
L-Arabitol: −
Gluconic acid: −
2-Keto-gluconic acid: −
5-Keto-gluconic acid: −
(5) Growth pH
pH 6: +
pH 7: +
pH 8: +
pH 9: −
[4] Genetic Properties
(1) G+C content: 38.0%
(2) 16S rDNA analysis: As a result of comparing the determined nucleotide sequence (1383 bp: SEQ ID NO: 2 of the Sequence Listing) with data on various type strains of bacteria registered in Ribosomal Database Project (RDP) (Release 11, (updated on Mar. 7, 2014)), the homology was highest to *Bacillus megaterium* IAM 13418 with a homology value of 99.9%. Phylogenetic analysis was further conducted by the neighbor-joining method of Saitou and Nei (Saitou N., and M. Nei, Molecular Biology and Evolution, 4, p. 406-425 (1987)) to obtain the results shown in FIG. 13.

SANK 70314 having these mycological properties was identified with reference to Bergey's Manual of Systematic Bacteriology, Vol. 3 (issued in 2009). From the results of analyzing the nucleotide sequence of 16S rDNA, SANK 70314 showed a very close genealogical relationship with *Bacillus megaterium* IAM 13418. The morphological properties, cultural properties, biological properties, and genetic properties of SANK 70314 are well consistent with those of *Bacillus megaterium*. Thus, SANK 70314 was identified as *Bacillus megaterium* and designated as *Bacillus megaterium* SANK 70314.

SANK 70314 was internationally deposited under Deposition No. NITE BP-01915 with NITE Patent Microorganisms Depositary (NPMD), Biological Resource Center, National Institute of Technology and Evaluation (address: 2-5-8 Kazusakamatari, Kisarazu-shi, Chiba, Japan) on Aug. 7, 2014.

As is well known, microbes are susceptible to mutation in the natural world or by artificial operation (e.g., ultraviolet irradiation, radiation, or chemical agent treatment). Presumably, SANK 70314 of the present invention is also susceptible to such mutation. In the present invention, SANK 70314 encompasses all of its variants.

These variants also encompass those obtained by a genetic method, for example, recombination, transduction, or transformation.

Specifically, SANK 70314 as the strain for biotransformation used for the production of the terpenoid derivative of the present invention, its variants, and bacterial strains that are not clearly distinguished therefrom are all included in SANK 70314.

(5)<Transformed Strain of SANK 70214 and Transformed Strain of SANK 70314>

In order to produce terpenoid derivative (III) of the present invention from substrate compound (2), a nucleotide sequence encoding a protein involved in the hydroxylation of substrate compound (2) is determined from the microbe described above, and a microbe expressing the protein of the present invention can be used. Specifically, a protein that selectively hydroxylates substrate compound (2) into terpenoid derivative (III) is determined from each of SANK 70214 and SANK 70314, and a microbe expressing the protein can be allowed to act on substrate compound (2) to produce terpenoid derivative (III).

<Protein of Present Invention>

The protein of the present invention can be prepared by obtaining and using a gene encoding the protein. Hereinafter, a method for obtaining the gene of the present invention and a method for preparing the protein of the present invention will be specifically described.

<Method for Obtaining Gene of Present Invention>

Genomic DNA is extracted by a routine method from each of SANK 70214 and SANK 70314, and the whole genome is analyzed using a genome sequencer. A protein having hydroxylation ability can be identified to obtain the gene of the present invention.

The obtainment of the hydroxylase-related genes of the present invention had a problem that could not be readily solved by an approach generally attempted by those skilled in the art. The genus *Bacillus* to which the microbe having the ability to transform substrate compound (2) to terpenoid derivative (III) belongs is considered to retain a plurality of genes involved in hydroxylation in the genome. Furthermore, the normal functions of enzymes involved in hydroxylation require ferredoxin and reductase that supplies electrons to these enzymes. Thus, it seemed difficult to obtain the hydroxylases of interest by general Southern hybridization or degenerate PCR using only the genes of the hydroxylases. Accordingly, these genes were comprehensively analyzed by genome analysis using a next-generation sequencer to find the coding nucleotide sequences of genes of hydroxylases involved in the present invention.

The thus-obtained nucleotide sequence encoding each protein of the present invention having hydroxylation activity against substrate compound (2) is shown in the following (f), (g), (h), (i), or (j):

(f) the nucleotide sequence described in SEQ ID NO: 3 (FIG. 9) encoding a protein of SANK 70214 having hydroxylation activity, (g) the nucleotide sequence described in SEQ ID NO: 4 (FIG. 10) encoding a protein of SANK 70314 having hydroxylation activity, (h) DNA, as an altered form of the DNA represented by (f) or (g), which has a nucleotide sequence hybridizing under stringent conditions to any DNA represented by (f) or (g) and encodes a protein having hydroxylation activity against substrate compound (2), (i) DNA which does not hybridize under stringent conditions to any DNA represented by (f) or (g) due to the degeneracy of the genetic code, but encodes a protein having the same amino acid sequence as that of a protein encoded by any DNA represented by (f) or (g), and (j) DNA which has a nucleotide sequence derived from the nucleotide sequence of the DNA represented by (f) by the deletion, substitution, and/or addition of one or several bases and encodes a protein having hydroxylation activity against substrate compound (2).

(k) Examples of the protein of the present invention derived from SANK 70214 having hydroxylation activity against substrate compound (2) include the following proteins:

a protein having the amino acid sequence of SEQ ID NO: 5 (FIG. 11), a protein having an amino acid sequence derived from the amino acid sequence of the protein of SEQ ID NO: 5 by the deletion, substitution, insertion, or addition of one or several amino acids, a protein having an amino acid sequence having 90% or higher sequence identity to the amino acid sequence of the protein of SEQ ID NO: 5, and a protein encoded by DNA hybridizing under stringent conditions to DNA consisting of a nucleotide sequence encoding the protein of SEQ ID NO: 5.

(1) Examples of the protein of the present invention derived from SANK 70314 having hydroxylation activity against substrate compound (2) include the following proteins:

a protein having the amino acid sequence of SEQ ID NO: 6 (FIG. 12), a protein having an amino acid sequence derived from the amino acid sequence of the protein of SEQ ID NO: 6 by the deletion, substitution, insertion, or addition of one or several amino acids, a protein having an amino acid sequence having 90% or higher sequence identity to the amino acid sequence of the protein of SEQ ID NO: 6, and a protein encoded by DNA hybridizing under stringent conditions to DNA consisting of a nucleotide sequence encoding the protein of SEQ ID NO: 6.

3. Transformant of Present Invention

The transformant of the present invention is obtained by transfecting a host with the protein-encoding gene (f), (g), (h), (i) or (j) by a usual genetic engineering method. Specifically, an expression vector that allows the gene encoding the transformant of the present invention to be expressed in host cells is prepared, and host cells can be transfected with this expression vector so that the host cells are transformed to prepare the transformant.

The transformant used for producing terpenoid derivative (III) of the present invention from substrate compound (2) is a transformant expressing the protein that hydroxylates substrate compound (2) into terpenoid derivative (III). The transformant is not particularly limited and is preferably a transformant expressing the protein (k) or (l) with *Escherichia coli* as a host, more preferably a transformant expressing the protein (k) or (l) with *Bacillus subtilis* as a host, further preferably *Bacillus subtilis* SANK 70214T (hereinafter, referred to as SANK 70214T) or *Bacillus subtilis* SANK 70314T (hereinafter, referred to as SANK 70314T).

The host for the transformant is not particularly limited, and a microbe, an alga, a plant, or an animal can be used. The host is preferably a microbe, for efficiency of transformation.

The microbe used as the host is preferably *Escherichia coli* or *Bacillus subtilis*, more preferably *Bacillus subtilis*.

The vector on which the expression vector is based can be any vector that can transfer DNA encoding the protein having hydroxylation activity against substrate compound (2), either alone or together with DNA encoding a protein having ferredoxin functions, to the host so that the gene can be expressed in the host cells. For example, a vector that has an expression control region such as a promoter or a terminator appropriate for the type of the host to be transfected and has a replication origin, a selection marker, and the like can be used. Alternatively, the vector may be a vector, such as a plasmid, which autonomously grows or replicates outside the chromosome, or may be a vector that is integrated into the chromosome.

The transformation method is not particularly limited as long as the method is capable of transfecting the host with the gene of interest. For example, a method using calcium ions, a general competent cell transformation method (Journal of Bacteriology, 93, 1925 (1967)), a protoplast transformation method (Molecular and General Genetics, 168, 111 (1979)), electroporation (FEMS Microbiology Letters, 55, 135 (1990)), or an LP transformation method (T. Akamatsu and J. Sekiguchi, Archives of Microbiology, 1987, 146, p. 353-357; and T. Akamatsu and H. Taguchi, Bioscience, Biotechnology, and Biochemistry, 2001, 65, 4, p. 823-829) can be used.

The transformant harboring the gene fragment of interest can be selected by use of a selection marker or the like. For example, as a result of transferring a vector-derived drug resistance gene together with the DNA fragment of interest into the host cells during the transformation, the selection can be carried out by using drug resistance acquired by the transformant as an index. Alternatively, the transfer of the DNA fragment of interest can also be confirmed by PCR or the like with the genome as a template.

4. Culture Method and Purification Method (Production and Purification of Terpenoid Derivatives of the Present Invention)

The aforementioned strain for biotransformation can be cultured using a medium as generally used in the production of secondary metabolites of microbes. Such a medium contains carbon source, nitrogen source, inorganic salts, very small amount of growth factors, trace metal, and the like, utilizable by microbes Examples of the carbon source include glucose, fructose, maltose, sucrose, mannitol, glycerin, dextrin, oat, rye, starch, potato, corn flour, cottonseed oil, molasses, citric acid, and tartaric acid. These carbon sources can be used alone or in combination.

The amount of the carbon source added is usually in the range of 1 to 10% by weight of the amount of the medium.

A substance containing a protein and a hydrolysate thereof, or inorganic salts is usually used as the nitrogen source.

Examples of such a nitrogen source include soybean flour, bran, peanut flour, cottonseed meal, casein hydrolysates, Pharmamin, fish meal, corn steep liquor, peptone, meat extracts, yeast, yeast extracts, malt extracts, sodium nitrate, ammonium nitrate, and ammonium sulfate. These nitrogen sources can be used alone or in combination.

The amount of the nitrogen source added is usually in the range of 0.2 to 10% by weight of the amount of the medium.

Also, salts capable of providing ions of sodium, potassium, magnesium, ammonium, calcium, phosphate, sulfate, chloride, carbonate, or the like may be added into the medium.

Vitamins such as vitamin B1 and biotin, a substance promoting fungus body proliferation, such as thiamin, and a salt of a metal such as manganese or molybdenum, utilizable by microbes may be further added into the medium.

In the case of a liquid medium, an antifoaming agent such as silicon oil, a polyalkylene glycol ether, a plant oil, an animal oil, or a surfactant may be added to the medium in order to prevent the foaming of the medium.

The pH of the liquid medium for use in the culture of the strain for biotransformation depends on the pH stability of the fungal strain and the terpenoid derivative of the present invention, etc.

The culture temperature of the strain for biotransformation depends on the thermal stability of the fungal strain and the terpenoid derivative of the present invention, etc. In the case where the strain for biotransformation is SANK 10312 strain, the culture temperature is preferably 9 to 33° C., more preferably 20 to 35° C. In the case where the strain for biotransformation is SANK 11867, the culture temperature is preferably 5 to 33° C., more preferably 13 to 31° C. In the case where the strain for biotransformation is SANK 70214, the culture temperature is preferably 14 to 39° C., more preferably 20 to 35° C. In the case of SANK 70314, the culture temperature is preferably 13 to 46° C., more preferably 20 to 40° C. In the case where the strain for biotransformation is SANK 70214T, the culture temperature is preferably 5 to 50° C., more preferably 27 to 37° C. In the case of SANK 70314T, the culture temperature is preferably 5 to 50° C., more preferably 27 to 37° C.

Examples of the method for culturing the strain for biotransformation can include, but are not particularly limited to, a culture method using a solid medium, a stirring culture method, a shake culture method, an aeration culture method, and an aeration stirring culture method. The culture method is preferably a stirring culture method, a shake culture method, an aeration culture method, and an aeration stirring culture method, more preferably a shake culture method. The aeration stirring culture method is more preferred for culture at an industrial scale.

The culture of the strain for biotransformation usually starts from seed culture using a small amount of a medium inoculated with a slant culture of the strain for biotransformation and is achieved by optional seed culture carried out again at a larger scale followed by main culture at a larger scale at the final stage.

In the case of culturing the strain for biotransformation at a small scale, seed culture is carried out using an Erlenmeyer flask or the like, and, if necessary, seed culture is carried out again at a larger scale, followed by main culture using an Erlenmeyer flask or the like.

In the case of culturing the strain for biotransformation at a large scale, a jar fermenter or a tank equipped with a stirring apparatus and an aeration apparatus is preferably used. Use of such an apparatus allows the medium to be prepared and sterilized in the jar fermenter or the tank. This method is suitable for large-scale production.

The culture time of the strain for biotransformation after addition of the substrate depends on the fungal or bacterial strain. In the case where the strain for biotransformation is SANK 10312, the culture time is preferably 2 to 14 days, more preferably 3 to 10 days. In the case where the strain for biotransformation is SANK 11867, the culture time is preferably 2 to 14 days, more preferably 3 to 10 days. In the case where the strain for biotransformation is SANK 70214, the culture time is preferably 1 to 10 days, more preferably 3 to 7 days. In the case of SANK 70314, the culture time is preferably 1 to 10 days, more preferably 1 to 7 days. In the case where the strain for biotransformation is SANK 70214T, the culture time is preferably 1 to 168 hours, more preferably 2 to 24 hours. In the case of SANK 70314T, the culture time is preferably 1 to 168 hours, more preferably 8 to 96 hours.

After the completion of the culture, the terpenoid derivative of the present invention can be extracted from the obtained culture, the fungus body contained therein, and/or the culture supernatant. A centrifugation method or a filtration method with diatomaceous earth as a filter aid can be used for separating the fungus body and other solid materials from the culture supernatant.

For the extraction of the terpenoid derivative of the present invention, the physicochemical properties of the compound can be utilized. The terpenoid derivative of the present invention contained in the culture filtrate or the culture supernatant can be extracted with a water-immiscible organic solvent such as ethyl acetate, chloroform, ethylene chloride, methylene chloride, or butanol, or a mixed solvent of two or more of these solvents. The terpenoid derivative of the present invention contained in the fungus body can be extracted therefrom using 50 to 90% aqueous acetone or aqueous methanol and extracted in the same way as in the case where the terpenoid derivative is present in the culture filtrate or the culture supernatant, after distilling off of the organic solvent. The terpenoid derivative of the present invention contained in the whole cultures can be extracted by the addition of 20 to 80%, preferably 40 to 60%, more preferably 50%, of acetone or methanol to the whole culture. After completion of the extraction, the extracts are filtered with diatomaceous earth as a filter aid, and the terpenoid derivative can be extracted from the obtained soluble matter in the same way as in the case where the terpenoid derivative is present in the culture filtrate or the culture supernatant.

The purification for isolating the terpenoid derivative of the present invention from the extracts can be carried out by a purification technique such as adsorption chromatography, ion-exchange chromatography, partition chromatography, reverse-phase chromatography, or high-performance liquid chromatography (hereinafter, referred to as HPLC).

The adsorption chromatography is carried out by: contacting the extracts containing the terpenoid derivative of the present invention with an adsorbent to remove impurities through adsorption; or adsorbing the terpenoid derivative of the present invention to remove impurities, followed by elution. Examples of the adsorbent can include active carbon, Amberlite XAD-2, Amberlite XAD-4, and Amberlite XAD-16 (all manufactured by Rohm and Haas Company), and Diaion HP-20, Diaion HP-21, Diaion HP-20SS, Sepabeads SP-207, Sepabeads SP-850, and Sepabeads SP-700 (all manufactured by Mitsubishi Chemical Corp.). Examples of the solvent for use in the elution of the adsorbed terpenoid derivative of the present invention can include organic solvents such as methanol, acetone, butanol, and acetonitrile, and mixed solutions thereof with water.

The ion-exchange chromatography is carried out by use of the fact that the terpenoid derivative of the present invention behaves as a neutral substance. Specifically, the extracts containing the terpenoid derivative of the present invention are contacted with, for example, an ion-exchange carrier to adsorb unnecessary matter onto the carrier while passing the terpenoid derivative of the present invention therethrough. Examples of the ion-exchange carrier can include DEAE-Sephadex, DEAE-Sepharose, QAE-Sephadex, CM-Sephadex, and SP-Sephadex (all manufactured by GE Healthcare Life Sciences), DEAE-Toyopearl, QAE-Toyopearl, CM-Toyopearl, and SP-Toyopearl (all manufactured by Tosoh Corp.), Duolite A113LF, Duolite A116, Duolite A368S, Duolite A375LF, Duolite C20J, and Duolite C433LF (all manufactured by Diamond Shamrock Chemical Company), Amberlite IRA-67, Amberlite IRA-98, Amberlite IRA400J, Amberlite IRA458RF, Amberlite IR120B, and Amberlite IRC76 (all manufactured by Rohm and Haas Company), and Dowex 50WX4, Dowex HCR-S, Dowex 1×4, Dowex 22, Dowex 66, and Dowex SBR-P (manufactured by The Dow Chemical Company).

Examples of the carrier for use in the distribution chromatography can include silica gel, TSK gel Toyopearl HW-40F (manufactured by Tosoh Corp.), Sephadex LH-20 (manufactured by GE Healthcare Life Sciences), and cellulose (manufactured by Merck KGaA).

Examples of the carrier for use in the reverse-phase chromatography can include Cosmosil 140C18 (manufactured by Nacalai Tesque, Inc.) and ODS-A (manufactured by YMC Co., Ltd.).

Examples of the column for use in the HPLC can include reverse-phase columns such as Shodex Asahipak ODP50-4E (manufactured by Showa Denko K.K.), YMC pack ODS-A (manufactured by YMC Co., Ltd.), CAPCELL PAK UG120 (manufactured by Shiseido Co., Ltd.), and Unison C18 (manufactured by Imtakt Corp.).

The terpenoid derivative of the present invention can be isolated using these purification techniques alone or in appropriate combination. If necessary, the same purification technique can be repeated. A method suitable for purification, such as a column chromatography method, a batch chromatography method, a thin-layer chromatography method, can be selected in order to carry out each purification technique.

The steric structure of the obtained terpenoid derivative of the present invention is derived from the steric structure of the starting compound. The steric structures of substituents newly introduced to the starting compound were determined using nuclear Overhauser effect spectroscopy (NOESY).

For example, the steric structure of terpenoid derivative (I) having the physicochemical properties described in (2) above was determined from the steric structure of the starting compound, the physicochemical properties described in (2), and measurement results of NOESY described later in Example 1.

Likewise, the steric structure of terpenoid derivative (II) having the physicochemical properties described in (4) above was determined from the steric structure of the starting compound, the physicochemical properties described in (4), the physicochemical properties described in (6), and measurement results of NOESY described later in Example 3.

5. Medicament Comprising Terpenoid Derivative of the Present Invention

The terpenoid derivative of the present invention purified as mentioned above has the action of activating the Keap1/Nrf2/ARE signaling pathway and has an anti-inflammatory action and a cytoprotective action.

Activation of the Keap1/Nrf2/ARE signaling pathway induces its target gene of NAD(P)H:quinone oxidoreductase-1 (NQO1), heme oxygenase-1 (HO-1), γ-glutamate cysteine ligase catalytic subunit (GCLC), or the like (Non-patent Literature 1). When these enzymes are increased in amount or activated, the cells become resistant to poison, oxidative stress, inflammation, etc. The terpenoid derivative of the present invention is therefore useful as a preventive or therapeutic agent for diseases such as an eye disease, a renal disease, a hepatic disease, and diabetes mellitus and its complications.

Examples of the eye disease include diseases such as allergic conjunctival disease, viral conjunctivitis, pterygium, corneal infection, dry eye, corneal disorder (which is corneal epithelial disorder and/or corneal endothelial disorder), uveitis, Behcet's disease, diabetic retinopathy, retinal detachment, retinal vein occlusion (RVO), central serous chorioretinopathy, age-related macular degeneration (AMD), diabetic macular edema (DME), macular disease, retinitis pigmentosa, glaucoma, and cataract.

Examples of the renal disease include diseases caused by kidney problems, such as acute nephritis, chronic nephritis, acute renal failure, chronic renal failure, nephrotic syndrome, IgA nephropathy, diabetic nephropathy, gouty kidney, nephrosclerosis, hydronephrosis, tubulointerstitial nephritis, decreased renal function after coronary-artery bypass surgery, and urinary tract infection.

Examples of the respiratory disease include bronchitis, pneumonia, pleuritis, chronic obstructive pulmonary disease (COPD), acute lung injury (ALI), diffuse panbronchiolitis, pulmonary emphysema, and asthma.

Examples of the hepatic disease include alcoholic fatty liver, non-alcoholic steatohepatitis, hepatic fibrosis, liver cirrhosis, and hepatic dysfunction associated with liver transplantation.

Examples of the brain disease include Alzheimer's disease, Parkinson's disease, Huntington's disease, amyotrophic lateral sclerosis (ALS), cerebral infarction, and multiple sclerosis (MS).

Examples of the heart disease include myocardial infarction.

Examples of diabetes mellitus and its complications include diabetic retinopathy, diabetic nephropathy, and diabetic neuropathy.

The terpenoid derivative of the present invention is particularly useful as a preventive or therapeutic agent for, among these diseases, dry eye, corneal disorder (which is corneal epithelial disorder and/or corneal endothelial disorder), uveitis, diabetic retinopathy, retinal vein occlusion, age-related macular degeneration, diabetic macular edema, or glaucoma as the eye disease, diabetic nephropathy as the renal disease, chronic obstructive pulmonary disease or acute lung injury (ALI) as the respiratory disease, non-alcoholic steatohepatitis or hepatic dysfunction associated with liver transplantation as the hepatic disease, or cerebral infarction or multiple sclerosis as the brain disease.

The terpenoid derivative of the present invention is further preferred as a preventive or therapeutic agent for dry eye, a preventive or therapeutic agent for a disorder of the corneal epithelium and/or the corneal endothelium, a preventive or therapeutic agent for age-related macular degeneration, a preventive or therapeutic agent for diabetic macular edema and/or retinal vein occlusion, a preventive or therapeutic agent for chronic obstructive pulmonary disease, a preventive or therapeutic agent for cerebral infarction, or a preventive or therapeutic agent for multiple sclerosis, among these diseases.

In the case of using the terpenoid derivative of the present invention as a medicament, this medicament can be administered in various forms. The dosage form depends on the preparation, age, sex, disease, etc. For example, tablets, pills, powders, granules, syrups, solutions, suspensions, emulsions, granules, or capsules are orally administered. For example, injections are administered intravenously, intramuscularly, intracutaneously, subcutaneously, intravitreally, intracamerally, subconjunctivally, to the capsule of Tenon, or intraperitoneally. Eye drops are instilled into the eyes. Eye ointments are used for ophthalmic mucous membranes. Suppositories are intrarectally administered. Any of these administration methods may be achieved by the administration of sustained-release pharmaceutical compositions.

In the case of using the terpenoid derivative of the present invention as a medicament for an eye disease, oral administration is possible. In general, however, instillation into the eyes, intravitreal administration, intracameral administration, subconjunctival administration, or administration to the capsule of Tenon, which permits direct administration to the point of action, is often used.

Various pharmaceutical compositions containing the terpenoid derivative of the present invention as an active ingredient can be produced according to routine methods using known additives usually usable in the field of pharmaceutical preparations, such as excipients, binders, disintegrants, lubricants, solubilizers, corrigents, and coating agents.

6. Sustained-Release Pharmaceutical Composition for Treatment and/or Prevention of Eye Disease, Comprising Terpenoid Derivative of Present Invention as Active Ingredient The sustained-release pharmaceutical composition for the treatment and/or prevention of an eye disease, comprising the terpenoid derivative of the present invention as an active ingredient (hereinafter, also referred to as the sustained-release pharmaceutical composition of the present invention) has a base material administrable to the vitreous body and a form administrable to the vitreous body and is directly administered into the eyes.

The direct administration of a medicament into the eyes places a large burden on patients. The sustained-release pharmaceutical composition of the present invention can maintain a pharmacological action thereof for 1 week or longer by the sustained release of the terpenoid derivative under physiological conditions. Therefore, the frequency of administration can be decreased, and the burden on patients is reduced.

The sustained-release pharmaceutical composition of the present invention induces enzymes involved in the suppression of poison, oxidative stress, inflammation, etc., and consequently protects retinal tissues and is useful as a local administration-type sustained-release pharmaceutical composition for the treatment or prevention of a posterior eye disease. Examples of the posterior eye disease include age-related macular degeneration, diabetic macular edema, and diabetic retinopathy.

A biodegradable polymer is used as the base material of the sustained-release pharmaceutical composition of the present invention. Examples of the biodegradable polymer include polylactic acid, polyglycolic acid, and poly(lactic-co-glycolic acid). Polylactic acid or poly(lactic-co-glycolic acid) is preferred.

These biodegradable polymers may be produced according to production methods known in the art, or various commercially available products differing in molecular weight or copolymerization ratio may be used (J. Biomaterials Nanobiotechnology 2012: 3: 208-252; and Biomedical Engineering, Trends in Materials Science, Laskovski, A (Ed.) pp. 489-512, InTech, Rijeka, 2011).

The form of the sustained-release pharmaceutical composition of the present invention includes powder pharmaceutical compositions intended for sustained release in the form of powders as well as sustained-release forms of rods, sheets, films, discs, or microcapsules of the terpenoid derivative of the present invention dispersed in the base material uniformly or in a particle state. Among these, a microsphere or rod form is preferred as the form of the sustained-release pharmaceutical composition for the treatment or prevention of a posterior eye disease.

The amount of the terpenoid derivative of the present invention contained in the sustained-release pharmaceutical composition of the present invention is not particularly limited and is preferably 5 to 80% by weight, more preferably 20 to 60% by weight.

Examples of the method for producing the sustained-release pharmaceutical composition of the present invention in the form of microspheres includes drying methods in water (e.g., o/w, w/o, and w/o/w methods), a phase separation method, a spray drying method, a granulation method using supercritical fluids, methods equivalent thereto, and methods described in Examples mentioned later (R. T. Liggins, H. M. Burt/International Journal of Pharmaceutics 222 (2001) 19-33; K. Andreas et al./Acta Biomaterialia 7 (2011) 1485-1495; J. Herberger et al./Journal of Controlled Release 90 (2003) 181-195; and A. J. Thote, R. B. Gupta/ Nanomedicine: Nanotechnology, Biology, and Medicine 1 (2005) 85-90).

Examples of the method for producing the sustained-release pharmaceutical composition of the present invention in the form of a polymer implant such as a rod, a sheet, a film, a disc, or microspheres include a method which involves appropriately adding a surfactant or an emulsifier as a solvent for formation, and processing an internal core of the sustained-release pharmaceutical composition having the desired shape by use of various techniques such as melt extrusion, injection molding, compression molding (including tableting), or roller compression into the desired shape or structure using an organic solvent.

An organic solvent, such as acetone, which is classified as an FDA class 3 solvent (a solvent that is low in toxicity and allows residual solvent to be removed by minimum use), is used as the organic solvent used for molding.

In the case of processing the internal core of the sustained-release pharmaceutical composition of the present invention without the use of organic solvent, this processing can be carried out under conditions where the terpenoid derivative of the present invention is thoroughly mixed with the whole of the base material biodegradable polymer or only a specific site of this polymer and dispersed or dissolved therein.

7. Dose and Frequency of Administration of Terpenoid Derivative of Present Invention The dose of the terpenoid derivative of the present invention differs depending on symptoms, age, etc., and is preferably 0.0001 μg/site to 100 μg/site for local administration. The dose for systemic administration is preferably 0.00001 mg/kg to 10 mg/kg.

The frequency of administration of the pharmaceutical drug containing the terpenoid derivative of the present invention as an active ingredient is several times a day, once a day, or once every few days. The sustained-release pharmaceutical composition is administered once every a week, once every four weeks, once every three months, or once every six months as a guideline.

Next, the present invention will be described in more detail with reference to the Examples, Test Examples, and Formulation Examples of pharmaceutical compositions. However, the present invention is not intended to be limited by these.

EXAMPLES

Example 1

Production of Terpenoid Derivative (I) and Terpenoid Derivative (III) (Strain for Biotransformation: SANK 10312)

[Formula 8]

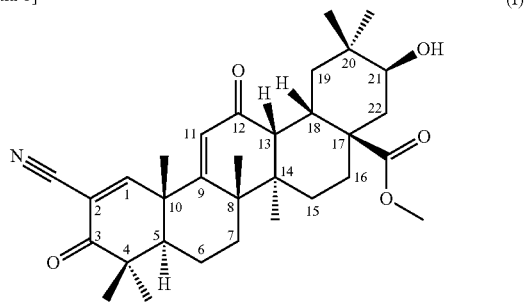

(I)

(1) Cultivation of Strain of Genus *Chaetomium* for Biotransformation 20 ml of a seed culture medium having the composition shown in Table 1 below was placed in each of four 100-ml Erlenmeyer flasks, sterilized at 121° C. for 20 minutes, and then cooled to room temperature. 1 ml of a spore suspension of SANK 10312 was inoculated to the medium in each flask and cultured for 2 days under conditions of 23° C. and 210 rpm in a rotating shaker. Hereinafter, the obtained culture solution is referred to as "seed culture solution".

TABLE 1

| Composition of seed culture medium for SANK 10312 | |
|---|---|
| Glycerin | 30 g |
| Glucose | 30 g |
| Soluble starch | 20 g |
| Soybean meal | 10 g |
| Gelatin | 2.5 g |
| Yeast extract (Difco) | 2.5 g |
| NH$_4$NO$_3$ | 2.5 g |
| Agar | 3 g |
| Antifoaming agent *1 | 0.1 ml |
| Tap water | 1000 ml |

*1 Nissan Disfoam CB-442 (manufactured by NOF Corp.)
*2 pH was unadjusted.

80 ml of a main culture medium having the composition shown in Table 2 below was placed in each of thirteen 500-ml Erlenmeyer flasks, sterilized at 121° C. for 20 minutes, and then cooled to room temperature. 4 ml of the seed culture solution of SANK 10312 was aseptically inoculated to the medium in each flask and cultured for 2 days under conditions of 23° C. and 210 rpm in a rotating shaker. 0.8 ml of a solution of CDDO-Me dissolved at a concentration of 10 mg/ml in dimethyl sulfoxide was added to this culture solution in each flask, and the mixture was cultured again at 210 rpm at 23° C. for 6 days in a rotating shaker.

TABLE 2

| Composition of main culture medium | |
|---|---|
| Glycerin | 30 g |
| Glucose | 30 g |

TABLE 2-continued

| Composition of main culture medium | |
|---|---|
| Soluble starch | 20 g |
| Soybean flour | 10 g |
| Gelatin | 2.5 g |
| Yeast extract (Difco) | 2.5 g |
| $NH_4NO_3$ | 2.5 g |
| Antifoaming agent *1 | 0.1 ml |
| Tap water | 1000 ml |

*1 Nissan Disfoam CB-442 (manufactured by NOF Corp.)
*2 pH was unadjusted.

(2) Isolation of Terpenoid Derivative (I) and Terpenoid Derivative (III)

The behaviors of terpenoid derivative (I) and terpenoid derivative (III) in this Example were monitored by HPLC under conditions given below.
Column: Unison UK-C18
 (4.6 mm in diameter×75 mm in length; manufactured by Imtakt Corp.)
solvent: A: 10 mM aqueous ammonium formate solution containing 0.01% formic acid
 B: acetonitrile containing 0.01% formic acid
 A/B=equilibration with 5/5 followed by linear gradient for 7 minutes up to A/B=1/9
flow rate: 1.0 ml/min
detection: ultraviolet absorption λ=230 nm
retention time: 4.3 minutes (terpenoid derivative (I))
 4.9 minutes (terpenoid derivative (III)).

To 1,040 ml of the culture solution obtained in paragraph (1), an equal amount of acetone was added, and the mixture was allowed to stand at room temperature for 1 hour. Then, the mycelia was removed by filtration under reduced pressure to obtain 2,000 ml of a filtrate. To this filtrate, 1 L of ethyl acetate was added for liquid-liquid distribution to obtain an organic layer containing the compounds of interest. The obtained organic layer was washed with saturated saline and dried over anhydrous sodium sulfate, and the solvent was evaporated to dryness to obtain 549.9 mg of a powder containing terpenoid derivative (I) and terpenoid derivative (III). A 275 mg aliquot of this powder was dissolved in 1.37 ml of methanol. A 0.2 ml aliquot of this solution was applied to an HPLC column (Unison US-C18; 20 mm in diameter×150 mm in length; manufactured by Imtakt Corp.) equilibrated in advance with solvents of 0.01% aqueous formic acid solution:acetonitrile containing 0.01% formic acid=45:55, followed by elution at a flow rate of 18.0 ml/min with solvents of 0.01% aqueous formic acid solution:acetonitrile containing 0.01% formic acid=45:55. The ultraviolet absorption of the compounds of interest was detected at a wavelength λ=230 nm. A peak appearing at a retention time of 9.1 minutes (terpenoid derivative (I)) and a peak appearing at a retention time of 12.3 minutes (terpenoid derivative (III)) were each separated 7 times. The fraction solutions of each compound were combined and concentrated under reduced pressure, and the obtained suspension was lyophilized to obtain 1.4 mg of terpenoid derivative (I) as a colorless powder and 16.2 mg of terpenoid derivative (III) as a colorless powder.

The steric structure of the obtained terpenoid derivative (I) of the present invention was determined using two-dimensional nuclear magnetic resonance spectroscopy (NOESY).

In the two-dimensional nuclear magnetic resonance spectroscopy (NOESY) of terpenoid derivative (I), the correlation was observed between the β-proton at the 19-position and the β-proton at the 21-position. Its steric structure was therefore determined as represented by the formula (I).

Measurement values of physicochemical properties of terpenoid derivative (I)
1) appearance: a colorless powdery substance
2) molecular formula: $C_{32}H_{43}NO_5$
3) molecular weight: 521 (measured by ESI mass spectrometry)
4) the accurate mass, $[M+H]^+$, measured by high-resolution LC-ESI mass spectrometry is as given below:
found: 522.32062
calculated: 522.32140
5) $^1H$-nuclear magnetic resonance spectra: the $^1H$-nuclear magnetic resonance spectra (500 MHz) measured in deuterated chloroform referenced to 0.00 ppm using TMS are as given below:
σ: 0.98 (3H, s), 0.99 (3H, s), 1.00 (3H, s), 1.17 (3H, s), 1.18-1.22 (1H, m), 1.25 (3H, s), 1.28-1.30 (1H, m), 1.33 (3H, s), 1.49 (3H, s), 1.51-1.55 (1H, m), 1.62-1.66 (1H, m), 1.68-1.71 (1H, m), 1.69-1.72 (1H, m), 1.70-1.80 (2H, m), 1.77-1.79 (1H, m), 1.76-1.82 (2H, m), 1.85-1.89 (2H, m), 2.96 (1H, d, J=5.0 Hz), 3.04 (1H, ddd, J=4.0 Hz, 4.0 Hz, 14.0 Hz), 3.49 (1H, dd, J=5.0 Hz, 11.5 Hz), 3.71 (3H, s), 5.97 (1H, s), 8.03 (1H, s) ppm.
6) $^{13}C$-nuclear magnetic resonance spectra: the $^{13}C$-nuclear magnetic resonance spectra (125 MHz) measured in deuterated chloroform referenced to 0.00 ppm using TMS are as given below:
σ: 16.4 (q), 18.2 (t), 21.4 (q), 21.5 (q), 23.9 (t), 24.6 (q), 26.6 (q), 27.0 (q), 28.1 (t), 29.1 (q), 31.1 (d), 31.6 (t), 35.8 (t), 35.9 (s), 40.1 (t), 42.0 (s), 42.5 (s), 45.0 (s), 45.7 (s), 47.7 (d), 48.9 (s), 49.0 (d), 52.1 (q), 73.7 (d), 114.3 (s), 114.6 (s), 124.0 (d), 165.5 (d), 168.5 (s), 176.6 (s), 196.5 (s), 198.7 (s) ppm. 7) high-performance liquid chromatography:
Column: Unison UK-C18
 (4.6 mm in diameter×75 mm in length; manufactured by Imtakt Corp.)
solvent: A: 10 mM aqueous ammonium formate solution containing 0.01% formic acid
 B: acetonitrile containing 0.01% formic acid
 A/B=equilibration with 5/5 followed by linear gradient for 7 minutes up to A/B=1/9
flow rate: 1.0 ml/min
temperature: 40° C.
detection: ultraviolet absorption λ=230 nm
retention time: 4.3 minutes
8) The $^1H$-nuclear magnetic resonance spectra of terpenoid derivative (I) are shown in FIG. 1, and the two-dimensional nuclear magnetic resonance spectra ($^1H$-$^{13}C$ HSQC spectra) thereof are shown in FIG. 2. As a result of analyzing the 1H-nuclear magnetic resonance spectra and the two-dimensional nuclear magnetic resonance spectra ($^1H$-$^{13}C$ HSQC spectra), each proton was attributed as follows:
β-proton at the 19-position: 1.28 to 1.30 ppm (methylene)
β-proton at the 21-position: 3.49 ppm (methine) 9) The two-dimensional nuclear magnetic resonance spectra ($^1H$-$^1H$ NOESY spectra) of terpenoid derivative (I) are shown in FIG. 3. In FIG. 3, the correlation was observed between the β-proton at the 19-position and the β-proton at the 21-position. Its steric structure was therefore determined as represented by (I).

Example 2

Production of Terpenoid Derivative (I) and Terpenoid Derivative (III) (Strain for Biotransformation: SANK 11867)

(1) Culture of Strain of Genus *Chaetomium* for Biotransformation 20 ml of a seed culture medium having the composition shown in Table 1 of Example 1 was placed in each of 176 100-ml Erlenmeyer flasks, sterilized at 121° C. for 20 minutes, and then cooled to room temperature. 1 ml of a spore suspension of SANK 11867 was inoculated to the medium in each flask and cultured for 2 days under conditions of 23° C. and 210 rpm in a rotating shaker. Hereinafter, the obtained culture solution is referred to as "seed culture solution".

80 ml of a main culture medium having the composition shown in Table 2 of Example 1 was placed in each of 583 500-ml Erlenmeyer flasks, sterilized at 121° C. for 20 minutes, and then cooled to room temperature. 4 ml of the seed culture solution of SANK 11867 was aseptically inoculated to the medium in each flask and cultured for 2 days under conditions of 23° C. and 210 rpm in a rotating shaker. 0.8 ml of a solution of CDDO-Me dissolved at a concentration of 30 mg/ml in dimethyl sulfoxide was added to this culture solution in each flask, and the mixture was cultured again at 210 rpm at 23° C. for 6 days in a rotating shaker.

(2) Isolation of Terpenoid Derivative (I) and Terpenoid Derivative (III)

The behaviors of terpenoid derivative (I) and terpenoid derivative (III) in this Example were monitored by HPLC under conditions given below.

Column: Unison UK-C18
(4.6 mm in diameter×75 mm in length; manufactured by Imtakt Corp.)
Solvent: A: 10 mM aqueous ammonium formate solution containing 0.01% formic acid
B: acetonitrile containing 0.01% formic acid
A/B=equilibration with 5/5 followed by linear gradient for 7 minutes up to A/B=1/9
flow rate: 1.0 ml/min
detection: ultraviolet absorption λ=230 nm
retention time: 4.3 minutes (terpenoid derivative (I))
4.9 minutes (terpenoid derivative (III)).

To 42.6 L of the culture solution obtained in paragraph (1), an equal amount of acetone was added, and the mixture was well stirred and then allowed to stand overnight at room temperature. Then, the mycelia was removed by filtration under reduced pressure to obtain 78 L of a filtrate. This filtrate was applied to a Sepabeads SP207 (2 L; manufactured by Mitsubishi Chemical Corp.) column washed in advance with acetone and then buffer-replaced with water. The column was washed with 6 L of a mixed solvent of acetone:water=5:5 and subsequently with 6 L of a mixed solvent of acetone:water=6:4, followed by elution with 6 L of a mixed solvent of acetone:water=7:3. To this eluate containing the compounds of interest, 1.2 L of water was added, and further 2.6 L of ethyl acetate was added for liquid-liquid distribution to separate an organic layer containing the compounds of interest. The organic layer was washed with saturated saline, then dried over anhydrous sodium sulfate, and then concentrated under reduced pressure to obtain 6.92 g of extracts containing terpenoid derivative (I) and terpenoid derivative (III). A 1.5 g aliquot of the extracts was dissolved in 5 ml of methanol. This solution was adsorbed onto ODS-A (7.5 g; manufactured by YMC Co., Ltd.), and a mini-column was packed with the resulting carrier and then applied to an ODS-A (100 g; manufactured by YMC Co., Ltd.) column equilibrated in advance with a mixed solvent of acetonitrile:water containing 0.01% formic acid=55:45, followed by elution at a flow rate of 15 ml/min with the same mixed solvent as above. The ultraviolet absorption of the compounds of interest was detected at a wavelength λ=230 nm. A peak appearing at a retention time of 42.0 minutes (terpenoid derivative (I)) and a peak appearing at a retention time of 50.0 minutes (terpenoid derivative (III)) were each separated 5 times. The fraction solutions of each compound were combined and concentrated under reduced pressure to obtain 192 mg of terpenoid derivative (I) as a colorless powder and 2.45 g of a pale yellow powder containing terpenoid derivative (III). 2.45 g of the pale yellow powder containing terpenoid derivative (III) was dissolved in 2 ml of acetonitrile. This solution was applied to a Sepabeads SP207SS (500 ml; manufactured by Mitsubishi Chemical Corp.) column buffer-replaced in advance with a mixed solvent of acetonitrile:water=55:45. The column was washed with 1,750 ml of a mixed solvent of acetonitrile:water=60:40, followed by elution with 2,340 ml of a mixed solvent of acetonitrile:water=65:35. A 1,200 ml aliquot, of the eluates, containing terpenoid derivative (III) with high purity was concentrated under reduced pressure and subsequently lyophilized to obtain 2.19 g of terpenoid derivative (III).

Example 3

Production of Terpenoid Derivative (II) and Terpenoid Derivative (III) (Strain for Biotransformation: SANK 70214)

[Formula 9]

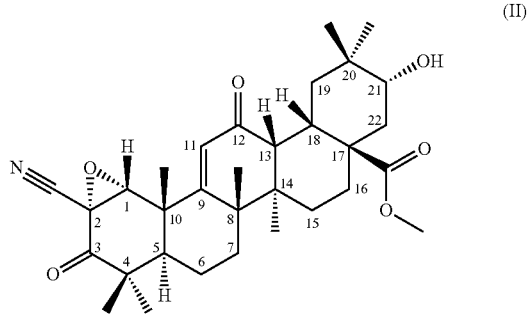

(II)

[Formula 10]

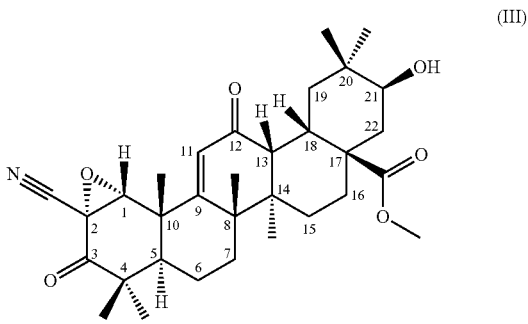

(III)

(1) Synthesis of Substrate Compound (2)

[Formula 11]

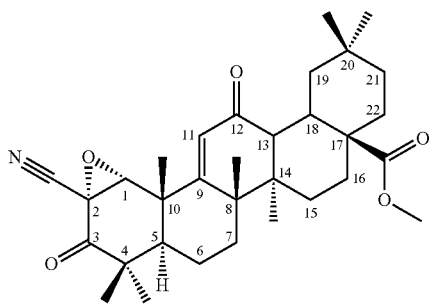

(2)

CDDO-Me (8.00 g, 15.8 mmol) was dissolved in dichloromethane (40 ml). To this solution, 3-chloroperbenzoic acid (>65%) (5.04 g, 19.0 mmol) was added under ice cooling, and the mixture was stirred at room temperature for 3 hours. To the reaction mixture, a saturated aqueous solution of sodium bicarbonate (40 ml) was added, and the mixture was stirred at the same temperature as above for 15 minutes. To this mixture, a 10% aqueous sodium thiosulfate solution (40 ml) was further added, and the resulting mixture was stirred at the same temperature as above for 5 minutes, followed by extraction with ethyl acetate. The separated organic layer was washed with saturated saline and dried over magnesium sulfate, and the solvent was evaporated off under reduced pressure. The residue was purified by silica gel column chromatography (n-hexane:ethyl acetate=4:1, v/v) to obtain substrate compound (2) (8.16 g, 99%) as a white amorphous solid.

ESI-MS; m/z: 522 [M+H].

$^1$H-NMR (400M Hz, CDCl3) δ: 0.91 (3H, s), 1.01 (3H, s), 1.08 (3H, s), 1.12 (3H, s), 1.19(3H, s), 1.27 (3H, s), 1.55 (3H, s), 1.18-2.00 (15H, m), 2.94 (1H, d, J =4.9 Hz), 3.05 (1H, dt, J =13.8, 3.7 Hz), 3.70 (3H, s), 4.34 (1H, s), 6.07 (1H, s).

high-performance liquid chromatography:

purity: 99.0% column: Cosmosil 5C18-MS-II (6.0 mm in diameter ×150 mm in length; manufactured by Nacalai Tesque, Inc.) solvent: A: 10 mM aqueous ammonium acetate solution B: acetonitrile A/B =15/85 isocratic flow rate: 1.0 ml/min temperature: 40° C.

detection: ultraviolet absorption λ=254 nm retention time: 9.6 minutes.

(2) Culture of Strain of Genus *Bacillus* for Biotransformation 20 ml of a seed culture medium having the composition shown in Table 3 below was placed in each of twenty 100-ml Erlenmeyer flasks, sterilized at 121° C. for 30 minutes, and then cooled to room temperature. One loopful of colonies of SANK 70214 was inoculated to the medium in each flask and cultured for 24 hours under conditions of 28° C. and 210 rpm in a rotating shaker. Hereinafter, the obtained culture solution is referred to as "seed culture solution".

TABLE 3

| Composition of seed culture medium for SANK 70214 | |
|---|---|
| Glucose | 50 g |
| Soybean meal | 10 g |
| Meat extract | 4 g |
| Polypeptone | 4 g |
| Yeast extract (Difco) | 1 g |
| CaCO3 | 5 g |
| NaCl | 2.5 g |
| Antifoaming agent *1 | 0.5 ml |
| Ion-exchanged water | 1000 ml |

*1 Nissan Disfoam CB-442 (manufactured by NOF Corp.)
*2 pH was adjusted to 7.2 with NaOH or HCl before sterilization.

80 ml of a main culture medium having the composition shown in Table 2above was placed in each of 300 500-ml Erlenmeyer flasks, sterilized at 121° C. for 30 minutes, and then cooled to room temperature. 0.8 ml of a solution of substrate compound (2) (synthesized in paragraph (1)) dissolved at a concentration of 30 mg/ml in dimethyl sulfoxide was added to this culture solution in each flask. 0.8 ml of the seed culture solution of SANK 70214 was aseptically inoculated to the medium in each flask and cultured for 5 days under conditions of 28° C. and 210 rpm in a rotating shaker.

(3) Isolation of Terpenoid Derivative (II) and Terpenoid Derivative (III)

The behaviors of terpenoid derivative (II) and terpenoid derivative (III) in this Example were monitored by HPLC under conditions given below.

Column: Unison UK-C18

(4.6 mm in diameter×75 mm in length; manufactured by Imtakt Corp.)

solvent: A: 10 mM aqueous ammonium formate solution containing 0.01% formic acid B: acetonitrile containing 0.01% formic acid A/B=equilibration with 5/5 followed by linear gradient for 7 minutes up to A/B=1/9 flow rate: 1.0 ml/min detection: ultraviolet absorption λ=230 nm retention time: 5.4 minutes (terpenoid derivative (II))

4.9 minutes (terpenoid derivative (III)).

To 22.8 L of the culture solution obtained in paragraph (2), an equal amount of acetone was added, and the mixture was well stirred and then allowed to stand overnight at room temperature. Then, the bacterial cells were removed by filter press to obtain 42 L of a filtrate. This filtrate was applied to a Sepabeads SP207 (2 L; manufactured by Mitsubishi Chemical Corp.) column washed in advance with acetone and then buffer-replaced with water. The column was washed with 14 L of a mixed solvent of acetone:water=5:5 and subsequently with 6 L of a mixed solvent of acetone:water=6:4, followed by elution with 7.2 L of a mixed solvent of acetone:water=7:3 and further elution with 8 L of a mixed solvent of acetone:water=8:2. From the fraction eluted with the mixed solvent of acetone:water=7:3, 4 L of the eluate containing the compound of interest was recovered. Sepabeads SP207SS (16 ml; manufactured by Mitsubishi Chemical Corp.) was added thereto. The organic solvent was evaporated off to adsorb the compound of interest onto the resin. The adsorbed matter was applied to a Sepabeads SP207SS (350 ml; manufactured by Mitsubishi Chemical Corp.) column washed in advance with acetone and then buffer-replaced with water. The column was washed with 1,200 ml of a mixed solvent of acetonitrile:water=50:50 and subsequently with 1,050 ml of a mixed solvent of acetonitrile:water=55:45, followed by elution with 2,950 ml of a mixed solvent of acetonitrile:water=60:40. The organic solvent in a 920 ml aliquot, of the eluates, containing terpenoid derivative (III) with high purity was evaporated off, and the residue was lyophilized to obtain 1.58 g of terpenoid derivative (III). Also, the organic solvent in a 580 ml aliquot, of the eluates, containing terpenoid derivative (II) was evaporated off, and the residue was lyophilized to obtain 120.7 mg of a powder containing terpenoid derivative (II). A 109 mg aliquot of this powder was dissolved in 1.0 ml of dimethyl sulfoxide. A 0.3 ml aliquot of this solution was applied to an HPLC column (Unison US-C18; 20 mm in diameter×150 mm in length; manufactured by Imtakt Corp.) equilibrated in advance with solvents of 0.01% aqueous formic acid solution:acetonitrile containing 0.01% formic acid=45:55, followed by elution at a flow rate of 20.0 ml/min with solvents of 0.01% aqueous formic acid solution:acetonitrile containing 0.01% formic acid=45:55. The ultraviolet absorption of the compound of interest was detected at a wavelength $\lambda$=230 nm. A peak appearing at a retention time of 13.6 minutes (terpenoid derivative (II)) was separated 3 times. The fraction solutions were combined and concentrated under reduced pressure, and the obtained suspension was lyophilized to obtain 4.5 mg of terpenoid derivative (II) as a colorless powder.

The steric structure of the obtained terpenoid derivative (II) of the present invention was determined using two-dimensional nuclear magnetic resonance spectroscopy (NOESY).

In the two-dimensional nuclear magnetic resonance spectroscopy (NOESY) of terpenoid derivative (II), the correlation was observed between the α-proton at the 19-position and the α-proton at the 21-position. Its steric structure was therefore determined as represented by the formula (II).

Measurement Values of Physicochemical Properties of Terpenoid Derivative (II)

1) appearance: a colorless powdery substance
2) molecular formula: $C_{32}H_{43}NO_6$
3) molecular weight: 537 (measured by ESI mass spectrometry)
4) the accurate mass, $[M+H]^+$, measured by high-resolution LC-ESI mass spectrometry is as given below:
   found: 538.31496
   calculated: 538.31631
5) $^1$H-nuclear magnetic resonance spectra: the $^1$H-nuclear magnetic resonance spectra (500 MHz) measured in deuterated chloroform referenced to 0.00 ppm using TMS are as given below:
   σ: 0.96 (3H, s), 1.06 (3H, s), 1.11 (3H, s), 1.12 (3H, s), 1.19 (3H, s), 1.27 (3H, s), 1.28 (3H, s), 1.46 (1H, d, J=13.0 Hz), 1.47 (1H, d, J=13.0 Hz), 1.52-1.59 (2H, m), 1.61-1.65 (2H, m), 1.66-1.69 (1H, m), 1.68-1.75 (1H, m), 1.75 (1H, dd, J=3.5 Hz, 14.5 Hz), 1.88 (1H, brd, J=14.5 Hz), 1.98 (1H, dd, J=5.5 Hz, 9.5 Hz), 2.03 (1H, dd, J=3.5 Hz, 14.5 Hz), 2.38 (1H, ddd, J=3.5 Hz, 14.0 Hz, 14.0 Hz), 2.99 (1H, d, J=4.5 Hz), 3.10 (1H, brd, J=13.5 Hz), 3.53 (1H, brs), 3.69 (3H, s), 4.34 (1H, s), 6.09 (1H, s) ppm.
6) $^{13}$C-nuclear magnetic resonance spectra: the $^{13}$C-nuclear magnetic resonance spectra (125 MHz) measured in deuterated chloroform referenced to 0.00 ppm using TMS are as given below:
   σ: 18.3 (t), 21.0 (q), 21.3 (q), 22.8 (q), 23.9 (q), 24.0 (q), 25.7 (t), 27.4 (q), 28.0 (q), 28.7 (t), 30.0 (t), 31.4 (t), 31.5 (d), 35.2 (s), 38.9 (t), 40.9 (s), 42.1 (s), 42.6 (d), 45.1 (s), 45.5 (s), 47.0 (s), 49.5 (d), 52.0 (q), 53.2 (s), 69.1 (d), 74.8 (d), 113.6 (s), 124.8 (d), 168.8 (s), 177.6 (s), 198.8 (s), 202.4 (s) ppm.
7) high-performance liquid chromatography: column: Unison UK-C18 (4.6 mm in diameter×75 mm in length; manufactured by Imtakt Corp.)
   solvent: A: 10 mM aqueous ammonium formate solution containing 0.01% formic acid
   B: acetonitrile containing 0.01% formic acid
   A/B=equilibration with 5/5 followed by linear gradient for 7 minutes up to A/B=1/9
   flow rate: 1.0 ml/min
   temperature: 40° C.
   detection: ultraviolet absorption $\lambda$=230 nm
   retention time: 5.4 minutes.
8) The $^1$H-nuclear magnetic resonance spectra of terpenoid derivative (II) are shown in FIG. 4, and the two-dimensional nuclear magnetic resonance spectra ($^1$H-$^{13}$C HSQC spectra) thereof are shown in FIG. 5. As a result of analyzing the $^1$H-nuclear magnetic resonance spectra and the two-dimensional nuclear magnetic resonance spectra ($^1$H-$^{13}$C HSQC spectra), each proton was attributed as follows:
   α-proton at the 19-position: 1.47 ppm (methylene)
   α-proton at the 21-position: 3.53 ppm (methine)
9) The two-dimensional nuclear magnetic resonance spectra ($^1$H-$^1$H NOESY spectra) of terpenoid derivative (II) are shown in FIG. 6. In FIG. 6, the correlation was observed between the α-proton at the 19-position and the α-proton at the 21-position. Its steric structure was therefore determined as represented by (II).

Example 4

Production of Terpenoid Derivative (III) (Strain for Biotransformation: SANK 70314)

(1) Culture of Strain of Genus *Bacillus* for Biotransformation 20 ml of a Trypto-Soy Broth medium (hereinafter, referred to as a TSB medium) given below was placed as a seed culture medium in a 100-ml Erlenmeyer flask, sterilized at 121° C. for 15 minutes, and then cooled to room temperature. One loopful of colonies of SANK 70314 was inoculated to the medium in the flask and cultured for 24 hours under conditions of 28° C. and 210 rpm in a rotating shaker. Hereinafter, the obtained culture solution is referred to as "seed culture solution".

<TSB Medium (Trypto-Soy Broth Medium)>

| | |
|---|---|
| Pearlcore Trypto-Soy Broth Eiken (manufactured by Eiken Chemical Co., Ltd.) | 30 g |
| Distilled water | 1,000 ml |

100 ml of a TSB medium was placed as a main culture medium in a 500-ml Erlenmeyer flask, sterilized at 121° C. for 15 minutes, and then cooled to room temperature. 1.0 ml of a solution of substrate compound (2) (synthesized by the method described in Example 3(1)) dissolved at a concentration of 30 mg/ml in dimethyl sulfoxide was added to this culture solution in the flask. 1.0 ml of the seed culture solution of SANK 70314 was aseptically inoculated to the medium in the flask and cultured for 3 days under conditions of 37° C. and 210 rpm in a rotating shaker.

(2) Isolation of Terpenoid Derivative (III)

The behavior of terpenoid derivative (III) in this Example was monitored by HPLC under conditions given below.

Column: Unison UK-C18
(4.6 mm in diameter×75 mm in length; manufactured by Imtakt Corp.)
solvent: A: 10 mM aqueous ammonium formate solution containing 0.01% formic acid
B: acetonitrile containing 0.01% formic acid
A/B=equilibration with 5/5 followed by linear gradient for 7 minutes up to A/B=1/9
flow rate: 1.0 ml/min
detection: ultraviolet absorption λ=230 nm
retention time: 4.9 minutes (terpenoid derivative (III)).

The culture solution obtained in paragraph (1) was diluted to 100 ml. Then, 100 ml of acetone was added thereto, and the mixture was left standing at room temperature for 1 hour. A 1 ml aliquot thereof was separated and centrifuged at 10000 rpm for 10 minutes. The supernatant was used as culture solution extracts.

10 µl of the culture solution extracts thus prepared was subjected to elution under the HPLC conditions described above. The ultraviolet absorption of the compound of interest was detected at a wavelength λ=230 nm. The transformation efficiency to substrate compound (2) was calculated from the peak area of a peak appearing at a retention time of 4.9 minutes (terpenoid derivative (III)). As a result, the biotransformation efficiency was confirmed to be 32% for terpenoid derivative (III).

Example 5

Cloning of SANK 70214 from Wild Strain (1) Preparation of Genomic DNA Sample of *Bacillus* sp. SANK 70214

100 ml of a medium composed of 3% Pearlcore Trypto-Soy Broth (manufactured by Eiken Chemical Co., Ltd.) (the pH was adjusted to 8.0 before autoclaving) (hereinafter, referred to as a TSB medium (pH 8.0)) was placed in a 500-ml Erlenmeyer flask, sterilized at 121° C. for 15 minutes, and then cooled to room temperature. One loopful of SANK 70214 was inoculated to the medium in the flask and cultured for 15.5 hours under conditions of 28° C. and 210 rpm. The obtained culture solution was used as seed culture. 100 ml of a TSB medium (pH 8.0) was placed in a 500-ml Erlenmeyer flask, sterilized at 121° C. for 15 minutes, and then cooled to room temperature. 1 ml of the seed culture solution of SANK 70214 was aseptically inoculated to the medium in the flask and cultured for 8 hours under conditions of 28° C. and 210 rpm. 40 ml of the obtained culture solution was dispensed to each 50-ml conical tube and centrifuged at 6,000 rpm for 10 minutes to recover bacterial cells. Genomic DNA was prepared therefrom.

(2) Genome Sequencing and Identification of P450 Gene

Genome sequencing was carried out at the Technology Research Association for Next generation natural products chemistry using PacBio RS II (manufactured by Pacific Biosciences of California, Inc.) and Miseq (manufactured by Illumina, Inc.). The obtained sequence was 4.0 Mbp with a GC content of 40.8%. The obtained genomic sequence was annotated using BASys Server 2 (https://www.basys.ca/server2/basys/cgi/text_search.pl) with *Bacillus halodurans* as a reference sequence to obtain one putative P450 nucleotide sequence (nucleotide sequence of a protein of SANK 70214 having hydroxylation activity) (SEQ ID NO: 3, FIG. 9). The obtained nucleotide sequence retained 3 types of motifs described in Bioorganic & Medicinal Chemistry Letters, 2012 1; 22 (1): 606-609. Accordingly, the gene of the protein (SEQ ID NO: 5, FIG. 11) having the activity of hydroxylating substrate compound (2) into terpenoid derivative (III) of the present invention was cloned.

(3) Cloning into *Escherichia coli*

In order to amplify the nucleotide sequence of P450 of SANK 70214 by PCR, a primer set of F1 (GAAGGAGATATACATATGAGTCATGCTGCGAACG) and R1 (TGTCGACGGAGCTCTTTAGAATGAAACGGGCAATG) was prepared. PCR reaction was performed using this primer set and SANK 70214 as a template. The PCR reaction employed PrimeSTAR Max (manufactured by Takara Bio Inc.) and a PCR apparatus (manufactured by Takara Bio Inc., TP350), and 3-stage reaction involving denaturation at 98° C. for 10 seconds, annealing at 55° C. for 5 seconds, and elongation at 72° C. for 10 seconds was repeated 30 times. As a result, a DNA fragment having a length of approximately 1.2 kb was amplified. The obtained SANK 70214 DNA fragment of approximately 1.2 kb was treated with Cloning Enhancer (manufactured by Clontech Laboratories, Inc.) provided for In-Fusion cloning reaction. In order to amplify a vector pET21b for cloning and expression (manufactured by Novagen/EMD Biosciences, Inc.) by PCR, a primer set of F2 (ATGTATATCTCCTTCTTAAAGTTAAAC) and R2 (AGAGCTCCGTCGACAAGC) was prepared. PCR reaction was performed using this primer set and pET21b as a template. The PCR reaction employed PrimeSTAR Max (manufactured by Takara Bio Inc.) and a PCR apparatus (manufactured by Takara Bio Inc., TP600), and 3-stage reaction involving denaturation at 98° C. for 10 seconds, annealing at 55° C. for 5 seconds, and elongation at 72° C. for 60 seconds was repeated 30 times. As a result, a DNA fragment having a length of approximately 5 kb was amplified. This PCR reaction solution was subjected to agarose gel electrophoresis, and the DNA fragment of approximately 5 kb was excised and recovered using Monofas DNA Purification Kit I (manufactured by GL Sciences Inc.). The recovered pET21b DNA fragment of approximately 5 kb and the DNA fragment of approximately 1.2 kb in length treated in advance with Cloning Enhancer were ligated using In-Fusion HD Cloning kit (manufactured by Clontech Laboratories, Inc.) and used in the transformation of *Escherichia coli* DH5a (manufactured by Toyobo Co., Ltd.). Then, *Escherichia coli* was selected in an LB agar medium containing 100 µg/ml carbenicillin. Colonies of the obtained transformed *Escherichia coli* were cultured in an LB liquid medium containing 100 µg/ml carbenicillin. The grown *Escherichia coli* was recovered, and plasmid DNA was purified using QIAprep Spin Miniprep Kit (manufactured by Qiagen N.V.) to obtain a plasmid carrying the nucleotide sequence of the protein of SANK 70214 having hydroxylation activity (pET-SANK 70214-01).

(4) Cloning into *Bacillus subtilis* 168

In order to transform *Bacillus subtilis* 168 with the nucleotide sequence of the protein of SANK 70214 having hydroxylation activity, this nucleotide sequence was recloned into pHT01 (manufactured by MoBiTec GmbH), a shuttle vector of *Bacillus subtilis* and *Escherichia coli*.

In order to amplify the nucleotide sequence of P450 cloned in pET-SANK 70214-01 by PCR, a primer set of F3 (AAGGAGGAAGGATCCATGAGTCATGCTGCGAACGTAA) and R3 (GACGTCGACTCTAGATTAGAATGAAACGGGCAATG) was prepared. PCR reaction was performed using this primer set and pET-SANK 70214-01 as a template. The PCR reaction employed PrimeSTAR Max (manufactured by Takara Bio Inc.) and a PCR apparatus (manufactured by Takara Bio Inc., TP350), and 3-stage reaction involving denaturation at 98° C. for 10 seconds, annealing at 55° C. for 5 seconds, and elongation at 72° C.

for 10 seconds was repeated 30 times. As a result, a DNA fragment having a length of approximately 1.2 kb was amplified. The obtained SANK 70214 DNA fragment of approximately 1.2 kb was treated with Cloning Enhancer (manufactured by Clontech Laboratories, Inc.) provided for In-Fusion cloning reaction. In order to amplify pHT01 (manufactured by MoBiTec GmbH), a shuttle vector of *B. subtilis* and *Escherichia coli*, by PCR, a primer set of F4 (TCTAGAGTCGACGTCCCCG) and R4 (GGATCCTTC-CTCCTTTAATTG) was prepared. PCR reaction was performed using this primer set and pHT01 as a template. The PCR reaction employed PrimeSTAR Max (manufactured by Takara Bio Inc.) and a PCR apparatus (manufactured by Takara Bio Inc., TP350), and 3-stage reaction involving denaturation at 98° C. for 10 seconds, annealing at 55° C. for 5 seconds, and elongation at 72° C. for 60 seconds was repeated 30 times. As a result, a DNA fragment having a length of approximately 8 kb was amplified. This PCR reaction solution was subjected to agarose gel electrophoresis, and the DNA fragment of approximately 8 kb was excised and recovered using Monofas DNA Purification Kit I (manufactured by GL Sciences Inc.). The recovered pHT01 DNA fragment of approximately 8 kb and the DNA fragment of approximately 1.2 kb in length treated in advance with Cloning Enhancer were ligated using In-Fusion HD Cloning kit (manufactured by Clontech Laboratories, Inc.) and used in the transformation of *Escherichia coli* DH5α (manufactured by Toyobo Co., Ltd.). Then, *Escherichia coli* was selected in an LB agar medium containing 100 µg/ml carbenicillin. Colonies of the obtained transformed *Escherichia coli* were cultured in an LB liquid medium containing 100 µg/ml carbenicillin. The grown *Escherichia coli* was recovered, and plasmid DNA was purified using QIAprep Spin Miniprep Kit (manufactured by Qiagen N.V.) to obtain a plasmid carrying the nucleotide sequence of the protein of SANK 70214 having hydroxylation activity (pHT01-SANK 70214-01). *Escherichia coli* C600 (manufactured by Zymo Research Corp.) was transformed with the obtained pHT01-SANK 70214-01 for transformation of *B. subtilis*. Then, *Escherichia coli* was selected in an LB agar medium containing 100 µg/ml carbenicillin. Colonies of the obtained transformed *Escherichia coli* were cultured in an LB liquid medium containing 100 µg/ml carbenicillin. The grown *Escherichia coli* was recovered, and plasmid DNA was purified using QIAprep Spin Miniprep Kit (manufactured by Qiagen N.V.) to obtain pHT01-SANK 70214-01 for the transformation of *Bacillus subtilis*. *B. subtilis* 168 was transformed with pHT01-SANK 70214-01 by electroporation. *B. subtilis* was selected in an LB agar medium containing 100 µg/ml chloramphenicol. *B. subtilis* carrying pHT01-SANK 70214-01 was obtained. This transformant was designated as *B. subtilis* SANK 70214T.

Example 6

Cloning of SANK 70314 from Wild Type (1) Preparation of Genomic DNA Sample of *Bacillus megaterium* SANK 70314

The genomic DNA sample of SANK 70314 was prepared in the same way as in Example 5 except that SANK 70314 was used instead of SANK 70214 and the culture time of the seed culture solution of SANK 70314 was set to 6 hours.

(2) Genome Sequencing and Identification of P450 Gene

The genome sequencing was carried out using PacBio RS II (manufactured by Pacific Biosciences of California, Inc.) and Miseq (manufactured by Illumina, Inc.). The obtained sequence was 5.4 Mbp with a GC content of 38.0%. The obtained genomic sequence was annotated using BASys Server 2 (https://www.basys.ca/server2/basys/cgi/text_search.pl) with *B. megaterium* as a reference sequence to obtain six putative P450 nucleotide sequences (nucleotide sequences of proteins of SANK 70314 having hydroxylation activity). The obtained nucleotide sequences of P450 each retained 3 types of motifs described in Bioorganic & Medicinal Chemistry Letters, 2012 1; 22 (1): 606-609. Among them, the gene of the protein (SEQ ID NO: 6, FIG. 12) having the activity of hydroxylating substrate compound (2) into terpenoid derivative (III) of the present invention was cloned (SEQ ID NO: 4, FIG. 10).

(3) Cloning into *Escherichia coli*

In order to amplify the nucleotide sequence of P450 of SANK 70314 by PCR, a primer set of F5 (GAAGGAGA-TATACATATGAAAACCGAAAGAGAAAAC) and R5 (TGTCGACGGAGCTCTTATACATGTTTACGAATCA) was prepared. PCR reaction was performed using this primer set and SANK 70314 as a template.

The subsequent procedures were performed in the same way as in Example 5 to obtain a plasmid carrying the nucleotide sequence of the protein of SANK 70314 having hydroxylation activity (pET-SANK 70314-01).

(4) Cloning into *Bacillus subtilis* 168

In order to transform *Bacillus subtilis* 168 with the nucleotide sequence of the protein of SANK 70314 having hydroxylation activity, this nucleotide sequence was recloned into pHT01 (manufactured by MoBiTec GmbH), a shuttle vector of *B. subtilis* and *Escherichia coli*.

In order to amplify the nucleotide sequence of P450 cloned in pET-SANK 70314-01 by PCR, a primer set of F6 (AAGGAGGAAGGATCCATGAAAACCGAAAGA-GAAAAC) and R6 (GACGTCGACTCTAGATTATACAT-GTTTACGAATCAATAATTC) was prepared. PCR reaction was performed using this primer set and pET-SANK 70314-01 as a template. The PCR reaction employed PrimeSTAR Max (manufactured by Takara Bio Inc.) and a PCR apparatus (manufactured by Takara Bio Inc., TP350), and 3-stage reaction involving denaturation at 98° C. for 10 seconds, annealing at 55° C. for 5 seconds, and elongation at 72° C. for 10 seconds was repeated 30 times. As a result, a DNA fragment having a length of approximately 1.2 kb was amplified. The obtained SANK 70314 DNA fragment of approximately 1.2 kb was treated with Cloning Enhancer (manufactured by Clontech Laboratories, Inc.) provided for In-Fusion cloning reaction. In order to amplify pHT01 (manufactured by MoBiTec GmbH), a shuttle vector of *Bacillus subtilis* and *Escherichia coli*, by PCR, a primer set of F4 (TCTAGAGTCGACGTCCCCG) and R4 (GGATC-CTTCCTCCTTTAATTG) was utilized. PCR reaction was performed using this primer set and pHT01 as a template. The PCR reaction employed PrimeSTAR Max (manufactured by Takara Bio Inc.) and a PCR apparatus (manufactured by Takara Bio Inc., TP350), and 3-stage reaction involving denaturation at 98° C. for 10 seconds, annealing at 55° C. for 5 seconds, and elongation at 72° C. for 60 seconds was repeated 30 times. As a result, a DNA fragment having a length of approximately 8 kb was amplified. This PCR reaction solution was subjected to agarose gel electrophoresis, and the DNA fragment of approximately 8 kb was excised and recovered using Monofas DNA Purification Kit I (manufactured by GL Sciences Inc.). The recovered pHT01 DNA fragment of approximately 8 kb and the DNA fragment of approximately 1.2 kb in length treated in advance with Cloning Enhancer were ligated using In-Fusion HD Cloning kit (manufactured by Clontech Laboratories, Inc.)

and used in the transformation of *Escherichia coli* DH5α (manufactured by Toyobo Co., Ltd.). Then, *Escherichia coli* was selected in an LB agar medium containing 100 μg/ml carbenicillin. Colonies of the obtained transformed *Escherichia coli* were cultured in an LB liquid medium containing 100 μg/m1 carbenicillin. The grown *Escherichia coli* was recovered, and plasmid DNA was purified using QIAprep Spin Miniprep Kit (manufactured by Qiagen N.V.) to obtain a plasmid carrying the nucleotide sequence of the protein of SANK 70314 having hydroxylation activity (pHT01-SANK 70314-01). *Escherichia coli* C600 (manufactured by Zymo Research Corp.) was transformed with the obtained pHT01-SANK 70314-01 for transformation of *B. subtilis*. Then, *Escherichia coli* was selected in an LB agar medium containing 100 μg/ml carbenicillin. Colonies of the obtained transformed *Escherichia coli* were cultured in an LB liquid medium containing 100 μg/ml carbenicillin. The grown *Escherichia coli* was recovered, and plasmid DNA was purified using QIAprep Spin Miniprep Kit (manufactured by Qiagen N.V.) to obtain pHT01-SANK 70314-01 for the transformation of *B. subtilis*. *B. subtilis* 168 was transfected with pHT01-SANK 70314-01 by electroporation. *B. subtilis* was selected in an LB agar medium containing 100 μg/ml chloramphenicol. *B. subtilis* carrying pHT01-SANK 70314-01 was obtained. This transformant was designated as *B. subtilis* SANK 70314T.

Example 7

Production of Terpenoid Derivative (III) (Strain for Biotransformation: SANK 70214T)

(1) Culture of SANK 70214T 20 ml of a seed culture medium having the composition shown in Table 4 below was placed in a 100-ml Erlenmeyer flask, sterilized at 121° C. for 15 minutes, and then cooled to room temperature. One loopful of colonies of SANK 70214T was inoculated to the medium in the flask and cultured for 24 hours under conditions of 37° C. and 210 rpm in a rotating shaker. Hereinafter, the obtained culture solution is referred to as "seed culture solution".

TABLE 4

| Composition of seed culture medium for SANK 70214T | |
|---|---|
| Difco 2 x YT broth (manufactured by Becton, Dickinson and Company) | 31 g |
| Ion-exchanged water | 1000 ml |

* pH was unadjusted.

100 ml of main culture medium-1 having the composition shown in Table 5 below was placed in a 500-ml Erlenmeyer flask and sterilized at 121° C. for 30 minutes. Then, main culture medium-2 having the composition shown in Table 6 below was aseptically added thereto to prepare a main culture medium. 1.0 ml of the seed culture solution of SANK 70214T was aseptically inoculated thereto and cultured for 2 hours under conditions of 37° C. and 210 rpm in a rotating shaker. Then, IPTG (isopropyl-β-thiogalactopyranoside) was added thereto at 0.1 mM (final concentration), and the mixture was cultured for 1 hour under conditions of 37° C. and 210 rpm in a rotating shaker. Then, 1.0 ml of a solution of substrate compound (2) (synthesized by the method of Example 3(1)) dissolved at a concentration of 30 mg/ml in dimethyl sulfoxide was added thereto, and the mixture was cultured for 5 hours under conditions of 37° C. and 210 rpm in a rotating shaker.

TABLE 5

| Composition of main culture medium - 1 | |
|---|---|
| Bacto Tryptone (manufactured by Becton, Dickinson and Company) | 10 g |
| Bacto Yeast Extract (manufactured by Becton, Dickinson and Company) | 5 g |
| Anhydrous disodium hydrogen phosphate | 6.78 g |
| Potassium dihydrogen phosphate | 3 g |
| Sodium chloride | 5.5 g |
| Ammonium chloride | 1 g |
| Hydroxypropyl-β-cyclodextrin | 30 g |
| Glycerol | 20 g |
| Ion-exchanged water | 1000 ml |

TABLE 6

| Composition of main culture medium - 2 | |
|---|---|
| 100 mM ferrous sulfate | 1 ml |
| 80 mg/ml 5-aminolevulinic acid | 1 ml |
| 2 mg/ml thymine | 10 ml |
| 100 mg/ml chloramphenicol | 1 ml |

(2) Isolation of Terpenoid Derivative (III)

The behavior of terpenoid derivative (III) in this Example was monitored by HPLC under conditions given below.
column: Unison UK-C18
(4.6 mm in diameter×75 mm in length; manufactured by Imtakt Corp.)
solvent: A: 10 mM aqueous ammonium formate solution containing 0.01% formic acid
B: acetonitrile containing 0.01% formic acid
A/B=equilibration with 5/5 followed by linear gradient for 7 minutes up to A/B=1/9
flow rate: 1.0 ml/min
detection: ultraviolet absorption λ230 nm
retention time: 4.9 minutes (terpenoid derivative (III))

The culture solution obtained in paragraph (1) was diluted to 100 ml. Then, 100 ml of acetone was added thereto, and the mixture was left standing at room temperature for 1 hour. A 1 ml aliquot thereof was separated and centrifuged at 10,000 rpm for 10 minutes. The supernatant was used as culture solution extracts.

10 μl of the culture solution extracts thus prepared was subjected to elution under the HPLC conditions described above. The ultraviolet absorption of the compound of interest was detected at a wavelength λ=230 nm. The transformation efficiency to substrate compound (2) was calculated from the peak area of a peak appearing at a retention time of 4.9 minutes (terpenoid derivative (III)). As a result, the biotransformation efficiency was confirmed to be 77% for terpenoid derivative (III).

Example 8

Production of Terpenoid Derivative (III) (Strain for Biotransformation

SANK 70314T)

(1) Culture of SANK 70314T 20 ml of a seed culture medium having the composition shown in Table 4 of Example 7 was placed in a 100-ml Erlenmeyer flask, sterilized at 121° C. for 15minutes, and then cooled to room temperature. One loopful of colonies of SANK 70314T was inoculated to the medium in the flask and cultured for 10 hours under conditions of 37° C. and 210 rpm in a rotating shaker. Hereinafter, the obtained culture solution is referred to as "seed culture solution".

100 ml of main culture medium-1 having the composition shown in Table 5 of Example 7 was placed in a 500-ml Erlenmeyer flask and sterilized at 121° C. for 15 minutes. Then, main culture medium-2 having the composition shown in Table 6 above was aseptically added thereto to prepare a main culture medium. 1.0 ml of the seed culture solution of SANK 70314T was aseptically inoculated thereto and cultured for 2 hours under conditions of 37° C. and 210 rpm in a rotating shaker. Then, IPTG was added thereto at 0.1 mM (final concentration), and the mixture was cultured for 1 hour under conditions of 37° C. and 210 rpm in a rotating shaker. Then, 1.0 ml of a solution of substrate compound (2) (synthesized by the method of Example 3(1)) dissolved at a concentration of 30 mg/ml in dimethyl sulfoxide was added thereto, and the mixture was cultured for 84 hours under conditions of 37° C. and 210 rpm in a rotating shaker.

(2) Isolation of Terpenoid Derivative (III)

The behavior of terpenoid derivative (III) in this Example was monitored by HPLC under conditions given below.

column: Unison UK-C18
(4.6 mm in diameter×75 mm in length; manufactured by Imtakt Corp.)
solvent: A: 10 mM aqueous ammonium formate solution containing 0.01% formic acid
B: acetonitrile containing 0.01% formic acid
A/B=equilibration with 5/5 followed by linear gradient for 7 minutes up to A/B=1/9
flow rate: 1.0 ml/min
detection: ultraviolet absorption λ=230 nm
retention time: 4.9 minutes (terpenoid derivative (III)).

The culture solution obtained in paragraph (1) was diluted to 100 ml. Then, 100 ml of acetone was added thereto, and the mixture was left standing at room temperature for 1 hour. A 1 ml aliquot thereof was separated and centrifuged at 10,000 rpm for 10 minutes. The supernatant was used as culture solution extracts.

10 μl of the culture solution extracts thus prepared was subjected to elution under the HPLC conditions described above. The ultraviolet absorption of the compound of interest was detected at a wavelength λ=230 nm. The transformation efficiency to RNR-0014 was calculated from the peak area of a peak appearing at a retention time of 4.9 minutes (terpenoid derivative (III)). As a result, the biotransformation efficiency was confirmed to be 39% for terpenoid derivative (III).

Example 9

Production of Microspheres as Sustained-Release Pharmaceutical Composition

Terpenoid derivative (III) of the present invention was used as an active ingredient in the sustained-release pharmaceutical composition. Polylactic acid or poly(lactic-co-glycolic acid) (manufactured by Wako Pure Chemical Industries, Ltd.) shown in Table 7 was used as a base material.

TABLE 7

| Base material | Copolymerization ratio (glycolic acid/lactic acid) | Molecular weight |
|---|---|---|
| PLA-0005 | 0/100 | 5000 |
| PLA-0020 | 0/100 | 20000 |
| PLGA-5020 | 50/50 | 20000 |
| PLGA-7520 | 75/25 | 20000. |

Microspheres having a drug content of 10% by weight were produced by the following method: the base material and terpenoid derivative (III) of the present invention were dissolved at concentrations of approximately 17% and approximately 1.7% (w/v), respectively, in dichloromethane. Subsequently, the obtained solution was further added into a 0.05% aqueous polyvinyl alcohol solution, and an o/w emulsion was formed using a stirrer. In this emulsion, the volume of the aqueous phase was approximately 6.7 times the volume of the oil phase.

The particle size of the obtained microspheres was controlled by appropriately adjusting the stirring speed for the formation of the o/w emulsion. For example, the obtained microspheres had a small particle size by a large number of revolutions and had a large particle size by a small number of revolutions.

The solvent in the oil phase was evaporated by the adoption of the drying method in water (o/w method). This evaporation was performed at normal pressure with stirring using a magnetic stirrer. The microspheres thus obtained were separated by filtration. Then, the emulsifier, etc., attached on the surface of the microspheres was washed off several repetitive times with purified water or the like. Then, the microspheres were dispersed again in distilled water (purified water) and lyophilized to obtain the microspheres of interest.

Microspheres having a drug content of 30% by weight were produced by the following method: the base material and terpenoid derivative (III) of the present invention were dissolved at concentrations of approximately 12% and approximately 5% (w/v), respectively, in dichloromethane. Subsequently, the obtained solution was further added into a 0.05% aqueous polyvinyl alcohol solution, and an o/w emulsion was formed using a stirrer. In this emulsion, the volume of the aqueous phase was approximately 6.7 times the volume of the oil phase.

The average particle sizes of the obtained microspheres were measured using a laser diffraction particle size distribution measurement apparatus (Helos & Cuvette, Sympatec GmbH). The measurement results are shown in Table 8.

TABLE 8

Particle size distribution measurement results

| Base material | Drug content (wt %) | $X_{10}$ | $X_{50}$ | $X_{90}$ |
|---|---|---|---|---|
| PLGA-0005 | 10 | 3.70 | 14.4 | 24.3 |
| PLGA-5020 | 10 | 6.52 | 16.9 | 27.4 |
| PLGA-5020 | 30 | 5.88 | 17.1 | 27.8 |
| PLGA-7520 | 10 | 11.1 | 27.9 | 41.6 |
| PLA-0020 | 10 | 5.41 | 17.3 | 27.3 |

The content of terpenoid derivative (III) of the present invention in the obtained microspheres (weight fraction of the drug in the drug-containing microspheres) was measured by the method given below.

The produced microspheres (approximately 1 mg was accurately weighed) were dissolved in dimethyl sulfoxide to accurately make 1 mL. The amount of terpenoid derivative (III) of the present invention contained in this solution was calculated from a measurement value of high-performance liquid chromatography (HPLC). The content of terpenoid derivative (III) of the present invention in the microspheres was calculated according to the following expression:

Content (% by weight)=(Measurement value of the amount of terpenoid derivative (III) of the present invention contained/Amount of the microspheres)×100.

The HPLC conditions are as follows:
<HPLC Conditions>
apparatus: chromatograph (Acquity, Waters Corp.), UV detector (Acquity, Waters Corp.), data analyzer (Empower, Waters Corp.)
HPLC column: ACQUITY UPLC BEH C18 1.7 µm (2.1 mm I.D.×50 mm, Waters Corp.)
analysis time: 14 min
mobile phase A: water:acetonitrile:phosphoric acid (95:5: 0.1)
mobile phase B: acetonitrile:water:phosphoric acid (95:5: 0.1)
flow rate: 0.75 mL/min (gradient conditions are shown in Table 9)
column temperature: constant temperature of approximately 40° C.
sample temperature: constant temperature of approximately 25° C.
detection wavelength: UV-245 nm.

TABLE 9

| | Gradient conditions | | | | | | |
|---|---|---|---|---|---|---|---|
| | Time (min) | | | | | | |
| | 0 | 0.5 | 3.5 | 6.0 | 11.0 | 11.1 | 14.0 |
| Mobile phase A (%) | 80 | 80 | 50 | 50 | 1 | 80 | 80 |
| Mobile phase B (%) | 20 | 20 | 50 | 50 | 99 | 20 | 20 |

The drug content determined by this method was 85% to 95% of the weight ratio calculated from the composition of the base material and the drug at the time of the microsphere production and was thus confirmed to be quantitative. Accordingly, in the present invention, a drug content calculated from the composition at the time of production was indicated for the composition for the sake of convenience.

Example 10

Production of Rod-shaped Implant as Sustained-release Pharmaceutical Composition A rod-shaped implant was produced using microspheres containing PLA-0020 as the base material and 10% by weight of terpenoid derivative (III) of the present invention. The microspheres were able to be completely melted by heating to approximately 200° C. A metal tube was filled with the melted microspheres and allowed to cool. Then, the resulting product was taken out thereof and completely cooled to obtain the rod-shaped implant of interest (diameter: approximately 1 mm).

The obtained rod-shaped implant was dissolved in dimethyl sulfoxide to accurately make 1 mg/mL. The amount of terpenoid derivative (III) contained in this solution was measured in the same way as in Example 4 to calculate the content of terpenoid derivative (III) in the rod-shaped implant.

The microspheres having a drug content of 10% by weight, used in this Example, were produced by the following method: the base material and terpenoid derivative (III) of the present invention were dissolved at concentrations of approximately 17% and approximately 1.7% (w/v), respectively, in dichloromethane. Subsequently, the obtained solution was further added into a 0.05% aqueous polyvinyl alcohol solution, and an o/w emulsion was formed using a stirrer. In this emulsion, the volume of the aqueous phase was approximately 6.7 times the volume of the oil phase.

Test Example 1

NQO1 Assay

Hepa1c1c7 cells (mouse hepatic cell line, ATCC, catalog No. CRL-2026) were cultured (5% $CO_2$, 37° C.). A DMEM (Life Technologies Japan Ltd., catalog No. 11965-092) medium also containing 10% inactivated FBS was used. The medium contained 100 units/mL (final concentration) penicillin and 100 ug/mg (final concentration) streptomycin. The NQO1 assay was conducted according to previous reports (Anal Biochem 1998; 169: 328; and Methods Enzymol 2004; 382: 243).

The Hepa1c1c7 cells were seeded at 10000 cells/well in a 96-well plate. Approximately 24 hours later, the medium was replaced with a medium containing terpenoid derivative (III), terpenoid derivative (I), or terpenoid derivative (II), and the culture was further performed for approximately 48 hours. A lysis solution (a solution containing 2 mM EDTA and 0.8% digitonin), a reaction solution (a solution containing 0.025 M of tris-HCl, 0.067% of albumin, 0.01% of Tween-20, 2 U/mL of glucose-6-phosphate dehydrogenase, 5 µM of flavin adenine dinucleotide, 1 µM of glucose-6-phosphate, 30 µM of nicotinamide adenine dinucleotide phosphate, 0.03% of 3-(4, 5-dimethyl-2-thiazolyl)-2,5-diphenyltetrazolium bromide (MTT), and 50 µM of menadione), and a stop solution (a solution containing 0.3 mM dicumarol and 5 mM potassium dihydrogen phosphate, pH 7.4) were prepared. After removal of the medium, 50 µL of the lysis solution was added thereto, and the mixture was left standing at 37° C. for 10 minutes. The reaction mixture was further shaken at room temperature for 10 minutes.

Two hundred uL of the solution was added thereto, and the mixture was left standing at room temperature for 5 minutes. Fifty µL of the stop solution was added thereto, and the absorbance at 490 nm was measured.

The test results were analyzed using Prism (GraphPad Software, Inc., Ver. 5) to calculate the CD value (concentration of double NQO1 activity) of the concentration at which the activity of NQO1 was increased 2-fold. Each group consisted of 3 wells and indicated as a mean of CD values. The CD values were 1.0 nM for terpenoid derivative (III), 0.3 nM for terpenoid derivative (I), and 0.1 nM for terpenoid derivative (II).

Test Example 2

In Vitro Drug Release Test of Microspheres Containing Terpenoid Derivative (III)

Microspheres containing 10% by weight of terpenoid derivative (III) of the present invention were produced by the method described in Example 7. An intraocular irrigating solution (Opeguard MA, manufactured by Senju Pharmaceutical Co., Ltd.) was allowed to contain 1 w/v % of a surfactant (Tween 80). To this solution, the microspheres were added such that the concentration of terpenoid derivative (III) of the present invention was 50 μg/mL. The mixture was stirred in an incubator set to 37° C. 1, 2, 3, and 7 days after the start of incubation, this mixed solution was centrifuged (3,750 rpm, 10 minutes), and 200 μL of the obtained supernatant was mixed with 800 μL of 50% acetonitrile. The amount of terpenoid derivative (III) of the present invention dissolved was measured by HPLC. The HPLC conditions were the same as those described in Example 4.

The rate of dissolution (%) of terpenoid derivative (III) of the present invention was calculated when the drug concentration of the completely dissolved terpenoid derivative (III) of the present invention was defined as 100%.

The calculation results are shown in Table 10. These results demonstrated that all of the tested microspheres release the drug in a sustained manner.

TABLE 10

Cumulative rate of dissolution (%) of terpenoid derivative (III) of present invention from microsphere

| Base material Day | PLA-0005 (10 wt %*) | PLGA-7520 (10 wt %*) | PLA-0020 (10 wt %*) |
|---|---|---|---|
| 1 | 91 | 5 | 4 |
| 2 | 102 | 9 | 6 |
| 3 | 104 | 12 | 7 |
| 7 | 104 | 26 | 13 |

| Day | PLGA-5020 (10 wt %*) | PLGA-5020 (30 wt %*) |
|---|---|---|
| 1 | 19 | 19 |
| 2 | 38 | 30 |
| 3 | 58 | 41 |
| 7 | 93 | 75 |

*shows the content of terpenoid derivative (III) in the pharmaceutical composition.

Test Example 3

In Vitro Drug Release Test of Rod-shaped Implant Containing Terpenoid Derivative (III)

A rod-shaped implant was produced by the production method described in Example 8. An intraocular irrigating solution (Opeguard MA, manufactured by Senju Pharmaceutical Co., Ltd.) was allowed to contain 1 w/v % of a surfactant (Tween 80). To this solution, the rod-shaped implant was added such that the concentration of terpenoid derivative (III) of the present invention was 50 μg/mL. The mixture was stirred in an incubator set to 37° C. 1, 2, 3, 7, 14, 21, and 28 days after the start of incubation, this mixed solution was centrifuged (3,750 rpm, 10 minutes), and 200 μL of the obtained supernatant was mixed with 800 μL of 50% acetonitrile. The amount of terpenoid derivative (III) of the present invention dissolved was measured by HPLC. The HPLC conditions were the same as those described in Example 7. The method for calculating the rate of dissolution was the same as in Test Example 2.

The calculation results are shown in Table 11. These results demonstrated that the rod-shaped implant having the base material PLGA-5020 releases the drug in a sustained manner.

TABLE 11

Cumulative rate of dissolution (%) of terpenoid derivative (III) of present invention from rod-shaped implant (content of terpenoid derivative (III): 10% by weight)

| Day | PLGA-5020 |
|---|---|
| 1 | 0 |
| 2 | 0 |
| 3 | 0 |
| 7 | 4 |
| 15 | 30 |
| 21 | 61 |
| 30 | 84. |

Test Example 4

Pharmacokinetic Test of Microspheres Containing Terpenoid Derivative (III) in Rabbit Eye Suspensions were prepared using each of terpenoid derivative (III) of the present invention, terpenoid derivative (III) of the present invention-PLA-0005 [prepared by using PLA-0005 as the base material and adjusting the mixing ratio of terpenoid derivative (III) of the present invention and PLA-0005 to 1:9], and terpenoid derivative (III) of the present invention-PLA-0020 [prepared by using PLA-0020 as the base material and adjusting the mixing ratio of terpenoid derivative (III) of the present invention and PLA-0020 to 1:9], and saline as a solvent such that the concentration of terpenoid derivative (III) was 3 mM.

50 μL each of the suspensions was intravitreally administered to each white rabbit (Oriental Yeast Co., Ltd., Kbl: NZW, male, 8 weeks old). After the intravitreal administration, the rabbit was euthanized, and the intravitreal fluid and the retina were sampled. The concentration of terpenoid derivative (III) contained in these samples was measured. The results are shown in Tables 13 and 14. The numeric values shown in Table 12 below are indicated by a mean from 4 eyes and standard deviation. The drug concentration in each tissue was measured by LC/MS/MS. The tissue was pretreated by dilution with purified water in an amount corresponding to 10 times the weight of the tissue and subsequent homogenization to obtain a measurement sample. A water/acetonitrile (1:1) solution containing an internal standard solution (IS; niflumic acid) was added to the obtained sample to extract the drug. Then, the solution was filtered through a filter and injected to LC/MS/MS.

The LC/MS/MS conditions were as follows:
<UPLC conditions>: Waters Acquity UPLC
analysis column: ACQUITY UPLC BEH C18 1.7 μm
column temperature: 50° C.
mobile phase A: 95% acetonitrile (5 mM ammonium acetate)
mobile phase B: 5% acetonitrile (5 mM ammonium acetate).

TABLE 12

| Gradient table | | |
|---|---|---|
| Time (min) | Mobile phase A(%) | Mobile phase B(%) |
| 0 | 5 | 95 |
| 0.2 | 50 | 50 |
| 0.6 | 95 | 50 |
| 0.9 | 95 | 5 |
| 1 | 5 | 95 |

Flow rate: 0.8 mL/min.

<MS/MS conditions>: analysis apparatus API4000
Ionization mode: ESI
Ion polarity mode: Positive
Monitor Ion
terpenoid derivative (III) (Precursor ion (m/z): 538.5, Product ion (m/z): 460)
IS (Precursor ion (m/z): 283.2, Product ion (m/z): 265).

TABLE 13

Intravitreal concentration (nM) of terpenoid derivative (III) of present invention

| Day | No base material | PLA-0005 | PLA-0020 |
|---|---|---|---|
| 0.25 | — | 1080 ± 125 | 235 ± 14 |
| 1 | 79667 ± 22084 | 543 ± 138 | 100 ± 11 |
| 2 | 0.1 ± 0.0 | — | — |
| 7 | 0.1 ± 0.0 | 1 ± 5 | 37 ± 3 |
| 17 | — | 0 ± 0 | 1 ± 2 |
| 24 | — | 0 ± 0 | 0 ± 0 |
| 28 | — | 0 ± 0 | 0 ± 0. |

TABLE 14

Intraretinal concentration (ug/g tissue) of terpenoid derivative (III) of present invention

| Day | PLA-0020 |
|---|---|
| 0.25 | 0.84 ± 0.11 |
| 1 | 2.66 ± 2.89 |
| 7 | 0.03 ± 0.02 |
| 17 | 0.25 ± 0.15 |
| 24 | 0.13 ± 0.11 |
| 28 | 0.04 ± 0.02. |

Thus, it was able to be confirmed that the intravitreal and intraretinal concentrations of terpenoid derivative (III) of the present invention are significantly maintained by using a biodegradable polymer as the base material.

Test Example 5

Pharmacokinetic Test of Rod-shaped Implant Containing Terpenoid Derivative (III) in Rabbit Eye Microspheres composed of terpenoid derivative (III) of the present invention-PLGA-5020 [prepared by using PLGA-5020 as the base material and adjusting the mixing ratio of terpenoid derivative (III) of the present invention and PLGA-5020 to 1:9] were produced. A suspension was prepared using the microspheres and saline as a solvent such that the concentration of terpenoid derivative (III) was 3 mM.

50 uL of this suspension was intravitreally administered to each white rabbit (Oriental Yeast Co., Ltd., Kbl:NZW, male, 8 weeks old). The dose was 810 ug of the microspheres (81 ug of terpenoid derivative (III) of the present invention).

A rod-shaped implant composed of terpenoid derivative (III)-PLGA-5020 [produced by using PLGA-5020 as the base material and adjusting the mixing ratio of terpenoid derivative (III) of the present invention and PLGA-5020 to 1:9] was produced and intravitreally administered to each rabbit. The dose was 6.5 mg of the rod-shaped implant (650 ug of terpenoid derivative (III) of the present invention).

After the intravitreal administration, the rabbit was euthanized, and the intravitreal fluid was sampled. The concentration of terpenoid derivative (III) of the present invention therein was measured. The results are shown in Table 15. The numeric values shown in Table 15 below are indicated by a mean from 2 eyes. The rod-shaped implant was confirmed to allow the drug to be sustained in the vitreous body for 28 days. The rod-shaped implant, as compared with the microspheres, was further found to be able to significantly maintain the intravitreal concentration of terpenoid derivative (III).

TABLE 15

Intravitreal concentration (nM) of terpenoid derivative (III) of present invention

| Day | Microsphere | Rod-shaped implant |
|---|---|---|
| 3 | 9.4 | 3.7 |
| 7 | 0.0 | 7.9 |
| 21 | 0.0 | 8.6 |
| 28 | 0.0 | 2.5. |

Test Example 6

Action of Terpenoid Derivative (III) Microspheres on Rabbit Retina Gene

The dynamics of the Nqo1 gene as a Nrf2 target gene in the retina were tested.

50 uL of a microsphere suspension was intravitreally administered to each white rabbit (Oriental Yeast Co., Ltd., Kbl:NZW, male, 8 weeks old). The dose was 810 ug of the microspheres (81 ug of terpenoid derivative (III) of the present invention). mRNA was recovered from the retina sampled from the euthanized rabbit using a kit for extraction (manufactured by Qiagen N.V., RNeasy Mini Kit, catalog No. 74106). From the obtained mRNA, cDNA was prepared using a cDNA synthesis kit (manufactured by GE Healthcare Life Sciences, First-Strand cDNA Synthesis Kit). The obtained cDNA was amplified using a reagent (manufactured by Applied Biosystems, Inc., TaqMan® Gene Expression Master Mix (catalog No. 4369016)) and a probe, and subjected to real-time quantitative PCR (Real-time PCR HT7900 manufactured by Applied Biosystems, Inc. was used). When the expression level of the Nqo1 gene in the retina without intravitreal administration was defined as 1, the dynamics are shown in Table 16. The numeric values shown in Table 16 below were indicated by a mean of 2 eyes.

TABLE 16

Dynamics of Nqo1 gene in retina

| Day | PLA-0005 | PLA-0020 |
|---|---|---|
| 0.25 | 2.01 | 2.05 |
| 1 | 4.39 | 2.47 |
| 7 | 2.08 | 1.89 |
| 17 | 1.29 | 1.58 |
| 24 | 1.47 | 1.91 |
| 28 | 1.52 | 2.04 |

Use of PLA-0020, which was confirmed in Test Example 2 to keep the content of terpenoid derivative (III) high, as the base material was found to more strongly induce the Nrf2 target gene than use of PLA-0005 as the base material.

Test Example 7

Action of Terpenoid Derivative (III) Microspheres on Rabbit Retina Gene when Content was Changed The dynamics of the Nqo1 gene as a Nrf2 target gene in the retina were tested by changing the proportion of the compound contained in microspheres. Terpenoid derivative (III) of the present invention-PLGA-5020 [produced by using PLGA-5020 as the base material and adjusting the mixing ratio of terpenoid derivative (III) of the present invention and PLGA-5020 to 1:9 (10% by weight) or 3:7 (30% by weight)] was produced. Suspensions were prepared using each test sample and using saline as a solvent such that the concentration of terpenoid derivative (III) was 3 mM. 50 uL each of the suspensions contained 81 ug of terpenoid derivative (III).

50 uL each of the suspensions was intravitreally administered to each white rabbit (Oriental Yeast Co., Ltd., Kbl: NZW, male, 8 weeks old). After the intravitreal administration, the rabbit was euthanized, and the rabbit retina was sampled. The dynamics of the Nqo1 gene in the retina determined by real-time quantitative PCR are shown in Table 17. The numeric values shown in Table 17 below are indicated by a mean from 4 eyes and standard deviation.

TABLE 17

Dynamics of Nqo1 gene in retina

| Time | 10 wt % | 30 wt % |
|---|---|---|
| 0 | 1.0 ± 0.0 | 1.0 ± 0.0 |
| 3 | 1.3 ± 0.6 | 1.5 ± 0.6 |
| 6 | 1.8 ± 0.4 | 2.9 ± 0.1 |
| 24 | 2.1 ± 0.4 | 1.4 ± 0.3 |

Even a pharmaceutical composition having a high content of terpenoid derivative (III) was found to induce the Nrf2 target gene.

The concentration of terpenoid derivative (III) in the intravitreal fluid is shown in Table 18. The numeric values shown in Table 18 below are indicated by a mean from 4 eyes and standard deviation.

TABLE 18

Intravitreal concentration (nM) of terpenoid derivative (III) of present invention

| Time | 10 wt % | 30 wt % |
|---|---|---|
| 0 | 0 ± 0 | 0 ± 0 |
| 3 | 213 ± 156 | 152 ± 111 |
| 6 | 220 ± 163 | 440 ± 438 |
| 24 | 57 ± 27 | 37 ± 41. |

Test Example 8

Calculation of Concentration Necessary for Exertion of Pharmacological Action

Study was conducted on pharmacologically effective concentration necessary for the exertion of pharmacological action by the local administration of a sustained-release pharmaceutical composition comprising terpenoid derivative (III) of the present invention as an active ingredient to the vitreous body. The concentration at which the activity of the Nrf2 target gene Nqo1 is induced 2-fold is used as an index (Anal Biochem 1988; 169: 328). According to this method, in vivo pharmacokinetics in humans were studied by using, as an index, the concentration of terpenoid derivative (III) at which the Nrf2 target gene Hmox1 was induced 2-fold in the retina.

A sustained-release pharmaceutical composition containing 10% by weight of terpenoid derivative (III) of the present invention was produced using PLA-0020 as the base material and intravitreally administered. Results about time-dependent induction of Hmox1 is shown in Table 19.

TABLE 19

Change in dynamics of Nqo1 gene in retina by intravitreal administration of terpenoid (III) composition (microsphere) containing PLA-0020 as base material

| Day | PLA-0020 |
|---|---|
| 0.25 | 6.89 |
| 1 | 11.2 |
| 7 | 2.08 |
| 17 | 1.87 |
| 24 | 2.35 |
| 28 | 1.95. |

As is evident from this table, approximately 2-fold or more induction of Hmox1 was maintained for 28 days, i.e., approximately 1 month, from the administration of the sustained-release pharmaceutical composition.

Next, study was conducted on the drug concentration in the target tissue (retina) necessary for exhibiting these induction ratios. Change in drug concentration in the retina by the intravitreal administration of the sustained-release pharmaceutical composition is shown in Table 20.

TABLE 20

Intraretinal concentration (nM) of terpenoid derivative (III)

| Day | PLA-0020 |
|---|---|
| 0.25 | 1.56 |
| 1 | 9.48 |
| 17 | 0.46 |
| 24 | 0.24 |
| 28 | 0.07. |

Thus, the two-fold or more induction of Hmox1 was satisfied at all of the times up to 28 days, i.e., approximately 1 months, after the administration in this test. Accordingly, the induction of Hmox1 necessary for the exertion of pharmacological action was found to be obtained at a concentration equal to or higher than the minimum intraretinal drug concentration, i.e., the retinal concentration at 1 month after administration (0.07 µM from Table 14), in this test.

The dose necessary for the 2-fold induction of the Hmox1 gene for 1 month was confirmed from Table 13 to be 81 µg/body, which was the amount of the drug in the microspheres administered in this Test Example.

Next, the dose of the drug to a human was predicted from the results of this test. The capacity within the vitreous body is 4 mL for a human and 1.5 to 2.5 mL for a rabbit (Invest Ophthalmol Vis Sci 2007; 48: 2230). Accordingly, the drug concentration in the rabbit vitreous body can probably be extrapolated to a human by correction using this volume ratio of approximately 2 times. From the dose 81 µg/body (rabbit) of the drug used for the obtainment of the data of Table 13, the necessary dose of the drug was calculated to be 162 µg/body provided that the clinically desirable duration of the pharmacological action is 1 month. On the other hand, the amount of the drug contained in Ozudex® launched as a rod-shaped implant pharmaceutical composition is 700 µg (Invest Ophthalmol Vis Sci 20011; 52: 80). From these, a pharmaceutical composition comprising terpenoid derivative (III) of the present invention as an active ingredient was presumed to be able to administer the drug in an amount that clinically exerts its pharmacological effect.

Deposition No.
NITE BP-01914
NITE BP-01915
NITE BP-01916

Free Text for Sequence Listing
SEQ ID NO: 1: Partial nucleotide sequence of SANK 70214 16S rDNA
SEQ ID NO: 2: Partial nucleotide sequence of SANK 70314 16S rDNA
SEQ ID NO: 3: DNA sequence of a protein of SANK 70214 having hydroxylation activity
SEQ ID NO: 4: DNA sequence of a protein of SANK 70314 having hydroxylation activity
SEQ ID NO: 5: Amino acid sequence of the protein of SANK 70214 having hydroxylation activity
SEQ ID NO: 6: Amino acid sequence of the protein of SANK 70314 having hydroxylation activity

The invention claimed is:

1. A terpenoid derivative represented by formula (I):

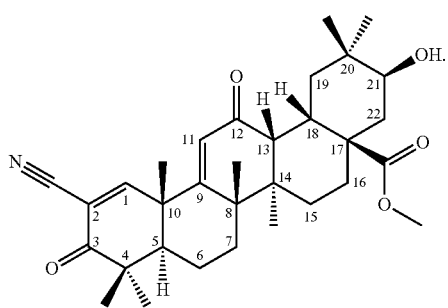

(I)

2. A pharmaceutical composition comprising a terpenoid derivative according to claim 1 as an active ingredient and a pharmacologically acceptable carrier.

3. A sustained-release pharmaceutical composition for the treatment of an eye disease, comprising a terpenoid derivative according to claim 1 as an active ingredient, wherein the sustained-release pharmaceutical composition maintains a pharmacological action thereof for 1 week or longer by the sustained release of the terpenoid derivative under physiological conditions and has a base material administrable to the vitreous body and a form administrable to the vitreous body.

4. The sustained-release pharmaceutical composition for the treatment of an eye disease according to claim 3, wherein the base material is a biodegradable polymer.

5. The sustained-release pharmaceutical composition for the treatment of an eye disease according to claim 3, wherein the base material is polylactic acid or poly(lactic-co-glycolic acid).

6. The sustained-release pharmaceutical composition for the treatment of an eye disease according to claim 3, wherein the form is microspheres.

7. The sustained-release pharmaceutical composition for the treatment of an eye disease according to claim 3, wherein the form is a rod.

8. The sustained-release pharmaceutical composition for the treatment of an eye disease according to claim 3, wherein the content of the active ingredient is 5% by weight to 80% by weight.

9. The sustained-release pharmaceutical composition for the treatment of an eye disease according to claim 3, wherein the content of the active ingredient is 20% by weight to 60% by weight.

10. The sustained-release pharmaceutical composition for the treatment of an eye disease according to claim 3, wherein the content of the active ingredient is 20% by weight to 60% by weight, the sustained-release pharmaceutical composition maintains a pharmacological action thereof for 1 week or longer by the sustained release of the active ingredient under physiological conditions, the base material is polylactic acid or poly(lactic-co-glycolic acid), and the form is a microsphere or a rod.

11. The sustained-release pharmaceutical composition for the treatment of an eye disease according to claim 3, wherein the eye disease is age-related macular degeneration.

12. The sustained-release pharmaceutical composition for the treatment of an eye disease according to claim 3, wherein the eye disease is diabetic macular edema and/or retinal vein occlusion.

* * * * *

UNITED STATES PATENT AND TRADEMARK OFFICE
CERTIFICATE OF CORRECTION

PATENT NO. : 10,208,082 B2
APPLICATION NO. : 15/510208
DATED : February 19, 2019
INVENTOR(S) : Kasuya et al.

Page 1 of 1

It is certified that error appears in the above-identified patent and that said Letters Patent is hereby corrected as shown below:

In the Specification

| Column | Line | Error |
|---|---|---|
| 3 | 51-52 | "Non-Patent Literature 19: Drug Discovery Today 2011; 16: 1-8" should read --Non-Patent Literature 19: Drug Discovery Today 2011; 16: 5-6: 270-277-- |

Signed and Sealed this
Tenth Day of September, 2019

Andrei Iancu
*Director of the United States Patent and Trademark Office*

SEQUENCE LISTING

```
<160> NUMBER OF SEQ ID NOS: 6

<210> SEQ ID NO 1
<211> LENGTH: 1476
<212> TYPE: DNA
<213> ORGANISM: Unknown
<220> FEATURE:
<223> OTHER INFORMATION: Bacillus sp.

<400> SEQUENCE: 1
gcgtgcctaa tacatgcaag tcgagcggac gttttttgaag cttgctttaa aaacgttagc      60
ggcggacggg tgagtaacac gtgggcaacc taccttatcg actgggataa ctccgggaaa     120
ccggggctaa taccggataa catctagcac ctcctggtgc cggattgaaa gagggcttct     180
tgctctcacg atgagatggg cccgcggcgc attagctagt tggagaggta atggctcccc     240
aaggcgacga tgcgtagccg acctgagagg gtgatcggcc acactgggac tgagacacgg     300
cccagactcc tacgggaggc agcagtaggg aatcttccgc aatggacgaa agtctgacgg     360
agcaacgccg cgtgagtgat gaagggtttc ggctcgtaaa gctctgttat gagggaagaa     420
cacgtaccgt tcgaataggg cggtaccttg acggtacctc atcagaaagc cacggctaac     480
tacgtgccaa cagccgcggt aatacgtagg tggcaagcgt tgtccggaat tattgggcgt     540
aaagcgcgcg caggcggcct tttaagtctg atgtgaaatc ttgcggctca accgcaagcg     600
gccattggaa actgggaggc ttgagtacag aagaggagag tggaattcca cgtgtagcgg     660
tgaaatgcgt agatatgtgg aggaacacca gtggcgaagg cgactctctg gtctgtaact     720
gacgctgagg cgcgaaagcg tggggagcaa acaggattag ataccctggt agtccacgcc     780
gtaaacgatg agtgctaggt gttagggggtt tcgatgccccg tagtgccgaa gttaacacat     840
taagcactcc gcctggggag tacggccgca aggctgaaac tcaaaggaat tgacggggggc     900
ccgcacaagc agtggagcat gtggtttaat tcgaagcaac gcgaagaacc ttaccaggtc     960
ttgacatcct ttgaccactc tggagacaga gcttcccctt cggggggcaaa gtgacaggtg    1020
gtgcatggtt gtcgtcagct cgtgtcgtga tgttgggt taagtcccgc aacgagcgca    1080
acccttgacc ttagttgcca gcatttagtt gggcactcta aggtgactgc cggtgacaaa    1140
ccggaggaag gtgggggatga cgtcaaatca tcatgccccct tatgacctgg gctacacacg    1200
tgctacaatg gatggtacaa agggttgcga agccgcgagg tgaagccaat cccataaagc    1260
cattctcagt tcggattgta ggctgcaact cgcctgcatg aagctggaat tgctagtaat    1320
cgcggatcag catgccgcgg tgaatacgtt cccgggcctt gtacacaccg cccgtcacac    1380
cacgagagtt tgtaacaccc gaagtcggtg aggtaacctt ttggagccag ccgccgaagg    1440
tgggacagat gattggggtg aagtcgtaac aaggta                               1476
```

<210> SEQ ID NO 2
<211> LENGTH: 1383
<212> TYPE: DNA
<213> ORGANISM: Bacillus megaterium

<400> SEQUENCE: 2

| | |
|---|---|
| gatgaacgct ggcggcgtgc ctaatacatg caagtcgagc gaactgatta gaagcttgct | 60 |
| tctatgacgt tagcggcgga cgggtgagta acacgtgggc aacctgcctg taagactggg | 120 |
| ataacttcgg gaaaccgaag ctaataccgg ataggatctt ctccttcatg ggagatgatt | 180 |
| gaaagatggt ttcggctatc acttacagat gggcccgcgg tgcattagct agttggtgag | 240 |
| gtaacggctc accaaggcaa cgatgcatag ccgacctgag agggtgatcg ccacactgg | 300 |
| gactgagaca cggcccagac tcctacggga ggcagcagta gggaatcttc cgcaatggac | 360 |
| gaaagtctga cggagcaacg ccgcgtgagt gatgaaggct ttcgggtcgt aaaactctgt | 420 |
| tgttagggaa gaacaagtac aagagtaact gcttgtacct tgacggtacc taaccagaaa | 480 |
| gccacggcta actacgtgcc agcagccgcg gtaatacgta ggtggcaagc gttatccgga | 540 |
| attattgggc gtaaagcgcg cgcaggcggt ttcttaagtc tgatgtgaaa gcccacggct | 600 |
| caaccgtgga gggtcattgg aaactgggga acttgagtgc agaagagaaa agcggaattc | 660 |
| cacgtgtagc ggtgaaatgc gtagagatgt ggaggaacac cagtggcgaa ggcggctttt | 720 |
| tggtctgtaa ctgacgctga ggcgcgaaag cgtgggagc aaacaggatt agataccctg | 780 |
| gtagtccacg ccgtaaacga tgagtgctaa gtgttagagg gtttccgccc tttagtgctg | 840 |
| cagctaacgc attaagcact ccgcctgggg agtacggtcg caagactgaa actcaaagga | 900 |
| attgacgggg gcccgcacaa gcggtggagc atgtggttta attcgaagca acgcgaagaa | 960 |
| ccttaccagg tcttgacatc ctctgacaac tctagagata gagcgttccc cttcggggga | 1020 |
| cagagtgaca ggtggtgcat ggttgtcgtc agctcgtgtc gtgagatgtt gggttaagtc | 1080 |
| ccgcaacgag cgcaacccct tgatcttagt tgccagcattt agttgggcac tctaaggtga | 1140 |
| ctgccggtga caaaccggag gaaggtgggg atgacgtcaa atcatcatgc cccttatgac | 1200 |
| ctgggctaca cacgtgctac aatggatggt acaaagggct gcaagaccgc gaggtcaagc | 1260 |
| caatcccata aaaccattct cagttcggat tgtaggctgc aactcgccta catgaagctg | 1320 |
| gaatcgctag taatcgcgga tcagcatgcc gcggtgaata cgttcccggg ccttgtacac | 1380 |
| acc | 1383 |

<210> SEQ ID NO 3
<211> LENGTH: 1254
<212> TYPE: DNA
<213> ORGANISM: Unknown
<220> FEATURE:
<223> OTHER INFORMATION: Bacillus sp.

<400> SEQUENCE: 3

| | |
|---|---|
| atgagtcatg ctgcgaacgt aaagagaaa gtgttaggct ttttaagtgg aaaaagtgga | 60 |
| gaaaaccgt tcatttatt tgctgaactc cgagatttgg gatcggtcgt ctcaatccct | 120 |
| aacccaatgg gtgatccaaa caaaaatgct tggatgatca ctaagatgga tacagcaaca | 180 |
| aaggttctaa aggattcaaa acggttcacg gttgatccgg catcgattga aaaggaaagt | 240 |
| ggatttagag cggaaatggt ttcagatcca gatgattctc ccgataccct ttttacaggt | 300 |
| aagtctatgt tttttattga cggtattgat cataagcgat tgcgaatgct cgtatcgaaa | 360 |
| gcattcactc cgaaatatat ggaagggtta cgtcctcgta tacaggaaat agcagacggt | 420 |

```
ttacttgatc aagttgaatc aaaaggtgag atggatcttg taaaagatta cgcctatcct    480
ctaccgatta ttgtgatatc agaaatgtta ggagtaccta agaagatca tgaaaatcta    540 caaatatggt catcggctat agctaaaggc ttaggctggg ggaaacaaga tccagccgtg    600
cagcagcatc taaaagattt tggagattac acaaagaagc ttgtagaaaa gaaaagagct    660
catttagagg atgatctcat cagccagctg atccaaattg aagaagggg agaacgtcta    720 agtgaagaag agctgatctc gatgattaca cttcttatct ttgcagggca tgaaacaacg    780
tctaacctga tcgctacagg tagtatgatg ttatttgacc acccggagca attaaataaa    840
ttaaaatcaa acctagatct ggtaccaact gctgttgaag aacttctgcg ttttaacggt    900
ccttctacaa ctgtaggccc acgtttcgca aaggaagatg tgaatataga tggacaagag    960
atcaaaaaag gagatatgct ccttatcctt gttaagtcag cgaaccgaga tgaagaagtg    1020
ttctctgatt ccgaagaatt ggatgtcagt cgttcaattc accgacattt agcctttggt    1080
tttggtatgc atatgtgcct ggagctcct ttagctcgag tggaaggaga cgtcgctttt    1140
acaacgctct aaaaaggct accgaacata gagcttagta ttccgcctga ggaagtaaag    1200
tggcaattca cgctctcaac gcaaggcctt tcatcattgc ccgtttcatt ctaa          1254
```

<210> SEQ ID NO 4
<211> LENGTH: 1215
<212> TYPE: DNA
<213> ORGANISM: Bacillus megaterium

<400> SEQUENCE: 4

```
atgaaaaccg aaagagaaaa cggaatcgtc cgtcaagtga atacgattca acaaaagaa     60 gagcgcttta atccttttc atggtatgaa gagatgagaa acagcgcgcc tgtgcgatgg    120
gatgaagaaa ggcaggtatg ggatgttttt cactatgatg gggtcaaaga agtgctggaa    180
caaaaaaata tttttttcttc tgatcgaaga cctccacaaa accaaagaca aactgctcta    240
ggaacgagcc taattaatat tgatccgcct aagcatgctg aaatgagagc gcttgttaat    300
aaagctttta cgcctaaagc aatgaaagca tgggagccta aaattgcgcg cattaccgct    360
gaattattac aagaagttga gcatcttgaa gatattgata tagtcgagca tctttcctat    420
ccgcttccgg ttatggtaat tgccgatatt ttaggcgtcc cgatagaaga tcagcgtcag    480
tttaaagatt ggtcggatat tatcgtagcg ggtccatcga ataatgaacg tgaaacgctc    540
gaaaaattgc agcaagagaa atgaaagca acgatgagt tagaaactta cttttatcga    600
atcattgaag aaaagcgcac gcagccagga gatgatatta tttccgtgct tcttcaagca    660
aaagaagaag ggaagcagct aacggatgaa gaaatcgtcg ggttttccat tttgctgctg    720
attgcaggca acgaaacaac cacgaactta atttcaaata cgatttattg tttaatggaa    780
gataaagctt ctttttgaacg actcaaacga gaaaagaac ttttaccttc tgcgattgaa    840
gaagttcttc gctatcgttc acccgttcag gctcttcacc gaatcgtaaa aaagatgtg    900 gttcttgcag ggaagaaatt aaaagcgggc gaacacgtcg ttccatggat gggatccgcg    960
caccgagatg cgcagtattt tgaagacccg gatgtatttc aaatcgatcg aaagccaaat    1020
atccatatgg catttggaag agggattcat ttttgcttag gagcaccgct tgctcgaata    1080 gaagcaaag ttatgctggc tgaactgatt gaccgctatc cgcatatgga ctggagcccg    1140
gcatttgagt taaagccgat tgaaagcacg tttgtgtacg ggttagaaga attattgatt    1200
cgtaaacatg tataa                                                      1215
```

```
<210> SEQ ID NO 5
<211> LENGTH: 417
<212> TYPE: PRT
<213> ORGANISM: Unknown
<220> FEATURE:
<223> OTHER INFORMATION: Bacillus sp.

<400> SEQUENCE: 5
```

| | | | | | | | | | | | | | | |
|---|---|---|---|---|---|---|---|---|---|---|---|---|---|---|
| Met | Ser | His | Ala | Ala | Asn | Val | Lys | Glu | Lys | Val | Leu | Gly | Phe | Leu | Ser |
| 1 | | | | 5 | | | | | 10 | | | | | 15 | |
| Gly | Lys | Ser | Gly | Glu | Asn | Pro | Phe | His | Leu | Phe | Ala | Glu | Leu | Arg | Asp |
| | | | 20 | | | | | 25 | | | | | 30 | | |
| Leu | Gly | Ser | Val | Val | Ser | Ile | Pro | Asn | Pro | Met | Gly | Asp | Pro | Asn | Lys |
| | | 35 | | | | | 40 | | | | | 45 | | | |
| Asn | Ala | Trp | Met | Ile | Thr | Lys | Met | Asp | Thr | Ala | Thr | Lys | Val | Leu | Lys |
| | 50 | | | | | 55 | | | | | 60 | | | | |
| Asp | Ser | Lys | Arg | Phe | Thr | Val | Asp | Pro | Ala | Ser | Ile | Glu | Lys | Glu | Ser |
| 65 | | | | | 70 | | | | | 75 | | | | | 80 |
| Gly | Phe | Arg | Ala | Glu | Met | Val | Ser | Asp | Asp | Ser | Pro | Asp | Thr |
| | | | | 85 | | | | | 90 | | | | | 95 | |
| Phe | Phe | Thr | Gly | Lys | Ser | Met | Val | Phe | Ile | Asp | Gly | Ile | Asp | His | Lys |
| | | | 100 | | | | | 105 | | | | | 110 | | |
| Arg | Leu | Arg | Met | Leu | Val | Ser | Lys | Ala | Phe | Thr | Pro | Lys | Tyr | Met | Glu |
| | | 115 | | | | | 120 | | | | | 125 | | | |
| Gly | Leu | Arg | Pro | Arg | Ile | Gln | Glu | Ile | Ala | Asp | Gly | Leu | Leu | Asp | Gln |
| | 130 | | | | | 135 | | | | | 140 | | | | |
| Val | Glu | Ser | Lys | Gly | Glu | Met | Asp | Leu | Val | Lys | Asp | Tyr | Ala | Tyr | Pro |
| 145 | | | | | 150 | | | | | 155 | | | | | 160 |
| Leu | Pro | Ile | Ile | Val | Ile | Ser | Glu | Met | Leu | Gly | Val | Pro | Lys | Glu | Asp |
| | | | | 165 | | | | | 170 | | | | | 175 | |
| His | Glu | Asn | Leu | Gln | Ile | Trp | Ser | Ser | Ala | Ile | Ala | Lys | Gly | Leu | Gly |
| | | | 180 | | | | | 185 | | | | | 190 | | |
| Trp | Gly | Lys | Gln | Asp | Pro | Ala | Val | Gln | Gln | His | Leu | Lys | Asp | Phe | Gly |
| | | 195 | | | | | 200 | | | | | 205 | | | |
| Asp | Tyr | Thr | Lys | Lys | Leu | Val | Glu | Lys | Lys | Arg | Ala | His | Leu | Glu | Asp |
| | 210 | | | | | 215 | | | | | 220 | | | | |
| Asp | Leu | Ile | Ser | Gln | Leu | Ile | Gln | Ile | Glu | Glu | Glu | Gly | Glu | Arg | Leu |
| 225 | | | | | 230 | | | | | 235 | | | | | 240 |
| Ser | Glu | Glu | Glu | Leu | Ile | Ser | Met | Ile | Thr | Leu | Leu | Ile | Phe | Ala | Gly |
| | | | | 245 | | | | | 250 | | | | | 255 | |
| His | Glu | Thr | Thr | Ser | Asn | Leu | Ile | Ala | Thr | Gly | Ser | Met | Met | Leu | Phe |
| | | | 260 | | | | | 265 | | | | | 270 | | |
| Asp | His | Pro | Glu | Gln | Leu | Asn | Lys | Leu | Lys | Ser | Asn | Leu | Asp | Leu | Val |
| | | 275 | | | | | 280 | | | | | 285 | | | |
| Pro | Thr | Ala | Val | Glu | Glu | Leu | Leu | Arg | Phe | Asn | Gly | Pro | Ser | Thr | Thr |
| | 290 | | | | | 295 | | | | | 300 | | | | |
| Val | Gly | Pro | Arg | Phe | Ala | Lys | Glu | Asp | Val | Asn | Ile | Asp | Gly | Gln | Glu |
| 305 | | | | | 310 | | | | | 315 | | | | | 320 |
| Ile | Lys | Lys | Gly | Asp | Met | Leu | Leu | Ile | Leu | Val | Lys | Ser | Ala | Asn | Arg |
| | | | | 325 | | | | | 330 | | | | | 335 | |
| Asp | Glu | Glu | Val | Phe | Ser | Asp | Ser | Glu | Glu | Leu | Asp | Val | Ser | Arg | Ser |
| | | | 340 | | | | | 345 | | | | | 350 | | |
| Ile | His | Arg | His | Leu | Ala | Phe | Gly | Phe | Gly | Met | His | Met | Cys | Leu | Gly |
| | | 355 | | | | | 360 | | | | | 365 | | | |

```
Ala Pro Leu Ala Arg Val Glu Gly Asp Val Ala Phe Thr Thr Leu Leu
        370                 375                 380

Lys Arg Leu Pro Asn Ile Glu Leu Ser Ile Pro Pro Glu Glu Val Lys
385                 390                 395                 400

Trp Gln Phe Thr Leu Ser Thr Gln Gly Leu Ser Ser Leu Pro Val Ser
                    405                 410                 415

Phe

<210> SEQ ID NO 6
<211> LENGTH: 404
<212> TYPE: PRT
<213> ORGANISM: Bacillus megaterium

<400> SEQUENCE: 6

Met Lys Thr Glu Arg Glu Asn Gly Ile Val Arg Gln Val Asn Thr Ile
1               5                   10                  15

Gln Thr Lys Glu Glu Arg Phe Asn Pro Phe Ser Trp Tyr Glu Glu Met
            20                  25                  30

Arg Asn Ser Ala Pro Val Arg Trp Asp Glu Glu Arg Gln Val Trp Asp
        35                  40                  45

Val Phe His Tyr Asp Gly Val Lys Glu Val Leu Glu Gln Lys Asn Ile
    50                  55                  60

Phe Ser Ser Asp Arg Arg Pro Pro Gln Asn Gln Arg Gln Thr Ala Leu
65                  70                  75                  80

Gly Thr Ser Leu Ile Asn Ile Asp Pro Pro Lys His Ala Glu Met Arg
                85                  90                  95

Ala Leu Val Asn Lys Ala Phe Thr Pro Lys Ala Met Lys Ala Trp Glu
            100                 105                 110

Pro Lys Ile Ala Arg Ile Thr Ala Glu Leu Leu Gln Glu Val Glu His
        115                 120                 125

Leu Glu Asp Ile Asp Ile Val Glu His Leu Ser Tyr Pro Leu Pro Val
    130                 135                 140

Met Val Ile Ala Asp Ile Leu Gly Val Pro Ile Glu Asp Gln Arg Gln
145                 150                 155                 160

Phe Lys Asp Trp Ser Asp Ile Ile Val Ala Gly Pro Ser Asn Asn Glu
                165                 170                 175

Arg Glu Thr Leu Glu Lys Leu Gln Gln Glu Lys Met Lys Ala Asn Asp
            180                 185                 190

Glu Leu Glu Thr Tyr Phe Tyr Arg Ile Ile Glu Glu Lys Arg Thr Gln
        195                 200                 205

Pro Gly Asp Asp Ile Ile Ser Val Leu Leu Gln Ala Lys Glu Glu Gly
    210                 215                 220

Lys Gln Leu Thr Asp Glu Glu Ile Val Gly Phe Ser Ile Leu Leu Leu
225                 230                 235                 240

Ile Ala Gly Asn Glu Thr Thr Thr Asn Leu Ile Ser Asn Thr Ile Tyr
                245                 250                 255

Cys Leu Met Glu Asp Lys Ala Ser Phe Glu Arg Leu Lys Arg Glu Lys
            260                 265                 270

Glu Leu Leu Pro Ser Ala Ile Glu Glu Val Leu Arg Tyr Arg Ser Pro
        275                 280                 285

Val Gln Ala Leu His Arg Ile Val Lys Lys Asp Val Val Leu Ala Gly
    290                 295                 300

Lys Lys Leu Lys Ala Gly Glu His Val Val Pro Trp Met Gly Ser Ala
305                 310                 315                 320
```

```
His Arg Asp Ala Gln Tyr Phe Glu Asp Pro Asp Val Phe Gln Ile Asp
            325                 330                 335

Arg Lys Pro Asn Ile His Met Ala Phe Gly Arg Gly Ile His Phe Cys
            340                 345                 350

Leu Gly Ala Pro Leu Ala Arg Ile Glu Ala Lys Val Met Leu Ala Glu
            355                 360                 365

Leu Ile Asp Arg Tyr Pro His Met Asp Trp Ser Pro Ala Phe Glu Leu
            370                 375                 380

Lys Pro Ile Glu Ser Thr Phe Val Tyr Gly Leu Glu Glu Leu Leu Ile
385                 390                 395                 400

Arg Lys His Val
```